(12) United States Patent
Hadwiger et al.

(10) Patent No.: US 11,767,531 B2
(45) Date of Patent: *Sep. 26, 2023

(54) DEFINED MULTI-CONJUGATES OLIGONUCLEOTIDES

(71) Applicant: MPEG LA, L.L.C., Chevy Chase, MD (US)

(72) Inventors: Philipp Hadwiger, Kulmbach (DE); Hans-Peter Vornlocher, Kulmbach (DE); Jonathan Miles Brown, Silver Spring, MD (US); James Everett Dahlman, Atlanta, GA (US); Kristin K. H. Neuman, Larchmont, NY (US)

(73) Assignee: MPEG LA, LLC, Chevy Chase, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/747,924

(22) Filed: May 18, 2022

(65) Prior Publication Data

US 2022/0290148 A1 Sep. 15, 2022

Related U.S. Application Data

(62) Division of application No. 15/735,707, filed as application No. PCT/US2016/037685 on Jun. 15, 2016, now Pat. No. 11,352,629.

(60) Provisional application No. 62/216,317, filed on Sep. 9, 2015, provisional application No. 62/216,318, filed on Sep. 9, 2015, provisional application No. 62/216,314, filed on Sep. 9, 2015, provisional application No. 62/203,243, filed on Aug. 10, 2015, provisional application No. 62/175,718, filed on Jun. 15, 2015, provisional application No. 62/175,714, filed on Jun. 15, 2015, provisional application No. 62/175,709, filed on Jun. 15, 2015.

(51) Int. Cl.
| | |
|---|---|
| *C12N 15/115* | (2010.01) |
| *C12N 15/11* | (2006.01) |
| *C12N 15/113* | (2010.01) |
| *A61K 9/127* | (2006.01) |
| *A61K 47/54* | (2017.01) |
| *A61K 47/69* | (2017.01) |

(52) U.S. Cl.
CPC ........... *C12N 15/115* (2013.01); *A61K 9/127* (2013.01); *A61K 47/549* (2017.08); *A61K 47/6911* (2017.08); *C12N 15/111* (2013.01); *C12N 15/113* (2013.01); *C12N 2310/14* (2013.01); *C12N 2310/315* (2013.01); *C12N 2310/317* (2013.01); *C12N 2310/321* (2013.01); *C12N 2310/322* (2013.01); *C12N 2310/346* (2013.01); *C12N 2310/351* (2013.01); *C12N 2310/3521* (2013.01); *C12N 2310/3533* (2013.01); *C12N 2310/51* (2013.01)

(58) Field of Classification Search
CPC ............... C12N 15/113; C12N 15/115; C12N 2310/14; C12N 2310/51; C12N 2310/346; A61K 47/549
USPC .... 435/6.1, 91.1, 91.31, 455, 458; 536/23.1, 536/24.5
See application file for complete search history.

(56) References Cited

U.S. PATENT DOCUMENTS

| | | | |
|---|---|---|---|
| 5,552,535 | A | 9/1996 | McLean et al. |
| 8,106,173 | B2 | 1/2012 | Kandimalla et al. |
| 8,110,674 | B2 | 2/2012 | Manoharan et al. |
| 8,188,261 | B2 | 5/2012 | Kandimalla et al. |
| 8,362,233 | B2 | 1/2013 | Kandimalla et al. |
| 8,431,544 | B1 | 4/2013 | Agrawal et al. |
| 8,580,946 | B2 | 11/2013 | Park et al. |
| 8,759,310 | B2 | 6/2014 | Kandimalla et al. |
| 9,243,050 | B2 | 1/2016 | Kandimalla et al. |
| 9,255,269 | B2 | 2/2016 | Park et al. |
| 9,616,085 | B2 | 4/2017 | Hong et al. |
| 9,644,209 | B2 | 5/2017 | Park et al. |
| 10,597,659 | B2 | 3/2020 | Park et al. |
| 11,078,484 | B2 | 8/2021 | Brown et al. |
| 11,352,629 | B2 * | 6/2022 | Hadwiger ............ C12N 15/113 |

(Continued)

FOREIGN PATENT DOCUMENTS

| | | |
|---|---|---|
| CN | 103796657 A | 5/2014 |
| JP | 2014-527819 | 10/2014 |

(Continued)

OTHER PUBLICATIONS

Lee et al (Biomaterials, vol. 32, pp. 2359-2368 (2011)), (Year: 2011).*
Yoo et al (Chem. Commun., vol. 50, pp. 6765-6767 (2014)) (Year: 2014).*
And Mok et al (Nature Materials, vol. 9, pp. 272-278 (2010)). (Year: 2010).*
U.S. Appl. No. 17/922,254 (Year: 2022).*
U.S. Appl. No. 17/985,005 (Year: 2022).*

(Continued)

*Primary Examiner* — Jane J Zara
(74) *Attorney, Agent, or Firm* — Knobbe, Martens, Olson & Bear, LLP

(57) ABSTRACT

Defined multi-conjugate oligonucleotides can have predetermined sizes and compositions. For example, in various embodiment, defined multi-conjugate oligonucleotides can have advantageous properties, for example in the form of defined multi-conjugate siRNA (i.e., including two, three or more siRNA) having enhanced intracellular delivery and/or multi-gene silencing effects. In various embodiment, the defined multi-conjugate oligonucleotides can be synthesized via new synthetic intermediates and methods. The defined multi-conjugate oligonucleotides can be used, for example, in reducing gene expression, biological research, treating or preventing medical conditions, or to produce new or altered phenotypes in cells or organisms.

18 Claims, 34 Drawing Sheets

Specification includes a Sequence Listing.

(56) References Cited

U.S. PATENT DOCUMENTS

| | | |
|---|---|---|
| 2004/0235773 A1 | 11/2004 | Zhao et al. |
| 2007/0287681 A1 | 12/2007 | Jeong et al. |
| 2008/0108801 A1 | 5/2008 | Manoharan et al. |
| 2008/0214436 A1 | 9/2008 | Yu et al. |
| 2008/0287383 A1 | 11/2008 | Quay et al. |
| 2008/0311040 A1 | 12/2008 | Berry et al. |
| 2009/0126038 A1 | 5/2009 | Van De craen et al. |
| 2013/0064786 A1 | 3/2013 | Hong et al. |
| 2013/0330293 A1 | 12/2013 | Long et al. |
| 2014/0194610 A1 | 7/2014 | Verdine et al. |
| 2014/0309281 A1 | 10/2014 | Park et al. |
| 2015/0197754 A9 | 7/2015 | Park et al. |
| 2015/0299695 A1 | 10/2015 | Uhlmann et al. |
| 2015/0315585 A1 | 11/2015 | Uhlmann et al. |
| 2016/0193354 A1 | 7/2016 | Noe et al. |
| 2016/0298124 A1 | 10/2016 | Borodovsky et al. |
| 2016/0347780 A1 | 12/2016 | Wada et al. |
| 2017/0189525 A1 | 7/2017 | Brunskill et al. |
| 2017/0204408 A9 | 7/2017 | Lewis |
| 2017/0349896 A1 | 12/2017 | Albaek et al. |
| 2018/0080028 A1 | 3/2018 | Park et al. |
| 2018/0312839 A1 | 11/2018 | Bhat et al. |
| 2019/0062743 A1 | 2/2019 | Uhlmann et al. |
| 2019/0085331 A1 | 3/2019 | Hadwiger et al. |
| 2020/0239892 A1 | 7/2020 | Park et al. |
| 2020/0308578 A1* | 10/2020 | Woolf .................. C12N 15/111 435/375 |
| 2021/0380979 A1 | 12/2021 | Brown et al. |
| 2023/0070118 A1 | 3/2023 | Park et al. |
| 2023/0114023 A1 | 4/2023 | Brown et al. |

FOREIGN PATENT DOCUMENTS

| | | | |
|---|---|---|---|
| JP | 2017-565893 A | 7/2018 | |
| JP | 2011-518784 | 10/2019 | |
| KR | 10-2011-0083919 A | 7/2011 | |
| WO | WO 2004/030634 A2 | 4/2004 | |
| WO | WO 2004/090108 A2 | 10/2004 | |
| WO | WO 2004/091515 A2 | 10/2004 | |
| WO | WO 2004/094345 A2 | 11/2004 | |
| WO | WO 2004/094595 A2 | 11/2004 | |
| WO | WO 2007/117686 A2 | 10/2007 | |
| WO | WO 2008/109105 A2 | 9/2008 | |
| WO | WO-2008109105 A2 * | 9/2008 | ........... C12N 15/111 |
| WO | WO 2009/014887 A2 | 1/2009 | |
| WO | WO 2009/126933 A2 | 10/2009 | |
| WO | WO2010/021720 A1 | 2/2010 | |
| WO | WO 2011/031520 A1 | 3/2011 | |
| WO | WO 2011/109380 A1 | 9/2011 | |
| WO | WO 2013/040429 A1 | 3/2013 | |
| WO | WO 2014/043544 A1 | 3/2014 | |
| WO | WO-2014043544 A1 * | 3/2014 | ........... C12N 15/111 |
| WO | WO-2014208973 A1 * | 12/2014 | ........... C12N 15/111 |
| WO | WO 2019/105421 A1 | 6/2019 | |

OTHER PUBLICATIONS

Bolcato-Bellemin et al. (2007), "Sticky overhangs enhance siRNA-mediated gene silencing," Proc. Natl. Acad. Sci. USA, 104:41: 16050-16055.

Brown, JM et al., Ligan Conjugated Multimeric siRNAs Enable Enhanced Uptake and Multiplexed Gene Silencing. Nucieic Acid Therapeutics, Sep. 26, 2019, vol. 29, No. 5, pp. 231-244; entire document. DOI: 10.1089/nat.2019.0782.

Elbashir et al. (2001), "Duplexes of 21-nucleotide RNAs mediate RNA interference in cultured mammalian cells," Nature, 411: 494-498.

Gary et al. (2007), "Polymer-based siRNA delivery: Perspective on the fundamental and phenomenological distinctions from polymer-based DNA delivery," J. Controlled Release, 121: 64-73.

Jeong, J.H., et al., siRNA conjugate delivery systems. Bioconjug Chem. Jan. 2009;20(1):5-14. doi: 10.1021/bc800278e.

Kang et al. "HER2 RNA Aptamerand Cell Penetrating Peptide-Mediated Delivery of Multimeric Antisense Strands of siRNAs for Gene Silencing: Multimeric antisense strands of siRNAS", bull. Korean chem. Soc., vol. 37, No. 9, Aug. 29, 2016, pp. 1440-1444, XPO55746857, ISSN: 1229-5949, DOI: 10.1002/bkcs.10886.

Kim, S.H., et al., Local and systemic delivery of VEGF siRNA using polyelectrolyte complex micelles for effective treatment of cancer. J Control Release. Jul. 14, 2008;129(2): 107-16. doi: 10.1016/j.jconrel.2008.03.008. Epub Mar. 14, 2008.

Kim, S.H., et al., LHRH receptor-mediated delivery of siRNA using polyelectrolyte complex micelles self-assembled rom siRNA-PEG-LHRH conjugate and PEI. Bioconjug Chem. Nov. 19, 2008;19(11):2156-62. doi: 10.1021/bc800249n.

Kim et al. (2006) "PEG conjugated VEGF siRNA for anti-angiogenic gene therapy," Journal of Controlled Release, 116:123-129.

Lee, Soo Hyeon, et al. "Dual gene targeted multimeric siRNA for combinatorial gene silencing." Biomaterials, vol. 32, No. 9, Oct. 23, 2010, pp. 2359-2368.

Lee et al., (2012) "Molecularly Self-Assembled Nucleic-Acid Nanoparticles for Targeted in Vivo siRNA Delivery," Nature Nanotechnology, 7(6):389-393.

Lee et al., (2012) "Small-Interfering RNA (siRNA)-Based Functional Micro- and Nanostructures for Efficient and Selective Gene Silencing," Accounts of Chemical Research, 45(7):1014-1025.

Mok et al., "Self-crosslinked and reducible fusogenic peptides for intracellular delivery of siRNA", Biopolymers. J008 Ocl;89(10):881-8. doi: 10.1002/bip.21032.

Mok et al., "Multimeric small interfering ribonucleic acid for highly efficient sequence-specific gene silencing", Natural Materials, vol. 9(3):272-278 (2010).

Moschos, S.A, et al., Lung delivery studies using siRNA conjugated to TAT(48-60) and penetralin reveal peptide nduced reduction in gene expression and induction of innate immunity. Bioconjug Chem. Sep.-Oct. 2007;18(5):1450-9. Epub Aug. 21, 2007.

Muratovska, A., et al., Conjugate for efficient delivery of short interfering RNA (siRNA) into mammalian cells. FEBS Lett. Jan. 30, 2004;558(1-3):63-8.

Schiffelers RM, et al. "Cancer siRNA therapy by tumor selective delivery with ligand-targeted sterically stabilized nanoparticle", Nucleic Acids Res. 32 (2004) e149. Published Oct. 1, 2004.

Subramanian et al., "Enhancing Antisense Efficacy with Multimers and Multi-Targeting Oligonucleotides (MTOs) Using Cleavable Linkers," Nucleic Acids Research, Oct. 7, 2015, vol. 43, Issue 19, pp. 9123-9132.

Sugo, T. et al., Development of antibody-siRNA conjugate targeted to cardiac and skeletal muscles, Journal of Controlled Release, 237 (2016) 1-13.

Sun et al., (1997) "Synthesis of 3'-thioribonucleosides and their incorporation into oligoribonucleotides via phosphoramidite chemistry," RNA, 3(11 ):1352-63.

Tai, Wanyi, Bin Qin, and Kun Cheng. "Inhibition of breast cancer cell growth and invasiveness by dual silencing of HER-2 and VEGF." Molecular pharmaceutics 7.2 (2010): 543-556.

Xu, et al., "Delivery systems for siRNA drug development in cancer therapy", Asian Journal of Pharmaceutical Sciences, Aug. 28, 2014, vol. 10, No. 1, pp. 1-12.

Yoo et al., "Multivalent comb-type aptamer-siRNA conjugates for efficient and selective intracellular delivery", Chemical Communications, vol. 50, No. 51, May 8, 2014, pp. 6765-6767, XP055747253.

Office Action in Australian Patent Application 2016280709 dated Sep. 6, 2021, in 7 pages.

Office Action in Chinese Application 201680048179.5 dated Dec. 3, 2020, in 9 pages.

Office Action in Indian Application No. 201817001117 dated Aug. 17, 2021, in 10 pages.

Examiner Young, International Search Report and Written Opinion for International Application No. PCT/US2016/37685 dated Dec. 16, 2016, in 7 pages.

Examiner Young, International Preliminary Report on Patentability for International Application No. PCT/US2016/37685, dated Dec. 19, 2017, in 8 pages.

(56) References Cited

OTHER PUBLICATIONS

Partial Supplementary European Search Report for European Patent Application No. 16812366.9, dated Feb. 22, 2019, in 12 pages.
Extended Search Report for European Application No. 16812366.9, dated May 27, 2019, in 10 pages.
Office Action in Israel Application 256169 dated Mar. 9, 2021, in 15 pages.
International Search Report and Written Opinion for Application No. SG11201710143X, dated Jun. 3, 2019, in 8 pages.
Office Action in Japanese Application 2017-565893 dated Aug. 3, 2020, in 9 pages.
Japanese Patent Office, Notice of Reasons for Rejection, Application No. 2017-565893, dated Jul. 22, 2020, in 9 pages.
Office Action in Japanese Application 2017-565893 dated Jul. 5, 2021, in 7 pages.
Written Opinion for Application No. SG11201710143X, dated May 27, 2021, in 7 pages.
Kashihara et al, "Analysis of Renal Microcirculation and Permeability-Change with Bio-Imaging Techniques", KENBIKYO, 2011, vol. 46, No. 3, p. 181-187.
Motoyashi et al., "Glomerular Disease and tubule injury", Japanese Journal of Pediatric Nephrology, 2009, vol. 22, No. 2, p. 76-81.
Rinsho Yakuri, Japanese Journal of Clinical Pharmacology and Therapeutics, 2016, vol. 47, No. 2, p. 56-61.
First Office Action for European Application No. 16812366.9, dated Apr. 19, 2022, in 5 pages.
Office Action in Mexican Application MX/a/2017/016088 dated Apr. 26, 2022, in 9 pages.
International Search Report and Written Opinion for International Application No. PCT/US2016/037685, dated Dec. 16, 2016, in 12 pages.
Notice of Reasons for Rejection in Japanese Application 2019-542485 dated Feb. 24, 2022, in 10 pages.
Examination Report in Singapore Application No. 11201710143X, dated Nov. 25, 2022, in 5 pages.
European Search Report in Application No. 16812366.9, dated Nov. 18, 2022, in 4 pages.
Bonger, K. M., "Dimeric ligands for GPCRs involved in human reproduction: synthesis and biological evaluation" pp. 1-217, Dec. 19, 2008.
Cellamare et al., "Design, synthesis, and biological evaluation of glycine-based molecular tongs as inhibitors of AB1-40 aggregation in vitro", Bioorganic & Medicinal Chemistry, vol. 16, 2008, pp. 4810-4822.
Hong et al., "Gene Silencing by siRNA Microhydrogels via Polymeric Nanoscale Condensation", Aug. 2011, JAGS, 133: 13914-13917.
Zhang et al., "Synthesis and Biological Evaluation of Bivalent Ligands for the Cannabinoid 1 Receptor" Journal of Medicinal Chemistry, 53, pp. 7048-7060.

* cited by examiner

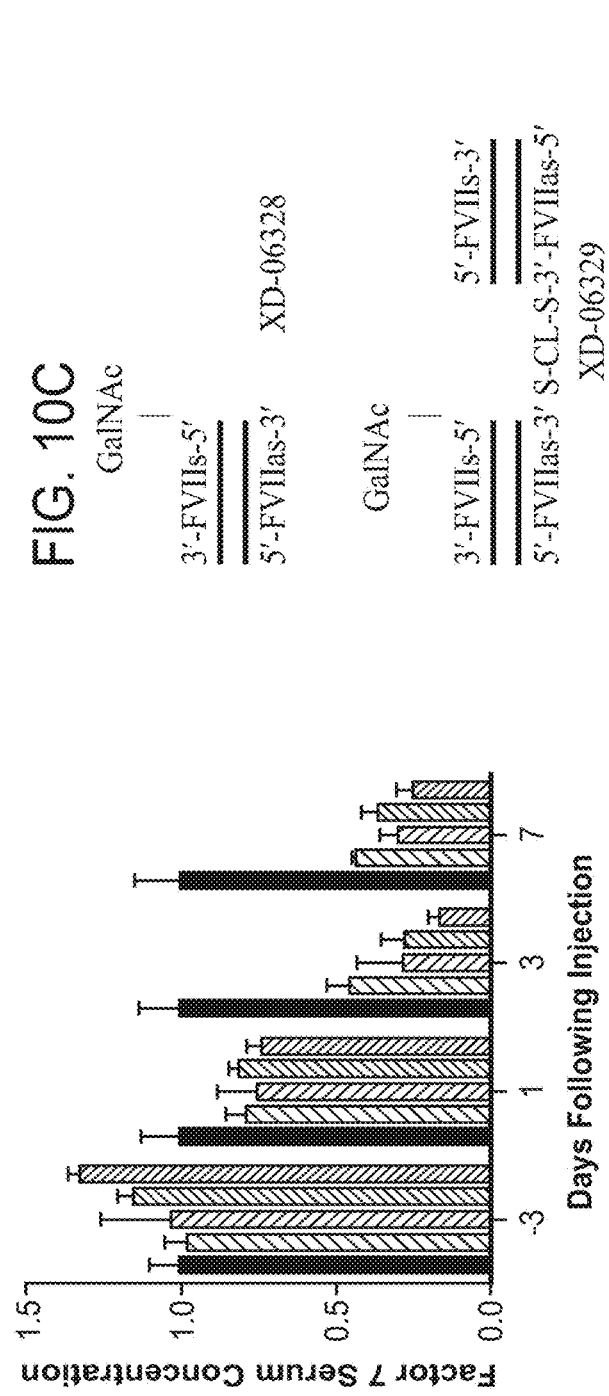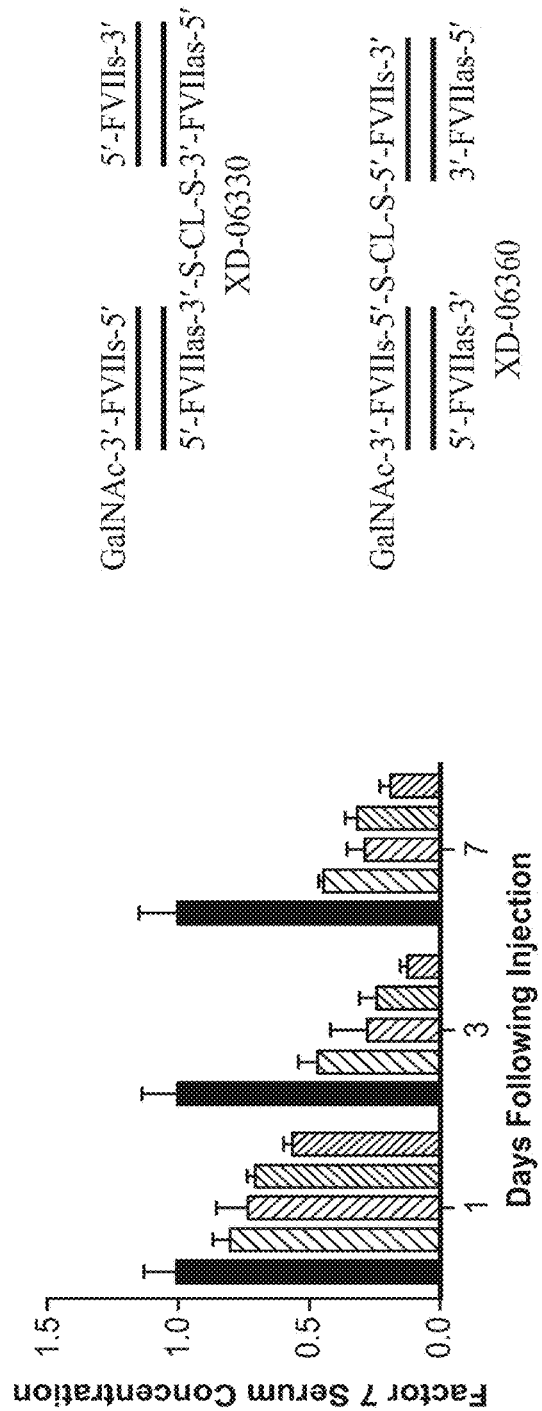

FIG. 11
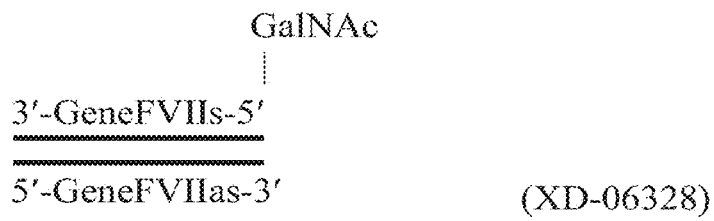
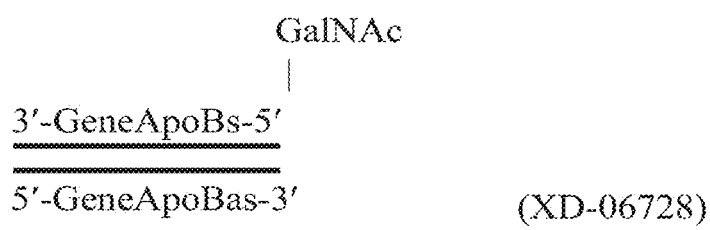
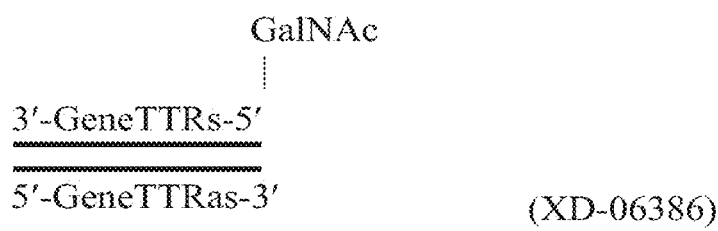
FIG. 12
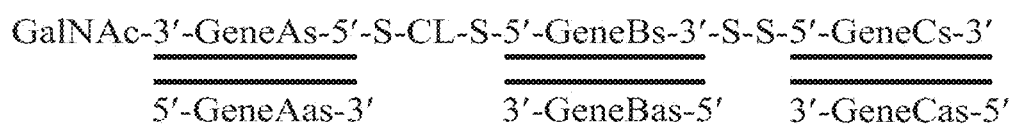

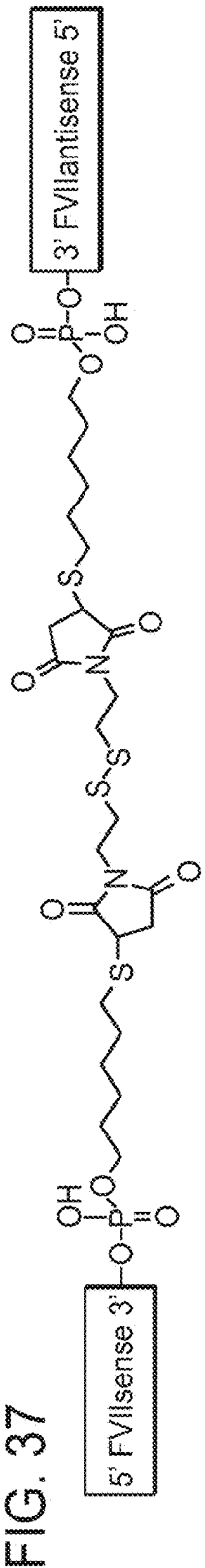

FIG. 37

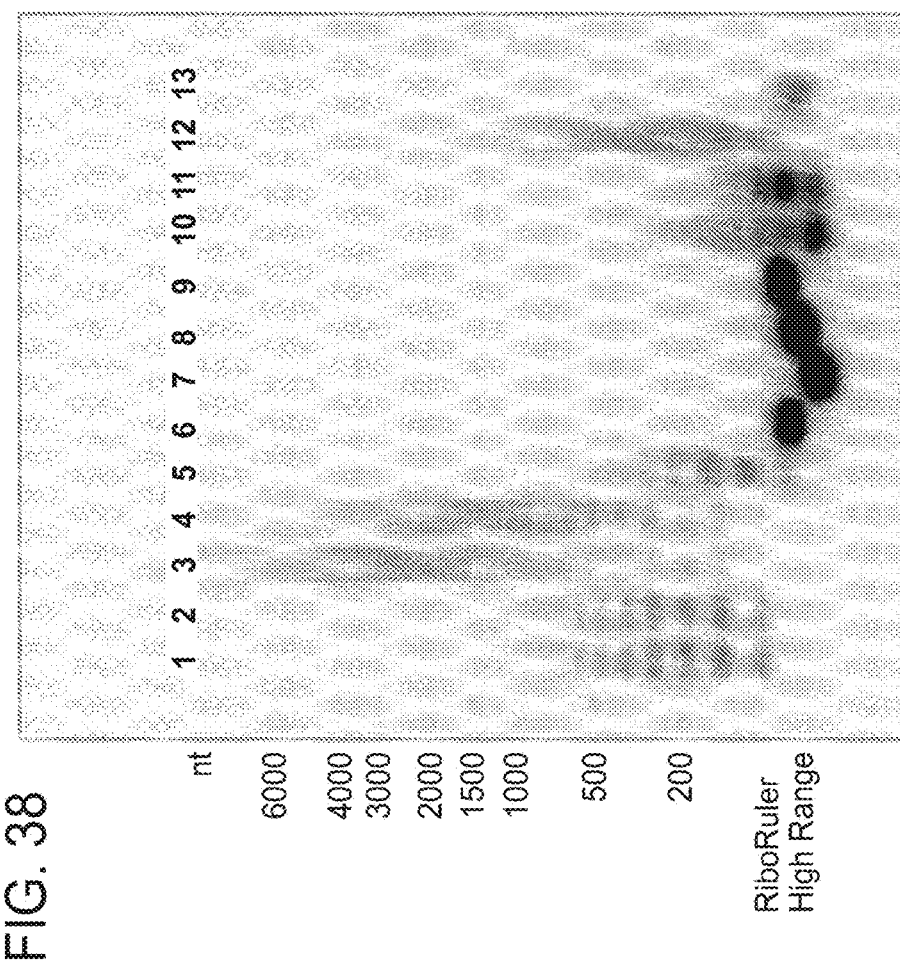

1. XD-05305 K1: „lane 6" non-cleavable
2. XD-05306 K1: „lane 6" cleavable
3. XD-05307 K1: s-c-s + as-nc-as
4. XD-05308 K1: s-nc-s + as-c-as
5. XD-05309 K1: ⑤tetrameric siRNA
6. XD-05310 K1: ⑥dimeric siRNA
7. XD-00376 K3: FVII canonical siRNA
8. XD-00194 K24: F-Luc canonical siRNA
9. XD-05311 K1: FVII-sense-c-ApoB-sense with FVII-antisense and ApoB-antisense
10. XD-05312 K1: FVII-sense-c-FVII antisense with FVII-sense and FVII-antisense (annealed@70°C)
11. XD-05312 K2: FVII-sense-c-FVII-antisense with FVII-sense and FVII-antisense (annealed@90°C)
12. X12714 K1: FVII heterodimer
13. X15049 K1: FVII/ApoB heterodimer 1.5μg/lane
2% agarose gel in 1xTAE
140mA 130min
Gel red staining (1:10000)

FIG. 38

DEFINED MULTI-CONJUGATES OLIGONUCLEOTIDES

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

SEQUENCE LISTING

The instant application contains a Sequence Listing which has been submitted electronically in ASCII format and is hereby incorporated by reference in its entirety. Said ASCII copy, created on Jul. 5, 2016, is named 116244-515_Sequence Listing.txt and is 41,267 bytes in size.

BACKGROUND OF THE INVENTION

Field of the Invention

The present invention relates to defined multi-conjugate oligonucleotides having predetermined sizes and compositions. For example, in various embodiment, the present invention relates to defined multi-conjugate oligonucleotides having advantageous properties, for example in the form of defined multi-conjugate siRNA (i.e., including two, three or more siRNA) having enhanced intracellular delivery and/or multi-gene silencing effects. In various embodiment, the present invention also relates to new synthetic intermediates and methods of synthesizing the defined multi-conjugate oligonucleotides. The present invention also related to methods of using the defined multi-conjugate oligonucleotides, for example in reducing gene expression, biological research, treating or preventing medical conditions, or to produce new or altered phenotypes in cells or organisms.

Description of the Related Art

Currently there are a number of new therapeutic and bioengineering modalities involving the delivery of biologically active molecules such as small interfering RNA (siRNA) and microRNA (miRNA), to name a few, across cell membranes and cell walls to produce biological effects within the cell, such as, in the case of siRNA and miRNA, to suppress protein production. Other techniques and/or biologically active molecules delivered into the cell have the effect of enhancing gene expression and protein production.

However, RNA and other oligonucleotides in their native state are labile in vivo and easily decomposed within a short period of time. Furthermore, many of them, like RNA, are anionic which makes cell membrane transmission difficult, resulting in low intracellular delivery efficiency.

Taking siRNA as an example, efforts to increase its delivery efficiency include preparation of a nano-sized ionic complex through ionic bonding of siRNA and diverse cationic carrier materials such as cationic polymers, lipids or peptides. Jeong et al., Bioconjugate Chem, 20(1):5-14 (2009). However, there are challenges associated with the preparation of a stable siRNA/cationic carrier complex.

Other efforts to increase delivery efficiency of oligonucleotides such as siRNA include conjugation of the oligonucleotide to a specific cell targeting moiety. E.g., Nair et al., "Mulivalent N-Acetylgalactosamine-Conjugated siRNA Localizes in Hepatocytes and Elicits Robust RNAi-Mediated Gene Silencing," J Am Chem Soc, 136 (49):16958-16961 (2014).

However, these and other prior art approaches do not solve the problems of oligonucleotide delivery. Accordingly, there remains a need for improved oligonucleotide compositions.

SUMMARY OF THE INVENTION

The present invention relates to defined multi-conjugate oligonucleotides having predetermined sizes and compositions. The present invention also relates to methods of using the defined multi-conjugate oligonucleotides. The present invention also relates to methods of synthesizing the defined multi-conjugate oligonucleotides, as well as new intermediate compounds used in the synthesis of the defined multi-conjugate oligonucleotides.

Accordingly, the present invention provides RNA and/or DNA multi-conjugates having predetermined sizes and compositions, improved charge density, improved delivery, and/or improved efficacy (e.g., as compared to the same moieties in their unconjugated state). When the multi-conjugates are complexed with a suitable carrier and/or conjugated to another chemical or biological moiety such as a cell-targeting ligand, they can be delivered with greater efficiency and safety across a cell membrane or cell wall for enhanced biological or therapeutic effects.

Accordingly, advantages of the defined multi-conjugate oligonucleotides of the present invention can include: increasing oligonucleotide delivery to a cell (e.g., delivering more oligonucleotide per cell targeting ligand binding event), the ability to deliver a predetermined stoichiometric ratio of different oligonucleotides to a cell (e.g., 1:1:1 in the case of a trimeric multi-conjugate comprising three different oligonucleotides), and/or the ability to deliver a combination of therapeutic oligonucleotides as a single chemical entity (e.g., a trimeric multi-conjugate comprising three different oligonucleotides is one molecule) thus simplifying their use and regulatory review.

The invention is also based, at least in part, upon the development of new synthetic methodology and intermediates, which allow the preparation of the defined multi-conjugate oligonucleotides having predetermined sizes and compositions.

In various aspects, the invention provides an oligonucleotide coupled to a covalent linker, which can be used, for example, in the synthesis of defined multi-conjugate oligonucleotides having predetermined sizes and compositions.

In one aspect, the invention provides a compound according to Structure 1:

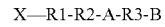 (Structure 1)

wherein:
X is a nucleic acid bonded to R1 through its 3' or 5' terminus;
R1 a phosphodiester, thiophosphodiester, sulfate, amide, glycol, or is absent;
R2 is a C2-C10 alkyl, alkoxy, or aryl group, or is absent;
A is the reaction product of a nucleophile and an electrophile;
R3 is a C2-C10 alkyl, alkoxy, aryl, alkyldithio group, ether, thioether, thiopropionate,
or disulfide; and
B is a nucleophile or electrophile.

In one aspect, the invention provides a compound according to Structure 2:

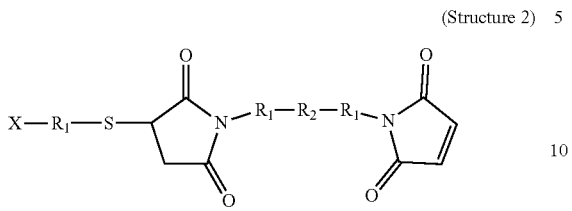
(Structure 2)

wherein:
X is a nucleic acid bonded to R1 via a phosphate or thiophosphate at its 3' or 5' terminus;
each R1 is independently a C2-C10 alkyl, alkoxy, or aryl group; and
R2 is a thiopropionate or disulfide group.

In one aspect, the invention provides a compound according to Structure 3:

X—R1-R2-A-R3-B    (Structure 3)

wherein:
X is a nucleic acid bonded to R1 through its 3' or 5' terminus;
R1 a phosphate, thiophosphate, sulfate, amide, glycol, or is absent;
R2 is a C2-C10 alkyl, alkoxy, or aryl group, or is absent;
A is the reaction product of a first and a second reactive moiety;
R3 is an C2-C10 alkyl, alkoxy, aryl, alkoxy, alkyldithio group, ether, thioether, thiopropionate, or disulfide; and
B is a third reactive moiety.

In various aspects, the invention provides methods for synthesizing an oligonucleotide coupled to a covalent linker.

In one aspect, the invention provides a method for synthesizing a compound according to Structure 1 (or adapted for synthesizing a compounds according to Structure 2 or 3), the method comprising:
reacting a functionalized nucleic acid X—R1-R2-A' and a covalent linker A"-R3-B, wherein A' and A" comprise a nucleophile and an electrophile, in a dilute solution of X—R1-R2-A' and with a stoichiometric excess of A"-R3-B, thereby forming the compound X—R1-R2-A-R3-B (Structure 1)
wherein:
X is a nucleic acid bonded to R1 through its 3' or 5' terminus;
R1 a phosphodiester, thiophosphodiester, sulfate, amide, glycol, or is absent;
R2 is a C2-C10 alkyl, alkoxy, or aryl group, or is absent;
A is the reaction product of a nucleophile and an electrophile;
R3 is a C2-C10 alkyl, alkoxy, aryl, alkyldithio group, ether, thioether, thiopropionate, or disulfide; and
B is a nucleophile or electrophile.

The method can further comprise the step of synthesizing the functionalized nucleic acid X—R1-R2-A', wherein A' comprises a thiol (—SH) by (i) introducing a the thiol during solid phase synthesis of the nucleic acid using phosphoramidite oligomerization chemistry or (ii) reduction of a disulfide introduced during the solid phase synthesis.

In various aspects, the invention provides dimeric defined multi-conjugate oligonucleotides.

In one aspect, the invention provides an isolated compound according to Structure 4:

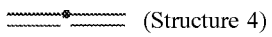 (Structure 4)

wherein:
each  is a double stranded oligonucleotide designed to react with the same molecular target in vivo, and
• is a covalent linker joining single strands of adjacent single stranded oligonucleotides at their 3' or 5' termini, and having the structure —R1-R2-A-R3-A-R2-R1-
wherein:
each R1 is independently a phosphodiester, thiophosphodiester, sulfate, amide, glycol, or is absent;
each R2 is independently a C2-C10 alkyl, alkoxy, or aryl group, or is absent;
each A is independently the reaction product of a nucleophile and an electrophile, and
R3 is a C2-C10 alkyl, alkoxy, aryl, alkoxy, alkyldithio group, ether, thioether, thiopropionate, or disulfide.

In one aspect, the invention provides an isolated compound according to Structure 5:

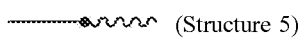 (Structure 5)

wherein:
——— is a first single stranded oligonucleotide
∿∿∿ is a second single stranded oligonucleotide having a different sequence from the first, and
• is a covalent linker joining single strands of adjacent single stranded oligonucleotides at their 3' or 5' termini, and having the structure —R1-R2-A-R3-A-R2-R1-
wherein:
each R1 is independently a phosphate, sulfate, amide, glycol, or is absent;
each R2 is independently a C2-C10 alkyl, alkoxy, or aryl group, or is absent;
each A is independently the reaction product of a thiol and maleimide, a thiol and vinylsulfone, a thiol and pyridyldisulfide, a thiol and iodoacetamide, a thiol and acrylate, an azide and alkyne, or an amine and carboxyl group, and
R3 is an C2-C10 alkyl, alkoxy, aryl, alkoxy, alkyldithio group, ether, thioether, thiopropionate, or disulfide.

In one aspect, the invention provides an isolated compound according to Structure 6:

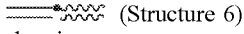 (Structure 6)

wherein:
——— is a first double stranded oligonucleotide
∿∿∿ is a second double stranded oligonucleotide having a different sequence from the first, and
• is a covalent linker joining single strands of adjacent single stranded oligonucleotides at their 3' or 5' termini, and having the structure —R1-R2-A-R3-A-R2-R1-
wherein:
each R1 is independently a phosphate, sulfate, amide, glycol, or is absent;
each R2 is independently a C2-C10 alkyl, alkoxy, or aryl group, or is absent;
each A is independently the reaction product of a thiol and maleimide, a thiol and vinylsulfone, a thiol and pyridyldisulfide, a thiol and iodoacetamide, a thiol and acrylate, an azide and alkyne, or an amine and carboxyl group, and
R3 is an C2-C10 alkyl, alkoxy, aryl, alkoxy, alkyldithio group, ether, thioether, thiopropionate, or disulfide.

In one aspect, the invention provides an isolated compound according to Structure 11:

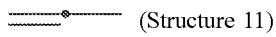 (Structure 11)

───── is a double stranded oligonucleotide,

───── is a single stranded oligonucleotide, and

• is a covalent linker joining single strands of adjacent single stranded oligonucleotides.

In various aspects, the invention provides methods for synthesizing dimeric defined multi-conjugate oligonucleotides.

In one aspect, the invention provides a method for synthesizing a compound of Structure 5:

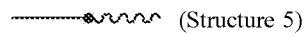 (Structure 5)

wherein ───── is a first single stranded oligonucleotide, ∿∿∿∿ is a second single stranded oligonucleotide having a different sequence from the first, and • is a covalent linker joining single strands of adjacent single stranded oligonucleotides at their 3' or 5' termini, the method comprising the steps of:

(i) reacting a first single stranded oligonucleotide ───── $R_1$ with a bifunctional linking moiety ○, wherein R1 is a chemical group capable of reacting with ○ under conditions that produce the mono-substituted product ─────○; ;

(ii) reacting ─────○; with a second single stranded oligonucleotide ∿∿∿∿ $R_2$, wherein R2 is a chemical group capable of reacting with ○, thereby forming ─────•∿∿∿∿ .

The method can further comprise the step of annealing complementary ───── and ∿∿∿∿ to yield Structure 6:

In one aspect, the invention provides a method for synthesizing an isolated compound of Structure 4:

─────•───── (Structure 4)

wherein each ───── is a double stranded oligonucleotide and • is a covalent linker joining single strands of adjacent single stranded oligonucleotides at their 3' or 5' termini, the method comprising the steps of:

(i) reacting a first single stranded oligonucleotide ───── $R_1$ with a bifunctional linking moiety ○, wherein R1 is a chemical group capable of reacting with ○, thereby forming a monosubstituted product ─────○; ;

(ii) reacting ─────○; with a second single stranded oligonucleotide ───── $R_2$, wherein R2 is a chemical group capable of reacting with ○, thereby forming a single stranded dimer ─────•───── ;

(iii) annealing single stranded oligonucleotides, at the same time or sequentially, thereby forming ─────•───── .

In one aspect, the invention provides a method for synthesizing an isolated compound of Structure 4:

─────•───── (Structure 4) wherein each ───── is a double stranded oligonucleotide and • is a covalent linker joining single strands of adjacent single stranded oligonucleotides at their 3' or 5' termini, the method comprising the steps of:

(i) forming ─────•───── by:

(a) annealing a first single stranded oligonucleotide ───── and a second single stranded oligonucleotide ───── $R_1$, thereby forming ═════ $R_1$, and reacting ═════ R with a third single stranded oligonucleotide ───── $R_2$, wherein R1 and R2 are chemical moieties capable of reacting directly or indirectly to form a covalent linker •, thereby forming ═════•───── ; or (b) reacting the second single stranded oligonucleotide ───── $R_1$ and the third single stranded oligonucleotide ───── $R_2$, thereby forming ─────•───── , and annealing the first single stranded oligonucleotide ───── and ─────•───── thereby forming ═════•───── ;

(ii) annealing ═════•───── and a fourth single stranded oligonucleotide ───── thereby forming ═════•═════ .

In one aspect, the invention provides a method for synthesizing an isolated compound of Structure 4:

─────•───── (Structure 4) wherein each ═════ is a double stranded oligonucleotide and • is a covalent linker joining single strands of adjacent single stranded oligonucleotides at their 3' or 5' termini, the method comprising the steps of:

(a) annealing a first single stranded oligonucleotide ───── and a second single stranded oligonucleotide ───── $R_1$, thereby forming ═════ $R_1$;

(b) annealing a third single stranded oligonucleotide ───── $R_2$ and a fourth single stranded oligonucleotide ─────, thereby forming ═════ $R_2$;

(b) reacting ═════ $R_1$ and ═════ $R_2$ with wherein R1 and R2 ───── $R_2$, wherein R1 and R2 are chemical moieties capable of reacting directly or indirectly to form a covalent linker •, thereby forming ═════•═════ .

In various aspects, the invention provides multimeric (n>2) defined multi-conjugate oligonucleotides, including defined tri-conjugates and defined tetraconjugates.

In one aspect, the invention provides a compound according to Structure 7 or 8:

 (Structure 7)

 (Structure 8)

wherein:

each ───── is a double stranded oligonucleotide, each • is a covalent linker joining single strands of adjacent single stranded oligonucleotides, and m is an integer ≥1 and n is an integer ≥0.

In one aspect, the invention provides a compound according to Structure 9 and wherein n=0; ═════•═════ (Structure 9). In one aspect, the invention provides a compound according to Structure 10 and wherein m=1: ═════•═════•═════ (Structure 10).

In one aspect, the invention provides a compound according to Structure 12, 13, 14, or 15:

 (Structure 12)

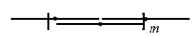 (Structure 13)

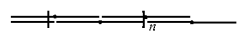 (Structure 14)

-continued

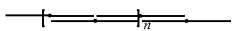 (Structure 15)

wherein:
each ═══ is a double stranded oligonucleotide,
each ─── is a single stranded oligonucleotide,
each • is a covalent linker joining single strands of adjacent single stranded oligonucleotides, and
m is an integer ≥1 and n is an integer ≥0.

In various aspects, the invention provides methods for synthesizing multimeric (n>2) defined multi-conjugate oligonucleotides, including defined tri-conjugates and defined tetraconjugates.

In one aspect, the invention provides a method for synthesizing a compound according to Structure 7 or 8:

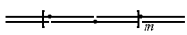 (Structure 7)

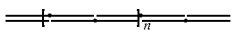 (Structure 8)

wherein: each ═══ is a double stranded oligonucleotide, each • is a covalent linker joining single strands of adjacent single stranded oligonucleotides, and m is an integer ≥1 and n is an integer ≥0, the method comprising the steps of:
(i) forming ═══•─── by:
  (a) annealing a first single stranded oligonucleotide ─── and a second single stranded oligonucleotide ─── $R_1$, thereby forming ═══ $R_1$, and reacting ═══ $R_1$ with a third single stranded oligonucleotide ─── $R_1$, wherein R1 and R2 are chemical moieties capable of reacting directly or indirectly to form a covalent linker •, thereby forming ═══•─── ; or
  (b) reacting the second single stranded oligonucleotide ─── $R_1$ and the third single stranded oligonucleotide ─── $R_2$, thereby forming ───•─── and annealing the first single stranded oligonucleotide ─── and ───•─── thereby forming ═══•─── ;
(ii) annealing ═══•─── and a second single stranded dimer ───•───, thereby forming ═══•═══•─── and, optionally, annealing one or more additional single stranded dimers ───•─── to ═══•═══•─── thereby forming

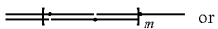 or

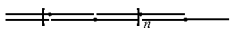

wherein m is an integer ≥1 and n is an integer ≥0; and
(iii) annealing a fourth single stranded oligonucleotide ─── to the product of step
(ii), thereby forming structure 7 or 8.

In one aspect, the invention provides a method for synthesizing a compound according to Structure 7 or 8:

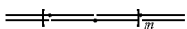 (Structure 7)

-continued

 (Structure 8)

wherein: each ═══ is a double stranded oligonucleotide, each • is a covalent linker joining single strands of adjacent single stranded oligonucleotides, and m is an integer ≥1 and n is an integer ≥0, the method comprising the steps of:
(i) annealing a first single stranded oligonucleotide ─── and a first single stranded dimer ───•───, thereby forming ═══•─── ;
(ii) annealing ═══•─── and a second single stranded dimer ───•─── thereby forming ═══•═══•─── and, optionally, annealing one or more additional single stranded dimers ───•─── to ═══•═══•─── thereby forming,

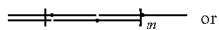 or

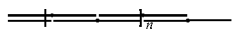

wherein m is an integer ≥1 and n is an integer ≥0; and
(iii) annealing a second single stranded oligonucleotide ─── to the product of step
(ii), thereby forming structure 7 or 8.

In one aspect, the invention provides a method for synthesizing a compound of Structure 9: ═══•═══•═══ (Structure 9), wherein each ═══ is a double stranded oligonucleotide, each • is a covalent linker joining single strands of adjacent single stranded oligonucleotides, the method comprising the steps of:
(i) forming ═══•─── by:
  (a) annealing a first single stranded oligonucleotide ─── and a second single stranded oligonucleotide ─── $R_1$, thereby forming ═══ $R_1$, and reacting ═══ $R_1$ with a third single stranded oligonucleotide ─── $R_2$, wherein R1 and R2 are chemical moieties capable of reacting directly or indirectly to form a covalent linker •, thereby forming ═══•─── ; or
  (b) reacting the second single stranded oligonucleotide ─── $R_1$ and the third single stranded oligonucleotide ─── $R_2$, thereby forming ───•───, and annealing the first single stranded oligonucleotide ─── and ───•─── thereby forming ═══•─── ;
(ii) annealing ═══•─── and a single stranded dimer ───•───, thereby forming ═══•═══•─── ; and
(iii) annealing ═══•═══•─── and a fourth single stranded oligonucleotide ───, thereby forming ═══•═══•═══ .

In one aspect, the invention provides a method for synthesizing a compound of Structure 10: ═══•═══•═══•═══ (Structure 10), wherein each ═══ is a double stranded oligonucleotide, each • is a covalent linker joining single strands of adjacent single stranded oligonucleotides, the method comprising the steps of:
(i) forming ═══•─── by:
  (a) annealing a first single stranded oligonucleotide ─── and a second single stranded oligonucleotide ─── $R_1$, thereby forming ═══ $R_1$, and reacting ═══ $R_1$ with a third single stranded oligonucleotide ─── $R_2$, wherein R1 and R2 are chemical moieties capable of reacting directly or indirectly to form a covalent linker •, thereby forming ═══•─── ; or (b) reacting the second single stranded oligonucleotide ----- R₁ and the third single stranded oligonucleotide ----- R₂, thereby forming —•—, and annealing the first single stranded oligonucleotide ----- and —•—, thereby forming ═•═ ;

(ii) annealing ═•═ and a single stranded dimer —•—, thereby forming ═•═•═ .

(iii) annealing ═•═•═ and a second single stranded dimer —•—, thereby forming ═•═•═•═ ; and (iv) annealing ═•═•═ and a fourth single stranded oligonucleotide -----, thereby forming ═•═•═•═ .

In various aspects, the invention provides sense-antisense multi-conjugate oligonucleotides, as well as methods for their synthesis.

In one aspect, the invention provides a composition comprising a plurality of molecules, each molecule having Structure 16:

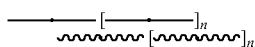 (Structure 16), wherein n is an integer ≥1;
each ----- is a single stranded oligonucleotide;
each ∿∿∿ is a single stranded oligonucleotide that hybridizes with a ----- .
═ is a double stranded oligonucleotide; and
each • is a covalent linker joining single strands of adjacent single stranded oligonucleotides.

In one aspect, the invention provides a method for synthesizing composition comprising a plurality of molecules, each molecule having Structure 16, the methods comprising:

(i) reacting a first single stranded oligonucleotide ----- R₁ with a bifunctional linking moiety ○, wherein R1 is a chemical group capable of reacting with ○ a under conditions that produce the monosubstituted product -----○ ; ;

(ii) reacting -----○ with a second single stranded oligonucleotide ∿∿∿ R₂, wherein R2 is a chemical group capable of reacting with ○, thereby forming -----●∿∿∿ ;

(iii) annealing a plurality of -----●∿∿∿ thereby forming a composition comprising a plurality of molecules, each molecule having Structure 16.

In various aspects, the invention provides methods for synthesizing multi-conjugate oligonucleotides.

In one aspect, the invention provides method for synthesizing a composition comprising a plurality of molecule comprising Structure 17:

─────•[─────]ₙ
∿∿∿∿[∿∿∿∿]ₙ

(Structure 17), wherein n is an integer ≥1; each ----- is a single stranded oligonucleotide; each ∿∿∿ is a single stranded oligonucleotide that hybridizes with a ----- ; ═ is a double stranded oligonucleotide; and each • is a covalent linker joining single strands of adjacent single stranded oligonucleotides to form —•— and ∿∿∿∿, the method comprising the steps of:
annealing a plurality of —•— and ∿∿∿∿ at:
(i) a total oligonucleotide concentration of about 200-300 µM for —•— and ∿∿∿∿,
(ii) about 0.1-0.3× phosphate buffered saline (PBS), and
(iii) at a temperature of about 70-80° C. to about 20-30° C. for about 1.5-2.5 hours.

In various aspects, the invention provides pharmaceutical compositions comprising multi-conjugate oligonucleotides.

In one aspect, the invention provides a composition (e.g., pharmaceutical composition) comprising (i) a compound or composition according to the invention and (ii) a pharmaceutically acceptable excipient.

In one aspect, the invention provides a compound or composition according to the invention for use a medicament, or for use in the manufacture of a medicament. The medicament can be for silencing or reducing the expression of at least one overexpressed gene, for example for silencing or reducing the expression of two, three, four, or more overexpressed genes.

In one aspect, the invention provides a composition (e.g., pharmaceutical composition) comprising a compound or composition according to the invention, formulated in lipid nanoparticles (LNP), exosomes, microvesicles, or viral vectors.

In various aspects, the invention provides methods for using multi-conjugate oligonucleotides.

In one aspect, the invention provides a method for reducing gene expression comprising administering an effective amount of a compound or composition according to the invention to a subject in need thereof.

In one aspect, the invention provides a method for treating a subject comprising administering an effective amount of a compound or composition according to the invention to a subject in need thereof.

In one aspect, the invention provides a method for silencing two or more genes comprising administering an effective amount of a compound or composition according to the invention to a subject in need thereof, wherein the compound or composition comprises oligonucleotides targeting two or more genes. The compound or composition can comprise oligonucleotides targeting two, three, four, or more genes.

In one aspect, the invention provides a method for delivering two or more oligonucleotides to a cell per targeting ligand binding event comprising administering an effective amount of a compound or composition according to the invention to a subject in need thereof, wherein the compound or composition comprises a targeting ligand.

In one aspect, the invention provides a method for delivering a predetermined stoichiometric ratio of two or more oligonucleotides to a cell comprising administering an effective amount of a compound or composition according to the invention to a subject in need thereof, wherein the compound or composition comprises the predetermined stoichiometric ratio of two or more oligonucleotides.

In various aspects, the invention provides oligonucleotides having a specific sequence.

In one aspect, the invention provides an siRNA having SEQ ID NO: 106.

In one aspect, the invention provides an siRNA having SEQ ID NO: 115.

One skilled in the art will recognize that the aspects above can be combined with one or more suitable features described below.

In various embodiments, a covalent linker (e.g., one or all of •) can comprise the reaction product of a nucleophile and electrophile. For example, a covalent linker (e.g., one or all of •) can comprise the reaction product of a thiol and maleimide, a thiol and vinylsulfone, a thiol and pyridyldisulfide, a thiol and iodoacetamide, a thiol and acrylate, an azide and alkyne, or an amine and carboxyl group. In various embodiments, covalent linkers are not oligonucleotides.

In various embodiments, the nucleophile and electrophile (e.g., of A in Structure 1 or 4-6) can comprise a thiol and maleimide, a thiol and vinylsulfone, a thiol and pyridyldisulfide, a thiol and iodoacetamide, a thiol and acrylate, an azide and alkyne, or an amine and carboxyl group. Similarly, the reactive moieties in Structure 3 can comprise a nucleophile and electrophile, for example a thiol and maleimide, a thiol and vinylsulfone, a thiol and pyridyldisulfide, a thiol and iodoacetamide, a thiol and acrylate, an azide and alkyne, or an amine and carboxyl group.

In various embodiments, the nucleophile or electrophile (e.g., of B in Structure 1) can comprise a thiol, maleimide, vinylsulfone, pyridyldisulfide, iodoacetamide, acrylate, azide, alkyne, amine, or carboxyl group.

In various embodiments, a linker (e.g., • or the linkers shown in Structures 1-3) can comprise the reaction product of a DTME (dithiobismaleimidoethane), BM(PEG)2 (1,8-bis(maleimido)diethylene glycol), BM(PEG)3 (1,11-bismaleimido-triethyleneglycol), BMOE (bismaleimidoethane), BMH (bismaleimidohexane), or BMB (1,4-bismaleimidobutane). For example, the linker • can comprise the reaction product of a thiol and DTME (dithiobismaleimidoethane), BM(PEG)2 (1,8-bis(maleimido)diethylene glycol), BM(PEG)3 (1,11-bismaleimido-triethyleneglycol), BMOE (bismaleimidoethane), BMH (bismaleimidohexane), or BMB (1,4-bismaleimidobutane).

In various embodiments comprising two or more covalent linkers • (e.g., in Structures 7-16), the linkers are all the same. Alternatively, the compound or composition can comprise two or more different covalent linkers •.

In various embodiments, in Structure 1,
R1 is a phosphodiester or thiophosphodiester;
R2 is a C2-C10 alkyl;
A is the reaction product of a thiol and maleimide;
R3 is a disulfide; and
B is a thiol or maleimide.

In various embodiments, the nucleic acid (e.g., X) or oligonucleotide (e.g., —, ⁓, ═, ⁂, or ≈) is RNA, DNA, or comprises an artificial or non-natural nucleic acid analog.

In various embodiments, the nucleic acid or oligonucleotide is DNA, for example an antisense DNA (aDNA) or antisense gapmer.

In various embodiments, the nucleic acid or oligonucleotide is RNA, for example an antisense RNA (aRNA), CRISPR RNA (crRNA), long noncoding RNA (lncRNA), microRNA (miRNA), piwi-interacting RNA (piRNA), small interfering RNA (siRNA), messenger RNA (mRNA), short hairpin RNA (shRNA), small activating (saRNA), antagomir, or ribozyme. In one embodiment, the RNA is siRNA.

In various embodiments, the nucleic acid or oligonucleotide is an aptamer.

In various embodiments, the nucleic acid or oligonucleotide further comprises a chemical modification. The chemical modification can comprise a modified nucleoside, modified backbone, modified sugar, or modified terminus.

In various embodiments, the nucleic acid or oligonucleotide further comprises a targeting ligand. The targeting ligand can be bound (e.g., directly) to the nucleic acid, for example through its 3' or 5' terminus. In one embodiment, the targeting ligand comprises N-Acetylgalactosamine (GalNAc), cholesterol, tocopherol, folate, 2-[3-(1,3-dicarboxypropyl)ureido]pentanedioic acid (DUPA), or anisamide.

In various embodiment, the method can include coupling a targeting ligand to the molecule.

In various embodiments, the nucleic acid or oligonucleotide is single stranded.

In various embodiments, the nucleic acid or oligonucleotide is double stranded.

In various embodiments, the nucleic acid or oligonucleotide is 15-30, 17-27, 19-26, 20-25, 40-50, 40-150, 100-300, 1000-2000, or up to 10000 nucleotides in length.

In various embodiments, the nucleic acid or oligonucleotide is connected to the linker via a phosphodiester or thiophosphodiester (e.g., R1 in Structure 1 is a phosphodiester or thiophosphodiester).

In various embodiments, the nucleic acid or oligonucleotide is connected to the linker via a C2-C10, C3-C6, or C6 alkyl (e.g., R2 in Structure 1 is a C2-C10, C3-C6, or C6 alkyl).

In various embodiments, the nucleic acid or oligonucleotide is connected to the linker via the reaction product of a thiol and maleimide group. (e.g., A in Structure 1 is the reaction product of a thiol and maleimide group).

In various embodiments, the linker (e.g., •, R3 in Structure 1, R1-R2-R1 in Structure 2, or A-R3-B in Structure 3) is cleavable. In one embodiment, the cleavable covalent linker comprises an acid cleavable ester bond, hydrazine bond, or acetal bond. In one embodiment, the cleavable covalent linker comprises a reductant cleavable bond. In one embodiment, the reductant cleavable bond is a disulfide bond. In one embodiment, the cleavable covalent linker is cleavable under intracellular conditions. In one embodiment, the cleavable covalent linker comprises a biocleavable bond. In one embodiment, the cleavable covalent linker comprises an enzyme cleavable bond.

In various embodiments, the linker is not cleavable. In one embodiment, one or more of • comprises a noncleavable covalent linker. In one embodiment, the noncleavable covalent linker comprises an amide bond or urethane bond. A noncleavable covalent linker can be an alkyl, aryl, or similar hydrocarbon group.

In various embodiments, the linker comprises a thiopropionate or disulfide (e.g., R3 is a thiopropionate or disulfide).

In various embodiments, the moiety

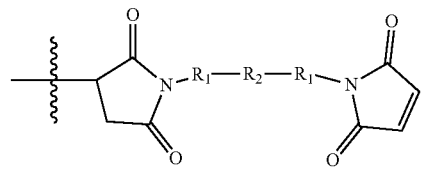

in Structure 2 comprises the reaction product of a DTME (dithiobismaleimidoethane), BM(PEG)2 (1,8-bis(maleimido)diethylene glycol), BM(PEG)3 (1,11-bismaleimidotriethyleneglycol), BMOE (bismaleimidoethane), BMH (bismaleimidohexane), or BMB (1,4-bismaleimidobutane).

In various embodiments, the linker is a homo bifunctional linker. For example, in one embodiment B comprises one of the same groups as A in Structure 1 or Structure 3.

In various embodiments, the linker is a hetero bifunctional linker. For example, in one embodiment B comprises a different group from A in Structure 1 or Structure 3.

In various embodiments, the compound is isolated or substantially pure. For example, the compound can be at least 75, 80, 85, 90, 95, 96, 97, 98, 99, or 100% pure. In one embodiment, the compound is about 85-95% pure. Likewise, the methods for synthesizing the compounds and compositions according to the invention can result in a product that is at least 75, 80, 85, 90, 95, 96, 97, 98, 99, or 100% pure. In one embodiment, the product is about 85-95% pure.

In various embodiments, each double stranded oligonucleotide is an siRNA and/or has a length of 15-30 base pairs.

In various embodiments, each ──•── may independently comprise two sense or two antisense oligonucleotides.

In various embodiments, each ──•── may independently comprise one sense and one antisense oligonucleotide.

In various embodiments, the compound or composition comprises a homomultimer of substantially identical double stranded oligonucleotides. The substantially identical double stranded oligonucleotides can each comprise an siRNA targeting the same molecular target in vivo.

In various embodiments, the compound or composition comprises a hetero-multimer of two or more substantially different double stranded oligonucleotides. The substantially different double stranded oligonucleotides can each comprise an siRNA targeting different genes.

In various embodiments the compound comprises Structure 9 and wherein n=0: ═══•═══•═══ (Structure 9). The compound can further comprise a targeting ligand. The compound can further comprise 2 or 3 substantially different double stranded oligonucleotides ═══════ each comprising an siRNA targeting a different molecular target in vivo. The compound can further comprise a targeting ligand, one ═══════ comprising a first siRNA guide strand targeting Factor VII and a first passenger strand hybridized to the guide strand, one ═══════ comprising a second siRNA guide strand targeting Apolipoprotein B and a second passenger strand hybridized to the second guide strand, and one ═══════ comprising a third siRNA guide strand targeting TTR and a third passenger strand hybridized to the third guide strand. The targeting ligand can comprise N-Acetylgalactosamine (GalNAc).

In various embodiments, the compound comprises Structure 10 and wherein m=1: ═══•═══•═══ (Structure 10). The compound can further comprise a targeting ligand. The compound can further comprise 2, 3, or 4 substantially different double stranded oligonucleotides ═══════ each comprising an siRNA targeting a different molecular target in vivo. The compound can further comprise a targeting ligand, one ═══════ comprising a first siRNA guide strand targeting Factor VII and a first passenger strand hybridized to the guide strand, one ═══════ comprising a second siRNA guide strand targeting Apolipoprotein B and a second passenger strand hybridized to the second guide strand, and one ═══════ comprising a third siRNA guide strand targeting TTR and a third passenger strand hybridized to the third guide strand. The targeting ligand can comprise N-Acetylgalactosamine (GalNAc).

In various embodiments relating to Structure 16, each, ══ has a length of 15-30 base pairs; each ══ is an siRNA; and/or n is an integer from 1 to 100.

In various embodiments, each double stranded oligonucleotide (e.g., ═══════ for example in Structure 4) comprises an siRNA guide strand targeting Factor VII and a passenger strand hybridized to the guide strand.

In various embodiments (e.g., in Structure 4), the compound further comprises a targeting ligand, each double stranded oligonucleotide (e.g., ═══════ ) comprises an siRNA guide strand and a passenger strand hybridized to the guide strand, and the compound is at least 75, 80, 85, 90, 95, 96, 97, 98, 99, or 100% pure.

In various embodiments, at least one double stranded oligonucleotide (e.g., ═══════ , for example in Structure 6) comprises a first siRNA guide strand targeting Factor VII and a first passenger strand hybridized to the guide strand, and at least one double stranded oligonucleotide (e.g., ∿∿∿ , for example in Structure 6) comprises a second siRNA guide strand targeting Apolipoprotein B and a second passenger strand hybridized the second guide strand.

In various embodiments, the method for synthesizing the compound of Structure 1 further comprises synthesizing the compound of Structure 2:

(Structure 2)

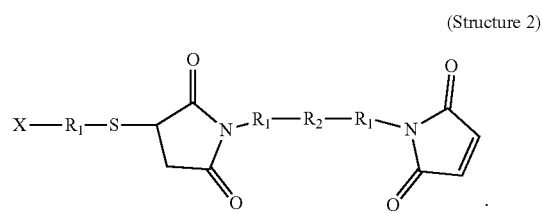

In various embodiments, the method for synthesizing the compound of Structure 1 or 2 is carried out under conditions that substantially favor the formation of Structure 1 or 2 and substantially prevent dimerization of X. The conditions can improve the yield of the reaction (e.g., improve the purity of the product).

In various embodiments, the method for synthesizing the compound of Structure 1 or 2, the step of reacting the functionalized nucleic acid X—R1-R2-A' and the covalent linker A"-R3-B is carried out at a X—R1-R2-A' concentration of below about 1 mM, 500 µM, 250 µM, 100 µM, or 50 µM. Alternatively, the X—R1-R2-A' concentration can be about 1 mM, 500 µM, 250 µM, 100 µM, or 50 µM.

In various embodiments, the method for synthesizing the compound of Structure 1 or 2, the step of reacting the functionalized nucleic acid X—R1-R2-A' and the covalent linker A"-R3-B is carried out with a molar excess of A"-R3-B of at least about 5, 10, 15, 20, 25, 30, 35, 40, 45, 50, or 100. Alternatively, the molar excess of A"-R3-B can be about 5, 10, 15, 20, 25, 30, 35, 40, 45, 50, or 100.

In various embodiments, the method for synthesizing the compound of Structure 1 or 2, the step of reacting the functionalized nucleic acid X—R1-R2-A' and the covalent linker A"-R3-B is carried out at a pH of below about 7, 6, 5, or 4. Alternatively, the pH can be about 7, 6, 5, or 4.

In various embodiments, the method for synthesizing the compound of Structure 1 or 2, the step of reacting the functionalized nucleic acid X—R1-R2-A' and the covalent linker A"-R3-B is carried out in a solution comprising water and a water miscible organic co-solvent. The water miscible organic co-solvent can comprise DMF, NMP, DMSO, or acetonitrile. The water miscible organic co-solvent can comprise about 10, 15, 20, 25, 30, 40, or 50% V (v/v) of the solution.

In various embodiments (e.g., for synthesizing Structure 17), the method further comprises the step of annealing a plurality of ══════ and/or ∿∿∿ , thereby forming a plurality of molecules comprising Structure 18:

(Structure 18)

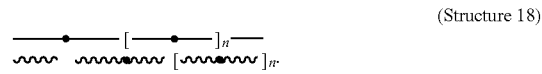

-continued

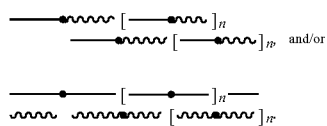

(Structure 19)

(Structure 20) and/or

In various embodiments (e.g., for synthesizing Structure 17), the method further comprises annealing ――― with the plurality of plurality of ―•― and ⌇⌇⌇.

In various embodiments (e.g., for synthesizing Structure 17), the molar ratio of ――― to ⌇⌇⌇ is about 5:100, 10:100, 20:100, 30:100, 40:100, or 50:100.

In various embodiments (e.g., for synthesizing Structure 17), the method further comprises annealing ⌒⌒⌒ with the plurality of plurality of ―•― and ⌇⌇⌇.

In various embodiments (e.g., for synthesizing Structure 17), the molar ratio of ⌒⌒⌒ to ―•― is about 5:100, 10:100, 20:100, 30:100, 40:100, or 50:100.

In various embodiments (e.g., for synthesizing Structure 17), the molar ratio of ―•― and ⌇⌇⌇ is about 1:1.

In various embodiments (e.g., for synthesizing Structure 17), the molar ratio of ―•― to ⌇⌇⌇ or the molar ratio of ⌇⌇⌇ to ―•― is about 100:90, 100:80, 100:75, 100:70, or 100:60.

In various embodiments (e.g., for synthesizing Structure 17), each ⚌ has a length of 15-30 base pairs.

In various embodiments (e.g., for synthesizing Structure 17), each ⚌ is an siRNA.

In various embodiments (e.g., for synthesizing Structure 17), each ⚌ comprises siRNA guide strand targeting Factor VII and a passenger strand hybridized to the guide strand.

In various embodiments (e.g., for synthesizing Structure 17), n is an integer from 1 to 100.

In various embodiments (e.g., for synthesizing Structure 17), • is a cleavable or non-cleavable linker.

In various embodiments, the method further comprises formulating any of the compounds or compositions in a nanoparticle.

In various embodiments, the oligonucleotide has a specific sequence, for example any one of the sequences disclosed herein. In one embodiment, the oligonucleotide is an siRNA having SEQ ID NO: 106. In one embodiment, the oligonucleotide is an siRNA having SEQ ID NO: 115.

In various embodiments, the subject is a cell, mammal, or human.

BRIEF DESCRIPTION OF THE DRAWINGS

FIGS. 10A and 10B and 10C present data showing FVII activity in mouse serum (knockdown by FVII homodimeric GalNAc conjugates normalized for GalNAc content), which is discussed in connection with Example 15.

FIG. 11 presents canonical GalNAc-siRNAs independently targeting FVII, ApoB and TTR, which are discussed in connection with Example 16.

FIG. 12 presents a GalNAC-heterotrimer conjugate (XD06726), which is discussed in connection with Example 17. Key: In this example, "GeneA" is siFVII; "GeneB" is siApoB; and "GeneC" is siTTR.

FIG. 37 presents a FVIIs-FVII as heterodimer (X12714), which is discussed in connection with Example 24.

FIG. 38 presents a gel analysis of heterodimer X12714 (Lane 12), which is discussed in connection with Example 24.

Figure 1:
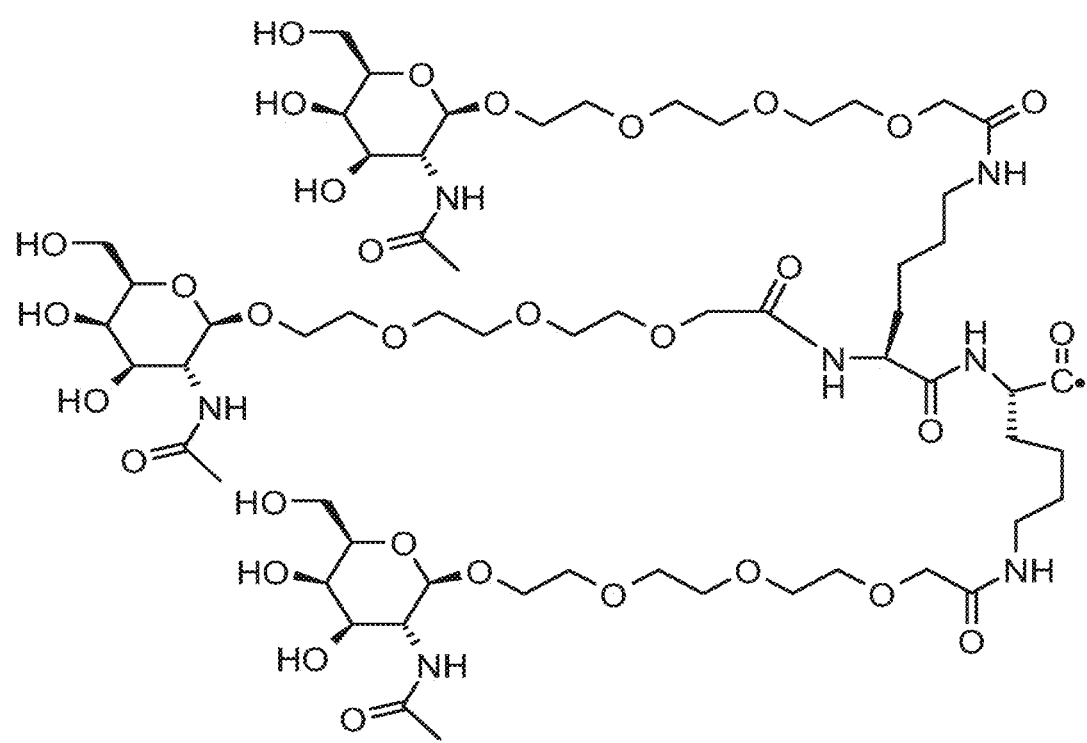
FIG. 1 presents the chemical structure of a tri-antennary N-actylgalactosamine ligand.

While the invention comprises embodiments in many different forms, there are shown in the drawings and will herein be described in detail several specific embodiments with the understanding that the present disclosure is to be considered as an exemplification of the principles of the technology and is not intended to limit the invention to the embodiments illustrated.

DETAILED DESCRIPTION OF THE PREFERRED EMBODIMENT

The various aspects of the invention have in common the manufacture and use of multi-conjugates containing oligonucleotides. The multi-conjugates may contain RNA and/or DNA. The RNA may be any form of bioactive RNA amenable to the multi-conjugation reactions conditions provided herein, such as siRNA, miRNA, and small activating RNA (saRNA).

The oligonucleotides used in the various aspects of the invention may be any that are of interest or used (A) in the medical arts, for example, to suppress or enhance expression of a target gene or protein in a subject, and in the treatment or prevention of any disease that would benefit from suppression or enhancement of the expression of a target gene or protein; (B) in performing biological research; and (C) to produce new or altered phenotypes in animals and plants. As a nonlimiting example, the oligonucleotides may be any RNA that is being used for RNA interference, RNA activation, or gene therapy, or is expected to be used in near future, such as RNA designed to be active in relation to c-myc, c-myb, c-fos, c-jun, bcl-2 or VEGF, VEGF-B, VEGF-C, VEGF-D, or PlGF.

The manufacturing methods described herein produce various multi-conjugates at higher levels of purity than have been previously described in the art. This feature of the invention is particularly advantageous for therapeutic applications of the multi-conjugates, and is likely to produce advantages for manufacture and use of the multi-conjugates in other applications such as research.

One aspect of the invention is oligonucleotide-containing multi-conjugates having a predetermined size and composition, and a method for making such multi-conjugates. The method produces multi-conjugates at higher levels of purity than have been previously described in the art.

Various features of the invention are discussed, in turn, below.

Nucleic Acids

In various embodiments, the nucleic acid or oligonucleotide is RNA, DNA, or comprises an artificial or non-natural nucleic acid analog. In various embodiments, the nucleic acid or oligonucleotide is single stranded. In various embodiments, the nucleic acid or oligonucleotide is double stranded (e.g., antiparallel double stranded).

In various embodiments, the nucleic acid or oligonucleotide is RNA, for example an antisense RNA (aRNA), CRISPR RNA (crRNA), long noncoding RNA (lncRNA), microRNA (miRNA), piwi-interacting RNA (piRNA), small interfering RNA (siRNA), messenger RNA (mRNA), short hairpin RNA (shRNA), small activating (saRNA), or ribozyme.

In one embodiment, the RNA is siRNA. For example, each double stranded oligonucleotide is an siRNA and/or has a length of 15-30 base pairs.

In various embodiments, the nucleic acid or oligonucleotide is an aptamer.

siRNA (small interfering RNA) is a short double-stranded RNA composed of 19-22 nucleic acids, which targets mRNA (messenger RNA) of a gene whose nucleotide sequence is identical with its sense strand in order to suppress expression of the gene by decomposing the target gene (Elbashir, S. M., Harborth, J., Lendeckel, W., Yalcin, A., Weber, K., and Tuschl, T. (2001) Duplexes of 21-nucleotide RNAs mediate RNA interference in cultured mammalian cells. Nature 411:494-8).

Another class of nucleic acid, useful in the methods of the invention, are miRNAs. MiRNAs are non-coding RNAs that play key roles in post-transcriptional gene regulation. miRNA can regulate the expression of 30% of all mammalian protein-encoding genes. Specific and potent gene silencing by double stranded RNA (RNAi) was discovered, plus additional small noncoding RNA (Canver, M. C. et al., Nature (2015)). Pre-miRNAs are short stem loops ~70 nucleotides in length with a 2-nucleotide 3'-overhang that are exported, into the mature 19-25 nucleotide duplexes. The miRNA strand with lower base pairing stability (the guide strand) can be loaded onto the RNA-induced silencing complex (RISC). The passenger guide strand can be functional but is usually degraded. The mature miRNA tethers RISC to partly complementary sequence motifs in target mRNAs predominantly found within the 3' untranslated regions (UTRs) and induces posttranscriptional gene silencing (Bartel, D. P. Cell, 136:215-233 (2009); Saj, A. & Lai, E. C. Curr Opin Genet Dev, 21:504-510 (2011)). MiRNAs mimics are described for example, in U.S. Pat. No. 8,765,709.

In some embodiments, the RNA can be short hairpin RNA (shRNA), for example, as described in U.S. Pat. Nos. 8,202,846 and 8,383,599.

In some embodiments, the RNA can CRISPR RNA (crRNA), for example, CRISPR array of Type V can be processed into short mature crRNAs of 42-44 nucleotides in length, with each mature crRNA beginning with 19 nucleotides of direct repeat followed by 23-25 nucleotides of spacer sequence. Alternatively, mature crRNAs in Type II systems can start with 20-24 nucleotides of spacer sequence followed by about 22 nucleotides of direct repeat. CRISPR systems are described for example, in U.S. Pat. No. 8,771,945, Jinek et al., Science, 337(6096):816-821 (2012), and International Patent Application Publication No. WO 2013/176772.

In various embodiments, the nucleic acid or oligonucleotide is 15-30, 17-27, 19-26, 20-25, 40-50, 40-150, 100-300, 1000-2000, or up to 10000 nucleotides in length.

In various embodiments, the oligonucleotide is double stranded and complementary. Complementary can be 100% complementary, or less than 100% complementary where the oligonucleotide nevertheless hybridizes and remains double stranded under relevant conditions (e.g., physiologically relevant conditions). For example, a double stranded oligonucleotide can be at least about 80, 85, 90, or 95% complementary.

In some embodiments, RNA is long noncoding RNA (lncRNA), LncRNAs are a large and diverse class of transcribed RNA molecules with a length of more than 200 nucleotides that do not encode proteins (or lack >100 amino acid open reading frame). LncRNAs are thought to encompass nearly 30,000 different transcripts in humans, hence lncRNA transcripts account for the major part of the non-coding transcriptome (see, e.g., Derrien et al., The GENCODE v7 catalog of human long noncoding RNAs: analysis of their gene structure, evolution, and expression. Genome Res, 22(9):1775-89 (2012)).

In yet other embodiments, RNA is messenger RNA (mRNA). mRNA and its application as a delivery method for in-vivo production of proteins, is described, for example, in International Patent Application Publication No. WO 2013/151736.

In other embodiments, RNA can be small activating (saRNA) (e.g., as described in Chappell et al., Nature Chemical Biology, 11:214-220 (2015)), or ribozyme (Doherty et al., Ann Rev Biophys Biomo Struct, 30:457-475 (2001)).

In some embodiments, the nucleic acid or oligonucleotide is DNA, for example an antisense DNA (aDNA) (e.g., antagomir) or antisense gapmer. Examples of aDNA, including gapmers and multimers, are described for example in Subramanian et al., Nucleic Acids Res, 43(19):9123-9132 (2015) and International Patent Application Publication No. WO 2013/040429. Examples of antagamirs are described for example, in U.S. Pat. No. 7,232,806.

In various embodiments, the oligonucleotide has a specific sequence, for example any one of the sequences disclosed herein. In one embodiment, the oligonucleotide is an siRNA having SEQ ID NO: 106. In one embodiment, the oligonucleotide is an siRNA having SEQ ID NO: 115.

A general procedure for oligonucleotide synthesis is provided in the Examples below. Other methods that can be adapted for use with the invention are known in the art.

Modifications to Nucleic Acids

In various embodiments, the nucleic acid or oligonucleotide further comprises a chemical modification. The chemical modification can comprise a modified nucleoside, modified backbone, modified sugar, or modified terminus.

Phosphorus-containing linkages include, but are not limited to, phosphorothioates, chiral phosphorothioates, phosphorodithioates, phosphotriesters, aminoalkylphosphotriesters, methyl and other alkyl phosphonates comprising 3'-alkylene phosphonates and chiral phosphonates, phosphinates, phosphoramidates comprising 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'.

The oligonucleotides contained in the multi-conjugates of this invention may be modified using various strategies known in the art to produce a variety of effects, including, e.g., improved potency and stability in vitro and in vivo. Among these strategies are: artificial nucleic acids, e.g., 2'-O-methyl-substituted RNA; 2'-fluro-2'-deoxy RNA, peptide nucleic acid (PNA); morpholinos; locked nucleic acid (LNA); Unlocked nucleic acids (UNA); bridged nucleic acid (BNA); glycol nucleic acid (GNA); and threose nucleic acid (TNA); or more generally, nucleic acid analogs, e.g., bicyclic and tricyclic nucleoside analogs, which are structurally similar to naturally occurring RNA and DNA but have alterations in one or more of the phosphate backbone, sugar, or nucleobase portions of the naturally-occurring molecule. Typically, analogue nucleobases confer, among other things, different base pairing and base stacking properties. Examples include universal bases, which can pair with all four canon bases. Examples of phosphate-sugar backbone analogues include PNA. Morpholino-based oligomeric compounds are described in Braasch et al., Biochemistry, 41(14):4503-4510 (2002) and U.S. Pat. Nos. 5,539,082; 5,714,331; 5,719,262; and 5,034,506.

In the manufacturing methods described herein, some of the oligonucleotides are modified at a terminal end by substitution with a chemical functional group. The substitution can be performed at the 3' or 5' end of the oligonucleotide, and is preferably performed at the 3' ends of both the sense and antisense strands of the monomer, but is not always limited thereto. The chemical functional groups may include, e.g., a sulfhydryl group (SH), a carboxyl group (—COOH), an amine group (—NH2), a hydroxy group (—OH), a formyl group (—CHO), a carbonyl group (—CO—), an ether group (—O—), an ester group (—COO—), a nitro group (—NO$_2$), an azide group (—N$_3$), or a sulfonic acid group (—SO$_3$H).

The oligonucleotides contained in the multi-conjugates of this invention may be modified can also include, additionally or alternatively, nucleobase (often referred to in the art simply as "base") modifications or substitutions. Modified nucleobases include nucleobases found only infrequently or transiently in natural nucleic acids, e.g., hypoxanthine, 6-methyladenine, 5-Me pyrimidines, particularly 5-methylcytosine (also referred to as 5-methyl-2' deoxycytosine and often referred to in the art as 5-Me-C), 5-hydroxymethylcytosine (HMC), glycosyl HMC and gentobiosyl HMC, as well as synthetic nucleobases, e.g., 2-aminoadenine, 2-(methylamino)adenine, 2-(imidazolylalkyl)adenine, 2-(aminoalklyamino)adenine or other heterosubstituted alkyladenines, 2-thiouracil, 2-thiothymine, 5-bromouracil, 5-hydroxymethyluracil, 8-azaguanine, 7-deazaguanine, N6

(6-aminohexyl)adenine, and 2,6-diaminopurine. Kornberg, A., DNA Replication, W. H. Freeman & Co., San Francisco, pp 75-77 (1980); Gebeyehu et al., Nucl. Acids Res, 15:4513 (1997). A "universal" base known in the art, e.g., inosine, can also be included. 5-Me-C substitutions have been shown to increase nucleic acid duplex stability by 0.6-1.2° C. (Sanghvi, Y. S., in Crooke, S. T. and Lebleu, B., eds., Antisense Research and Applications, CRC Press, Boca Raton, pp 276-278 (1993) and are aspects of base substitutions. Modified nucleobases can include other synthetic and natural nucleobases, such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudo-uracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylquanine and 7-methyladenine, 8-azaguanine and 8-azaadenine, 7-deazaguanine and 7-deazaadenine, and 3-deazaguanine and 3-deazaadenine. Hydroxy group (—OH) at a terminus of the nucleic acid can be substituted with a functional group such as sulfhydryl group (—SH), carboxyl group (COOH) or amine group (—NH$_2$). The substitution can be performed at 3' end or 5' end, and is preferably occurred at 3' ends of both sense and antisense are substituted with such functional group, but not always limited thereto.

Linkers

In various aspects and embodiments of the invention, oligonucleotides are linked covalently. Linkers may be cleavable (e.g., under intracellular conditions, to facilitate oligonucleotide delivery and/or action) or non-cleavable. Although generally described below and in the Examples in context of linkers using nucleophile-electrophile chemistry, other chemistries and configurations are possible. And, as will be understood by those having ordinary skill, various linkers, including their composition, synthesis, and use are known in the art and may be adapted for use with the invention.

In various embodiments, a covalent linker can comprise the reaction product of nucleophilic and electrophilic group. For example, a covalent linker can comprise the reaction product of a thiol and maleimide, a thiol and vinylsulfone, a thiol and pyridyldisulfide, a thiol and iodoacetamide, a thiol and acrylate, an azide and alkyne, or an amine and carboxyl group. As described herein, one of these groups is connected to an oligonucleotide (e.g., thiol (—SH) functionalization at the 3' or 5' end) and the other groups is encompassed by a second molecule (e.g., linking agent) that ultimately links two oligonucleotides (e.g., maleimide in DTME).

In various embodiments, the nucleic acid or oligonucleotide is connected to the linker via a phosphodiester or thiophosphodiester (e.g., R1 in Structure 1 is a phosphodiester or thiophosphodiester). In various embodiments, the nucleic acid or oligonucleotide is connected to the linker via a C2-C10, C3-C6, or C6 alkyl (e.g., R2 in Structure 1 is a C2-C10, C3-C6, or C6 alkyl). Alternatively, these moieties (e.g., R1 and/or R2 in Structure 1) are optional and a direct linkage is possible.

In various embodiments, the nucleic acid or oligonucleotide is connected to the linker via the reaction product of a thiol and maleimide group. (e.g., A in Structure 1 is the reaction product of a thiol and maleimide group). Preferred linking agents utilizing such chemistry include DTME (dithiobismaleimidoethane), BM(PEG)2 (1,8-bis(maleimido)diethylene glycol), BM(PEG)3 (1,11-bismaleimido-triethyleneglycol), BMOE (bismaleimidoethane), BMH (bismaleimidohexane), or BMB (1,4-bismaleimidobutane).

Again, the examples are illustrative and not limiting. In various embodiments, oligonucleotides can be linked together directly, via functional end-substitutions, or indirectly by way of a linking agent. In various embodiments, the oligonucleotide can be bound directly to a linker (e.g., R1 and R2 of Structure 1 are absent). Such bonding can be achieved, for example, through use of 3'-thionucleosides, which can be prepared according to the ordinary skill in the art. See, e.g., Sun et al. "Synthesis of 3'-thioribonucleosides and their incorporation into oligoribonucleotides via phosphoramidite chemistry" RNA. 1997 November; 3(11):1352-63. In various embodiments, the linking agent may be a non-ionic hydrophilic polymer such as polyethyleneglycol (PEG), polyvinylpyrolidone and polyoxazoline, or a hydrophobic polymer such as PLGA and PLA.

A polymer linking agent used as a mediator for a covalent bond may be nonionic hydrophilic polymers including PEG, Pluronic, polyvinylpyrolidone, polyoxazoline, or copolymers thereof; or one or more biocleavable polyester polymers including poly-L-lactic acid, poly-D-lactic acid, poly-D,L-lactic acid, poly-glycolic acid, poly-D-lactic-co-glycolic acid, poly-L-lactic-co-glycolic acid, poly-D,L-lactic-co-glycolic acid, polycaprolactone, polyvalerolactone, polyhydroxybutyrate, polyhydroxyvalerate, or copolymers thereof, but is not always limited thereto.

The linking agent may have a molecular weight of 100-10,000 Daltons. Examples of such linking agent include dithio-bis-maleimidoethane (DIME), 1,8-bismaleimidodiethyleneglycol (BM(PEG)2), tris-(2-maleimidoethyl)-amine (TMEA), tri-succinimidyl aminotriacetate (TSAT), 3-arm-poly(ethylene glycol) (3-arm PEG), maleimide, N-hydroxysuccinimide (NHS), vinylsulfone, iodoacetyl, nitrophenyl azide, isocyanate, pyridyldisulfide, hydrazide, and hydroxyphenyl azide.

A linking agent having cleavable bonds (such as a reductant bond that is cleaved by the chemical environment of the cytosol) or a linking agent having non-cleavable bonds can be used herein. For example, the linking agent of the foregoing aspects of present invention can have non-cleavable bonds such as an amide bond or a urethane bond. Alternatively, the linking agent of the foregoing aspects of the present invention can have cleavable bonds such as an acid cleavable bond (e.g., a covalent bond of ester, hydrazone, or acetal), a reductant cleavable bond (e.g., a disulfide bond), a bio-cleavable bond, or an enzyme cleavable bond. In one embodiment, the cleavable covalent linker is cleavable under intracellular conditions. Additionally, any linking agent available for drug modification can be used in the foregoing aspects of the invention without limitation.

Further, combinations of functional groups and linking agents may include: (a) where the functional groups are amino and thiol, the linking agent may be Succinimidyl 3-(2-pyridyldithio)propionate, or Succinimydyl 6-([3(2-pyridyldithio)propioamido]hexanoate; (b) where the functional group is amino, the linking agent may be 3,3'-dithiodipropionic acid di-(N-succinimidyl ester), Dithio-bis (ethyl 1H-imidazole-1-carboxylate), or Dithio-bis(ethyl 1Himidazole-1-carboxylate); (c) where the functional groups are amino and alkyne, the linking agent may be Sulfo-N-succinimidyl3-[[2-(p-azidosalicylamido)ethyl]-1, 3'-dithio]propionate; and (d) where the functional group y is thiol, the linking agent is dithio-bis-maleimidoethan (DTME); 1,8-Bis-maleimidodiethyleneglycol (BM(PEG)2); or dithiobis(sulfosuccinimidyl propionate) (DTSSP).

In the foregoing methods of preparing compounds, an additional step of activating the functional groups can be included. Compounds that can be used in the activation of the functional groups include but are not limited to 1-ethyl-3,3-dimethylaminopropyl carbodiimide, imidazole, N-hydroxysuccinimide, dichlorohexylcarbodiimide, N-betaMaleimidopropionic acid, N-beta-maleimidopropyl succinimide ester or N-Succinimidyl 3-(2-pyrid yldithio)propionate.

Monomeric Intermediate Compounds

In various aspects, the invention provides an oligonucleotide coupled to a covalent linker, which can be used, for example, in the synthesis of defined multi-conjugate oligonucleotides having predetermined sizes and compositions.

In one aspect, the invention provides a compound according to Structure 1:

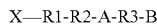
X—R1-R2-A-R3-B (Structure 1)

wherein:
X is a nucleic acid bonded to R1 through its 3' or 5' terminus;
R1 a phosphodiester, thiophosphodiester, sulfate, amide, glycol, or is absent;
R2 is a C2-C10 alkyl, alkoxy, or aryl group, or is absent;
A is the reaction product of a nucleophile and an electrophile;
R3 is a C2-C10 alkyl, alkoxy, aryl, alkyldithio group, ether, thioether, thiopropionate, or disulfide; and
B is a nucleophile or electrophile (e.g., a thiol, maleimide, vinylsulfone, pyridyldisulfide, iodoacetamide, acrylate, azide, alkyne, amine, or carboxyl group).

In one aspect, the invention provides a compound according to Structure 2:

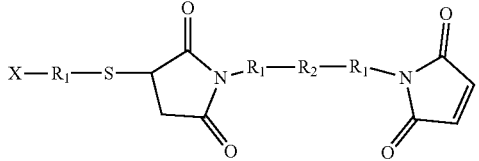
(Sturcture 2)

wherein:
X is a nucleic acid bonded to RI1 via a phosphate or thiophosphate at its 3' or 5' terminus;
each R1 is independently a C2-C10 alkyl, alkoxy, or aryl group; and R2 is a thiopropionate or disulfide group.

In one aspect, the invention provides a compound according to Structure 3:

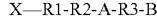
X—R1-R2-A-R3-B (Structure 3)

wherein:
X is a nucleic acid bonded to R2 through its 3' or 5' terminus;
R1 a phosphate, thiophosphate, sulfate, amide, glycol, or is absent;
R2 is a C2-C10 alkyl, alkoxy, or aryl group, or is absent;
A is the reaction product of a first and a second reactive moiety;
R3 is an C2-C10 alkyl, alkoxy, aryl, alkoxy, alkyldithio group, ether, thioether, thiopropionate, or disulfide; and
B is a third reactive moiety.

In various aspects, the invention also provides methods for synthesizing an oligonucleotide coupled to a covalent linker.

In one aspect, the invention provides a method for synthesizing a compound according to Structure 1 (or adapted for synthesizing a compounds according to Structure 2 or 3), the method comprising:
reacting a functionalized nucleic acid X—R1-R2-A' and a covalent linker A"-R3-B, wherein A' and A" comprise a nucleophile and an electrophile, in a dilute solution of X—R2-R2-A' and with a stoichiometric excess of A"-R3-B, thereby forming the compound X—R1-R2-A-R3-B (Structure 1), wherein:
X is a nucleic acid bonded to R2 through its 3' or 5' terminus;
R2 a phosphodiester, thiophosphodiester, sulfate, amide, glycol, or is absent;
R2 is a C2-C10 alkyl, alkoxy, or aryl group, or is absent;
A is the reaction product of a nucleophile and an electrophile;
R3 is a C2-C10 alkyl, alkoxy, aryl, alkyldithio group, ether, thioether, thiopropionate, or disulfide; and
B is a nucleophile or electrophile (e.g., a thiol, maleimide, vinylsulfone, pyridyldisulfide, iodoacetamide, acrylate, azide, alkyne, amine, or carboxyl group).

The method can further comprise the step of synthesizing the functionalized nucleic acid X—R2-R2-A', wherein A' comprises a thiol (—SH) by (i) introducing a the thiol during solid phase synthesis of the nucleic acid using phosphoramidite oligomerization chemistry or (ii) reduction of a disulfide introduced during the solid phase synthesis.

In various embodiments, the method for synthesizing the compound of Structure 1 further comprises synthesizing the compound of Structure 2.

The oligonucleotide coupled to a covalent linker can include any one or more of the features described herein, including in the Examples. For example, the compounds can include any one or more of the nucleic acids (with or without modifications), targeting ligands, and/or linkers described above, or any of the specific structures or chemistries shown in the summary or Examples. Example 1 provides an example methodology for generating thiol terminated oligonucleotides. Example 2 provides an example methodology for preparing an oligonucleotide coupled to a linker.

In various embodiments, the method for synthesizing the compound of Structure 1 or 2 is carried out under conditions that substantially favor the formation of Structure 1 or 2 and substantially prevent dimerization of X. The conditions can improve the yield of the reaction (e.g., improve the purity of the product).

In various embodiments, the method for synthesizing the compound of Structure 1 or 2, the step of reacting the functionalized nucleic acid X—R2-R2-A' and the covalent linker A"-R3-B is carried out at a X—R2-R2-A' concentration of below about 1 mM, 500 µM, 250 µM, 100 µM, or 50 µM. Alternatively, the X—R2-R2-A' concentration can be about 1 mM, 500 µM, 250 µM, 100 µM, or 50 µM.

In various embodiments, the method for synthesizing the compound of Structure 1 or 2, the step of reacting the functionalized nucleic acid X—R1-R2-A' and the covalent linker A"-R3-Bis carried out with a molar excess of A"-R3-B of at least about 5, 10, 15, 20, 25, 30, 35, 40, 45, 50, or 100. Alternatively, the molar excess of A"-R3-B can be about 5, 10, 15, 20, 25, 30, 35, 40, 45, 50, or 100.

In various embodiments, the method for synthesizing the compound of Structure 1 or 2, the step of reacting the functionalized nucleic acid X—R1-R2-A' and the covalent linker A"-R3-Bis carried out at a pH of below about 7, 6, 5, or 4. Alternatively, the pH can be about 7, 6, 5, or 4.

In various embodiments, the method for synthesizing the compound of Structure 1 or 2, the step of reacting the functionalized nucleic acid X—R1-R2-A' and the covalent linker A"-R3-B is carried out in a solution comprising water and a water miscible organic co-solvent. The water miscible organic co-solvent can comprise DMF (dimethylformamide), NMP (N-methyl-2-pyrrolidone), DMSO (dimethyl sulfoxide), or acetonitrile. The water miscible organic co-solvent can comprise about 10, 15, 20, 25, 30, 40, or 50% V (v/v) of the solution.

In various embodiments, the compound is isolated or substantially pure. For example, the compound can be at least 75, 80, 85, 90, 95, 96, 97, 98, 99, or 100% pure. In one embodiment, the compound is about 85-95% pure. Likewise, the methods for synthesizing the compounds and compositions according to the invention can result in a product that is at least 75, 80, 85, 90, 95, 96, 97, 98, 99, or 100% pure. In one embodiment, the product is about 85-95% pure. Preparations can be greater than or equal to 50% pure; preferably greater than or equal to 75% pure; more preferably greater than or equal to 85% pure; and still more preferably, greater than or equal to 95% pure.

As used herein, the term about is used in accordance with its plain and ordinary meaning of approximately. For example, "about X" encompasses approximately the value X as stated, including similar amount that are within the measurement error for the value of X or amounts that are approximately the same as X and have essentially the same properties as X.

As used herein, isolated include compounds that are separated from other, unwanted substances. The isolated compound can be synthesized in a substantially pure state or separated from the other components of a crude reaction mixture, except that some amount of impurities, including residual amounts of other components of the crude reaction mixture, may remain. Similarly, pure or substantially pure means sufficiently free from impurities to permit its intended use (e.g., in a pharmaceutical formulation or as a material for a subsequent chemical reaction). X % pure means that the compound is X % of the overall composition by relevant measure, which can be for example by analytical methods such as HPLC.

Dimeric Compounds and Intermediates

In various aspects, the invention provides dimeric defined multi-conjugate oligonucleotides. These compounds include homodimers (e.g., two oligonucleotides that are substantially the same, for example targeting the same gene in vivo) and heterodimers (e.g., two oligonucleotides that are substantially different, for example different sequences or targeting different genes in vivo)

In one aspect, the invention provides an isolated compound according to Structure 4:

═══•═══ (Structure 4)

wherein:
each ═══ is a double stranded oligonucleotide designed to react with the same molecular target in vivo, and
• is a covalent linker joining single strands of adjacent single stranded oligonucleotides at their 3' or 5' termini, and having the structure —R1-R2-A-R3-A-R2-R1- wherein:
each R1 is independently a phosphodiester, thiophosphodiester, sulfate, amide, glycol, or is absent;
each R2 is independently a C2-C10 alkyl, alkoxy, or aryl group, or is absent;
each A is independently the reaction product of a nucleophile and an electrophile, and R3 is a C2-C10 alkyl, alkoxy, aryl, alkoxy, alkyldithio group, ether, thioether, thiopropionate, or disulfide.

In one aspect, the invention provides an isolated compound according to Structure 5: ─────•ᴧᴧᴧᴧ

─────•ᴧᴧᴧᴧ (Structure 5)

wherein:
───── is a first single stranded oligonucleotide
ᴧᴧᴧᴧ is a second single stranded oligonucleotide having a different sequence from the first, and
• is a covalent linker joining single strands of adjacent single stranded oligonucleotides at their 3' or 5' termini, and having the structure —R1-R2-A-R3-A-R2-R1- wherein:
each R1 is independently a phosphate, sulfate, amide, glycol, or is absent;
each R2 is independently a C2-C10 alkyl, alkoxy, or aryl group, or is absent;
each A is independently the reaction product of a thiol and maleimide, a thiol and vinylsulfone, a thiol and pyridyldisulfide, a thiol and iodoacetamide, a thiol and acrylate, an azide and alkyne, or an amine and carboxyl group, and
R3 is an C2-C10 alkyl, alkoxy, aryl, alkoxy, alkyldithio group, ether, thioether, thiopropionate, or disulfide.

In one aspect, the invention provides an isolated compound according to Structure 6:

═══•ᴧᴧᴧ (Structure 6)

wherein:
═══ is a first double stranded oligonucleotide
ᴧᴧᴧ is a second double stranded oligonucleotide having a different sequence from the first, and
• is a covalent linker joining single strands of adjacent single stranded oligonucleotides at their 3' or 5' termini, and having the structure —R1-R2-A-R3-A-R2-R1- wherein:
each R1 is independently a phosphate, sulfate, amide, glycol, or is absent;
each R2 is independently a C2-C10 alkyl, alkoxy, or aryl group, or is absent;
each A is independently the reaction product of a thiol and maleimide, a thiol and vinylsulfone, a thiol and pyridyldisulfide, a thiol and iodoacetamide, a thiol and acrylate, an azide and alkyne, or an amine and carboxyl group, and
R3 is an C2-C10 alkyl, alkoxy, aryl, alkoxy, alkyldithio group, ether, thioether, thiopropionate, or disulfide.

In one aspect, the invention provides an isolated compound according to Structure 11:

═══•─── (Structure 11)

wherein:
═══ is a double stranded oligonucleotide,
─── is a single stranded oligonucleotide, and
• is a covalent linker joining single strands of adjacent single stranded oligonucleotides.

In various aspects, the invention provides methods for synthesizing dimeric defined multi-conjugate oligonucleotides.

In one aspect, the invention provides a method for synthesizing a compound of Structure 5:

─────•ᴧᴧᴧᴧ (Structure 5)

wherein ———— is a first single stranded oligonucleotide, ∿∿∿ is a second single stranded oligonucleotide having a different sequence from the first, and • is a covalent linker joining single strands of adjacent single stranded oligonucleotides at their 3' or 5' termini, the method comprising the steps of:
(i) reacting a first single stranded oligonucleotide R1 with a bifunctional linking moiety ○, wherein R1 is a chemical group capable of reacting with ○ under conditions that produce the mono-substituted product ————○; ;
(ii) reacting ————○; with a second single stranded oligonucleotide ∿∿∿R₂, wherein R2 is a chemical group capable of reacting with ○, thereby forming ————●∿∿∿ .

The method can further comprise the step of annealing complementary ———— and ∿∿∿ to yield Structure 6:
══•══ (Structure 6).

In one aspect, the invention provides a method for synthesizing an isolated compound of Structure 4:
══•══ (Structure 4)
wherein each ══ is a double stranded oligonucleotide and • is a covalent linker joining single strands of adjacent single stranded oligonucleotides at their 3' or 5' termini, the method comprising the steps of: ————
(i) reacting a first single stranded oligonucleotide ———— R1 with a bifunctional linking moiety ○, wherein R1 is a chemical group capable of reacting with ○, thereby forming a monosubstituted product ————○; ;
(ii) reacting ————○; with a second single stranded oligonucleotide ———— R₂, wherein R2 is a chemical group capable of reacting with ○, thereby forming a single stranded dimer ————•————
(iii) annealing single stranded oligonucleotides, at the same time or sequentially, thereby forming ══•══

In one aspect, the invention provides a method for synthesizing an isolated compound of Structure 4:
══•══ (Structure 4) wherein each ══ is a double stranded oligonucleotide and • is a covalent linker joining single strands of adjacent single stranded oligonucleotides at their 3' or 5' termini, the method comprising the steps of:
(i) forming ══•—— by:
(a) annealing a first single stranded oligonucleotide ———— and a second single stranded oligonucleotide ———— R₁, thereby forming ══ R₁, and reacting ══ R₁ with a third single stranded oligonucleotide ———— R₂, wherein R1 and R2 are chemical moieties capable of reacting directly or indirectly to form a covalent linker •, thereby forming ══•—— ; or
(b) reacting the second single stranded oligonucleotide ———— R₁ and the third single stranded oligonucleotide ———— R₂, thereby forming ——•—— , and annealing the first single stranded oligonucleotide and ——•—— , thereby forming ══•——
(ii) annealing ══•—— and a fourth single stranded oligonucleotide ———— , thereby forming ══•══ .

This methodology can be adapted for synthesizing an isolated compound according to ══•══ (Structure 11), for example by omitting step (ii).

In one aspect, the invention provides a method for synthesizing an isolated compound of Structure 4 ══•══ (Structure 4) wherein each ══ is a double stranded oligonucleotide and • is a covalent linker joining single strands of adjacent single stranded oligonucleotides at their 3' or 5' termini, the method comprising the steps of:
(a) annealing a first single stranded oligonucleotide ———— and a second single stranded oligonucleotide ———— R₁, thereby forming ══ R₁;
(b) annealing a third single stranded oligonucleotide ———— R₂ and a fourth single stranded oligonucleotide ———— , thereby forming ══ R₂;
(c) reacting ══ R₁ and ══ R₂, wherein R1 and R2 are chemical moieties capable of reacting directly or indirectly to form a covalent linker •, thereby forming ══•══ .

As with the other compounds and compositions according to the invention, dimeric compounds and intermediates can include any one or more of the features described herein, including in the Examples. For example, the compounds can include any one or more of the nucleic acids (with or without modifications), targeting ligands, and/or linkers described above, or any of the specific structures or chemistries shown in the summary or Examples.

Example 4 provides an example methodology for preparing dimerized oligonucleotides and Example 5 provides an example methodology for annealing single stranded oligonucleotides to form double stranded oligonucleotides. Example 7 provides an example methodology for preparing various oligonucleotide precursors useful in the syntheses above. Example 8 provides an example methodology for preparing various oligonucleotide multimers, which are also useful in the syntheses above.

Examples of heterodimers are provided in Examples 9 and 10.

Examples of homodimers are provided in Examples 12-15.

In various embodiments, R1, R2, and the bifunctional linking moiety ○ can form a covalent linker • as described and shown herein. For example, in various embodiments, R1 and R2 can each independently comprise a reactive moiety, for example an electrophile or nucleophile. In one embodiment, R1 and R2 can each independently be selected from the group consisting of a thiol, maleimide, vinylsulfone, pyridyldisulfide, iodoacetamide, acrylate, azide, alkyne, amine, and carboxyl group. In various embodiments, the bifunctional linking moiety comprises two reactive moieties that can be sequentially reacted according to steps (i) and (ii) above, for example a second electrophile/nucleophile that can be reacted with an electrophile/nucleophile in R1 and R2. Examples of bifunctional linking moieties, include, but are not limited to, DTME, BM(PEG)2, BM(PEG)3, BMOE, BMH, or BMB.

These, as well as all other synthetic methods of the invention, can further comprise the step of adding a targeting ligand to the molecule. Example 6 provides an example methodology for adding a targeting ligand (e.g., GalNAc). Addition methods for adding targeting ligands are known in the art and can be adapted for the present invention by those skilled in the art.

Multimeric (n>2) Compounds and Intermediates

In various aspects, the invention provides multimeric (n>2) defined multi-conjugate oligonucleotides, including defined tri-conjugates and defined tetraconjugates.

In one aspect, the invention provides a compound according to Structure 7 or 8:

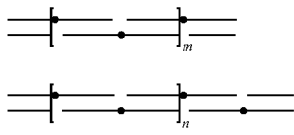

(Structure 7)

(Structure 8)

wherein:
each ════ is a double stranded oligonucleotide,
each • is a covalent linker joining single strands of adjacent single stranded oligonucleotides, and
m is an integer ≥1 and n is an integer ≥0.

In one aspect, the invention provides a compound according to Structure 9 and wherein n=0: ══•══ (Structure 9). In one aspect, the invention provides a compound according to Structure 10 and wherein m=1: ══•══ (Structure 10).

In one aspect, the invention provides a compound according to Structure 12, 13, 14, or 15:

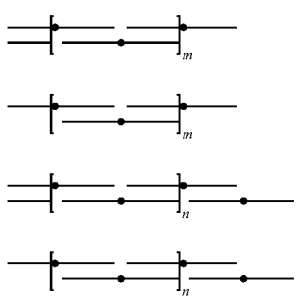

(Structure 12)

(Structure 13)

(Structure 14)

(Structure 15)

wherein:
each ════ is a double stranded oligonucleotide,
each is a single stranded oligonucleotide,
each • is a covalent linker joining single strands of adjacent single stranded oligonucleotides, and
m is an integer ≥1 and n is an integer ≥0.

In various aspects, the invention provides methods for synthesizing multimeric (n>2) defined multi-conjugate oligonucleotides, including defined tri-conjugates and defined tetraconjugates.

In one aspect, the invention provides a method for synthesizing a compound according to Structure 7 or 8:

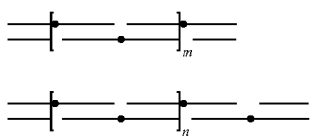

(Structure 7)

(Structure 8)

wherein: each ════ is a double stranded oligonucleotide, each • is a covalent linker joining single strands of adjacent single stranded oligonucleotides, and m is an integer ≥1 and n is an integer ≥0, the method comprising the steps of:

(i) forming ══•── by:
(a) annealing a first single stranded oligonucleotide ──── and a second single stranded oligonucleotide ────$R_1$, thereby forming ════$R_1$, and reacting ════$R_1$, with a third single stranded oligonucleotide ────$R_2$, wherein R1 and R2 are chemical moieties capable of reacting directly or indirectly to form a covalent linker •, thereby forming; ══•── or
(b) reacting the second single stranded oligonucleotide ────$R_1$ and the third single stranded oligonucleotide ────$R_2$, thereby forming ──•── and annealing the first single stranded oligonucleotide ──── and ──•──, thereby forming ══•── ;
(ii) annealing ══•── and a second single stranded dimer ──•── thereby forming ══•══•── and, optionally, annealing one or more additional single stranded dimers ──•── to ══•══•── thereby forming,

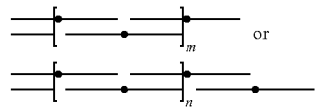

or wherein m is an integer ≥1 and n is an integer ≥0; and
(iii) annealing a fourth single stranded oligonucleotide ──── to the product of step (ii), thereby forming structure 7 or 8.

In one aspect, the invention provides a method for synthesizing a compound according to Structure 7 or 8:

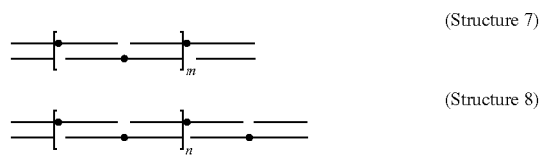

(Structure 7)

(Structure 8)

wherein: ════ each is a double stranded oligonucleotide, each • is a covalent linker joining single strands of adjacent single stranded oligonucleotides, and m is an integer ≥1 and n is an integer ≥0, the method comprising the steps of:
(i) annealing a first single stranded oligonucleotide ──── and a first single stranded dimer ──•── , thereby forming ══•── ;
(ii) annealing ══•── and a second single stranded dimer ──•── , thereby forming ══•══•── and, optionally, annealing one or more additional single stranded dimers ──•── to ══•══•── thereby forming,

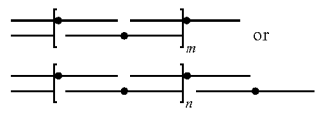

or wherein m is an integer ≥1 and n is an integer ≥0; and
(iii) annealing a second single stranded oligonucleotide ──── to the product of step (ii), thereby forming structure 7 or 8.

In one aspect, the invention provides a method for synthesizing a compound of Structure 9: ═•═•═ (Structure 9), wherein each ═══ is a double stranded oligonucleotide, each • is a covalent linker joining single strands of adjacent single stranded oligonucleotides, the method comprising the steps of:
(i) forming ═•── by:
(a) annealing a first single stranded oligonucleotide ──── and a second single stranded oligonucleotide ──── R₁, thereby forming ═══ R₁, and reacting ═══ R₁ with a third single stranded oligonucleotide ──── R₂, wherein R1 and R2 are chemical moieties capable of reacting directly or indirectly to form a covalent linker •, thereby forming ═•── ; or
(b) reacting the second single stranded oligonucleotide ──── R₁, and the third single stranded oligonucleotide ──── R₂, thereby forming ──•──, and annealing the first single stranded oligonucleotide ──── and ──•──, thereby forming ═•── ;
(ii) annealing ═•── and a single stranded dimer ──•──, thereby forming ═•═•── ; and
(iii) annealing ═•═•── and a fourth single stranded oligonucleotide ──── thereby forming ═•═•═ .

In one aspect, the invention provides a method for synthesizing a compound of Structure 10: ═•═•═•═ (Structure 10), wherein each ═══ is a double stranded oligonucleotide, each • is a covalent linker joining single strands of adjacent single stranded oligonucleotides, the method comprising the steps of:
(i) forming ═•── by:
(a) annealing a first single stranded oligonucleotide ──── and a second single stranded oligonucleotide ──── R₁, thereby forming ═══ R₁, and reacting ═══ R₁ with a third single stranded oligonucleotide ──── R₂, wherein R1 and R2 are chemical moieties capable of reacting directly or indirectly to form a covalent linker •, thereby forming ═•── ; or
(b) reacting the second single stranded oligonucleotide ──── R₁ and the third single stranded oligonucleotide ──── R₂, thereby forming ──•──, and annealing the first single stranded oligonucleotide ──── and ──•──, thereby forming ═•── ;
(ii) annealing ═•── and a single stranded dimer ──•──, thereby forming ═•═•── ;
(iii) annealing ═•═•── and a second single stranded dimer ──•──, thereby forming ═•═•═•── ; and
(iv) annealing ═•═•═•── and a fourth single stranded oligonucleotide ────, thereby forming ═•═•═•═ .

As with the other compounds and compositions according to the invention, dimeric compounds and intermediates can include any one or more of the features described herein, including in the Examples. For example, the compounds can include any one or more of the nucleic acids (with or without modifications), targeting ligands, and/or linkers described above, or any of the specific structures or chemistries shown in the summary or Examples.

Example 7 provides an example methodology for preparing various oligonucleotide precursors useful in the syntheses above. Example 8 provides an example methodology for preparing various oligonucleotide multimers, which are also useful in the syntheses above.

In various embodiments, R1, R2, and the bifunctional linking moiety o can form a covalent linker • as described and shown herein. For example, in various embodiments, R1 and R2 can each independently comprise a reactive moiety, for example an electrophile or nucleophile. In one embodiment, R1 and R2 can each independently be selected from the group consisting of a thiol, maleimide, vinylsulfone, pyridyldisulfide, iodoacetamide, acrylate, azide, alkyne, amine, and carboxyl group. In various embodiments, the bifunctional linking moiety o comprises two reactive moieties that can be sequentially reacted according to steps (i) and (ii) above, for example a second electrophile/nucleophile that can be reacted with an electrophile/nucleophile in R1 and R2. Examples of bifunctional linking moieties o include, but are not limited to, DTME, BM(PEG)2, BM(PEG)3, BMOE, BMH, or BMB.

In various embodiments comprising two or more covalent linkers • (e.g., in Structures 7-16), the linkers are all the same. Alternatively, the compound or composition can comprise two or more different covalent linkers •.

In various embodiments, each ──•── may independently comprise two sense or two antisense oligonucleotides. For example, in the case of siRNA, a ──•── may comprise two active strands or two passenger strands.

In various embodiments, each ──•── may independently comprise one sense and one antisense oligonucleotide. For example, in the case of siRNA, a ──•── may comprise one active strand and one passenger strand.

In various embodiments, the compound or composition comprises a homomultimer of substantially identical double stranded oligonucleotides. The substantially identical double stranded oligonucleotides can each comprise an siRNA targeting the same molecular target in vivo.

In various embodiments, the compound or composition comprises a hetero-multimer of two or more substantially different double stranded oligonucleotides. The substantially different double stranded oligonucleotides can each comprise an siRNA targeting different genes.

In various embodiments, the compound comprises Structure 9 and n=0: ═•═•═ (Structure 9). The compound can further comprise a targeting ligand. The compound can further comprise 2 or 3 substantially different double stranded oligonucleotides ═══ each comprising an siRNA targeting a different molecular target in vivo. The compound can further comprise a targeting ligand, one ═══ comprising a first siRNA guide strand targeting Factor VII and a first passenger strand hybridized to the guide strand, one ═══ comprising a second siRNA guide strand targeting Apolipoprotein B and a second passenger strand hybridized to the second guide strand, and one ═══ comprising a third siRNA guide strand targeting TTR and a third passenger strand hybridized to the third guide strand. The targeting ligand can comprise N-Acetyl-galactosamine (GalNAc).

Examples of Trimers are Provided in Examples 17, 18, and 20.

In various embodiments, the compound comprises Structure 10 and m=1: ═•═•═•═ (Structure 10). The compound can further comprise a targeting ligand. The compound can further comprise 2, 3, or 4 substantially different double stranded oligonucleotides ═══ each comprising an siRNA targeting a different molecular target in vivo. The compound can further comprise a targeting ligand, one ═══ comprising a first siRNA guide strand targeting Factor VII and a first passenger strand hybridized to the guide strand, one ══ comprising a second siRNA guide strand targeting Apolipoprotein B and a second passenger strand hybridized to the second guide strand, and one ══ comprising a third siRNA guide strand targeting TTR and a third passenger strand hybridized to the third guide strand. The targeting ligand can comprise N-Acetylgalactosamine (GalNAc).

Examples of Tetramers are Provided in Example 21.

In various embodiments, each double stranded oligonucleotide (e.g., ══ for example in Structure 4) comprises an siRNA guide strand targeting Factor VII and a passenger strand hybridized to the guide strand.

In various embodiments (e.g., in Structure 4), the compound further comprises a targeting ligand, each double stranded oligonucleotide (e.g., ══ ) comprises an siRNA guide strand and a passenger strand hybridized to the guide strand, and the compound is at least 75, 80, 85, 90, 95, 96, 97, 98, 99, or 100% pure.

In various embodiments, at least one double stranded oligonucleotide (e.g., ══ , for example in Structure 6) comprises a first siRNA guide strand targeting Factor VII and a first passenger strand hybridized to the guide strand, and at least one double stranded oligonucleotide (e.g., ∞∞∞, for example in Structure 6) comprises a second siRNA guide strand targeting Apolipoprotein B and a second passenger strand hybridized the second guide strand.

Sense-Antisense Multimeric Compounds

In various aspects, the invention provides sense-antisense multi-conjugate oligonucleotides, as well as methods for their synthesis.

In one aspect, the invention provides a composition comprising a plurality of molecules, each molecule having Structure 16:

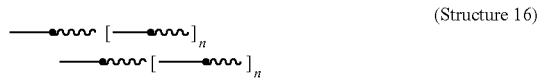

(Structure 16)

wherein n is an integer ≥1;
each ───── a single stranded oligonucleotide;
each ∿∿∿∿ is a single stranded oligonucleotide that hybridizes with a ───── ;
══ is a double stranded oligonucleotide; and
each • is a covalent linker joining single strands of adjacent single stranded oligonucleotides.

Similarly, the invention provides a method for synthesizing composition comprising a plurality of molecules, each molecule having Structure 16, the methods comprising:
(i) reacting a first single stranded oligonucleotide ─────R₁ with a bifunctional linking moiety ○, wherein R1 is a chemical group capable of reacting with ○ under conditions that produce the mono-substituted product ─────○ ; ;
(ii) reacting ─────○ with a second single stranded oligonucleotide ∿∿∿R₂, wherein R2 is a chemical group capable of reacting with ○, thereby forming ─────•∿∿∿ ; and
(iii) annealing a plurality of 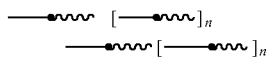 , thereby forming a composition comprising a plurality of molecules, each molecule having Structure 16.

As with the other compounds and compositions according to the invention, molecules according to Structure 16 can include any one or more of the features described herein, including in the Examples. For example, the compounds can include any one or more of the nucleic acids (with or without modifications), targeting ligands, and/or linkers described above, or any of the specific structures or chemistries shown in the summary or Examples.

For example, in various embodiments, each ══ has a length of 15-30 base pairs; each ══ is an siRNA; and/or n is an integer from 1 to 100. Although specific examples of Structure 16 are shown as siRNA, the structure is not necessarily limited to siRNA.

In various embodiments, R1, R2, and the bifunctional linking moiety ○ can form a covalent linker • as described and shown herein. For example, in various embodiments, R1 and R2 can each independently comprise a reactive moiety, for example an electrophile or nucleophile. In one embodiment, R1 and R2 can each independently be selected from the group consisting of a thiol, maleimide, vinylsulfone, pyridyldisulfide, iodoacetamide, acrylate, azide, alkyne, amine, and carboxyl group. In various embodiments, the bifunctional linking moiety ○ comprises two reactive moieties that can be sequentially reacted according to steps (i) and (ii) above, for example a second electrophile/nucleophile that can be reacted with an electrophile/nucleophile in R1 and R2. Examples of bifunctional linking moieties ○ include, but are not limited to, DTME, BM(PEG)2, BM(PEG)3, BMOE, BMH, or BMB.

In one embodiment, each double stranded oligonucleotide has essentially the same sequence. In other embodiments, the double stranded oligonucleotides may vary. For example, each ───── can be an siRNA active strand with the same target, and each ∿∿∿∿ can be an siRNA passenger strand that is at least about 80, 85, 90, or 95% complementary to ───── (e.g., the sequence of ∿∿∿∿ can vary as long as it hybridizes with ───── ).

Annealing Conditions for Multimeric Compounds

In various aspects, the invention provides methods for synthesizing multi-conjugate oligonucleotides.

In one aspect, the invention provides method for synthesizing a composition comprising a plurality of molecule comprising Structure 17:

─────•∿∿∿ [─────•∿∿∿]ₙ
─────•∿∿∿ [─────•∿∿∿]ₙ

(Structure 17), wherein n is an integer ≥1; ───── each is a single stranded oligonucleotide; each ∿∿∿∿ is a single stranded oligonucleotide that hybridizes with a ───── ; ══ is a double stranded oligonucleotide; and each • is a covalent linker joining single strands of adjacent single stranded oligonucleotides to form ─────•───── and ∿∿∿•∿∿∿, the method comprising the steps of:

annealing a plurality of ─────•───── and ∿∿∿•∿∿∿ at:
(i) a total oligonucleotide concentration of about 200-300 μM for ─────•───── and ∿∿∿•∿∿∿,
(ii) about 0.1-0.3× phosphate buffered saline (PBS), and
(iii) at a temperature of about 70-80° C. to about 20-30° C. for about 1.5-2.5 hours.

In various embodiments, the method further comprises the step of annealing a plurality of ───── and/or ∿∿∿∿ thereby forming a plurality of molecules comprising Structure 18:

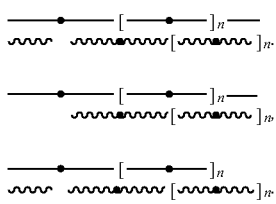

(Structure 18)

(Structure 19)

(Structure 20)

In various embodiments, the method further comprises annealing ――――― with the plurality of plurality of ――•― and ⁓⁓•⁓.

In various embodiments, the molar ratio of ――――― to ⁓⁓•⁓ is about 5:100, 10:100, 20:100, 30:100, 40:100, or 50:100.

In various embodiments, the method further comprises annealing see ⁓⁓⁓ with the plurality of plurality of ――•― and ⁓⁓•⁓.

In various embodiments, the molar ratio of ⁓⁓⁓ to ⁓⁓•⁓ is about 5:100, 10:100, 20:100, 30:100, 40:100, or 50:100.

In various embodiments, the molar ratio of ――•― and ⁓⁓•⁓ is about 1:1.

In various embodiments, the molar ratio of ――•― to ⁓⁓•⁓ or the molar ratio of ⁓⁓•⁓ to ――•― is about 100:90, 100:80, 100:75, 100:70, or 100:60.

In various embodiments, each ⁓ has a length of 15-30 base pairs.

In various embodiments, each ⁓ is an siRNA.

In various embodiments, each ⁓ comprises siRNA guide strand targeting Factor VII and a passenger strand hybridized to the guide strand.

In various embodiments, n is an integer from 1 to 100.

In various embodiments, • is a cleavable or non-cleavable linker.

In various embodiments, the method further comprises formulating the plurality of molecules comprising Structure 17, 18, 19, and/or 20 in a nanoparticle.

As with the other compounds and compositions according to the invention, multimeric compounds and intermediates can include any one or more of the features described herein (including methods steps and including in the Examples). For example, the compounds can include any one or more of the nucleic acids (with or without modifications), targeting ligands, and/or linkers described above, or any of the specific structures or chemistries shown in the summary or Examples. Examples 22-24 illustrate exemplary embodiments of multimeric oligonucleotides.

Pharmaceutical Compositions

In various aspects, the invention provides pharmaceutical compositions including any one or more of the compounds or compositions described above. As used herein, pharmaceutical compositions include compositions of matter, other than foods, that can be used to prevent, diagnose, alleviate, treat, or cure a disease. Similarly, the various compounds or compositions according to the invention should be understood as including embodiments for use as a medicament and/or for use in the manufacture of a medicament.

A pharmaceutical composition can include a compound or composition according to the invention and a pharmaceutically acceptable excipient. As used herein, an excipient can be a natural or synthetic substance formulated alongside the active ingredient. Excipients can be included for the purpose of long-term stabilization, increasing volume (e.g., bulking agents, fillers, or diluents), or to confer a therapeutic enhancement on the active ingredient in the final dosage form, such as facilitating drug absorption, reducing viscosity, or enhancing solubility. Excipients can also be useful manufacturing and distribution, for example, to aid in the handling of the active ingredient and/or to aid in vitro stability (e.g., by preventing denaturation or aggregation). As will be understood by those skilled in the art, appropriate excipient selection can depend upon various factors, including the route of administration, dosage form, and active ingredient(s).

Oligonucleotides can be delivered locally or systemically, and the pharmaceutical compositions of the invention can vary accordingly. For example, administration is not necessarily limited to any particular delivery system and may include, without limitation, parenteral (including subcutaneous, intravenous, intramedullary, intraarticular, intramuscular, or intraperitoneal injection), rectal, topical, transdermal, or oral. Administration to an individual may occur in a single dose or in repeat administrations, and in any of a variety of physiologically acceptable salt forms, and/or with an acceptable pharmaceutical carrier and/or additive as part of a pharmaceutical composition. Physiologically acceptable formulations and standard pharmaceutical formulation techniques, dosages, and excipients are well known to persons skilled in the art (see, e.g., Physicians' Desk Reference (PDR®) 2005, 59$^{th}$ ed., Medical Economics Company, 2004; and Remington: The Science and Practice of Pharmacy, eds. Gennado et al. 21$^{th}$ ed., Lippincott, Williams & Wilkins, 2005).

Pharmaceutical compositions can include an effective amount of the compound or composition according to the invention. As used herein, effective amount can be a concentration or amount that results in achieving a particular stated purpose, or more amount means an amount adequate to cause a change, for example in comparison to a placebo. Where the effective amount is a therapeutically effective amount, it can be an amount adequate for therapeutic use, for example and amount sufficient to prevent, diagnose, alleviate, treat, or cure a disease. An effective amount can be determined by methods known in the art. An effective amount can be determined empirically, for example by human clinical trials. Effective amounts can also be extrapolated from one animal (e.g., mouse, rat, monkey, pig, dog) for use in another animal (e.g., human), using conversion factors known in the art. See, e.g., Freireich et al., Cancer Chemother Reports 50(4):219-244 (1966).

Delivery Vehicles and Targeting Ligands

In various aspects, the invention provides any one or more of the compounds or compositions described above formulated in a delivery vehicle. For example, the delivery vehicle can be a lipid nanoparticle (LNP), exosome, microvesicle, or viral vector. Similarly, in various aspects, the invention provides any one or more of the compounds or compositions described above and further comprising a targeting ligand. For example, the targeting ligand comprises N-Acetylgalactosamine (GalNAc), cholesterol, tocopherol, folate, 2-[3-(1, 3-dicarboxypropyl)-ureido]pentanedioic acid (DUPA), or anisamide. The targeting ligand can be bound (e.g., directly) to the nucleic acid, for example through its 3' or 5' terminus. Additional examples that may be adapted for use with the invention are discussed below.

As will be understood by those skilled in the art, regardless of biological target or mechanism of action, therapeutic oligonucleotides must overcome a series of physiological hurdles to access the target cell in an organism (e.g., animal, such as a human, in need of therapy). For example, a therapeutic oligonucleotide generally must avoid clearance in the bloodstream, enter the target cell type, and then enter the cytoplasm, all without eliciting an undesirable immune response. This process is generally considered inefficient, for example, 95% or more of siRNA that enters the endosome in vivo may be degraded in lysosomes or pushed out of the cell without affecting any gene silencing.

To overcome these obstacles, scientists have designed numerous drug delivery vehicles. These vehicles have been used to deliver therapeutic RNAs in addition to small molecule drugs, protein drugs, and other therapeutic molecules. Drug delivery vehicles have been made from materials as diverse as sugars, lipids, lipid-like materials, proteins, polymers, peptides, metals, hydrogels, conjugates, and peptides. Many drug delivery vehicles incorporate aspects from combinations of these groups, for example, some drug delivery vehicle can combine sugars and lipids. In some other examples, drugs can be directly hidden in 'cell like' materials that are meant to mimic cells, while in other cases, drugs can be put into, or onto, cells themselves. Drug delivery vehicles can be designed to release drugs in response to stimuli such as pH change, biomolecule concentration, magnetic fields, and heat.

Much work has focused on delivering oligonucleotides such as siRNA to the liver. The dose required for effective siRNA delivery to hepatocytes in vivo has decreased by more than 10,000 fold in the last ten years—whereas delivery vehicles reported in 2006 could require more than 10 mg/kg siRNA to target protein production, new delivery vehicles target protein production can now be reduced after a systemic injection of 0.001 mg/kg siRNA. The increase in oligonucleotide delivery efficiency can be attributed, at least in part, to developments in delivery vehicles.

Another important advance has been an increased understanding of the way helper components influence delivery. Helper components can include chemical structures added to the primary drug delivery system. Often, helper components can improve particle stability or delivery to a specific organ. For example, nanoparticles can be made of lipids, but the delivery mediated by these lipid nanoparticles can be affected by the presence of hydrophilic polymers and/or hydrophobic molecules. One important hydrophilic polymer that influences nanoparticle delivery is poly(ethylene glycol). Other hydrophilic polymers include non-ionic surfactants. Hydrophobic molecules that affect nanoparticle delivery include cholesterol, 1-2-Distearoyl-sn-glyerco-3-phosphocholine (DSPC), 1-2-di-O-octadecenyl-3-trimethylammonium propane (DOTMA), 1,2-dioleoyl-3-trimethylammonium-propane (DOTAP), and others.

Drug delivery systems have also been designed using targeting ligands or conjugate systems. For example, oligonucleotides can be conjugated to cholesterols, sugars, peptides, and other nucleic acids, to facilitate delivery into hepatocytes and/or other cell types.

One skilled in the art will appreciate that known delivery vehicles and targeting ligands can generally be adapted for use according to the present invention. Examples of delivery vehicles and targeting ligands, as well as their use, can be found in: Sahay, G., et al. Efficiency of siRNA delivery by lipid nanoparticles is limited by endocytic recycling. Nat Biotechnol, 31:653-658 (2013); Wittrup, A., et al. Visualizing lipid-formulated siRNA release from endosomes and target gene knockdown. Nat Biotechnol (2015); Whitehead, K. A., Langer, R. & Anderson, D. G. Knocking down barriers: advances in siRNA delivery. Nature reviews. Drug Discovery, 8:129-138 (2009); Kanasty, R., Dorkin, J. R., Vegas, A. & Anderson, D. Delivery materials for siRNA therapeutics. Nature Materials, 12:967-977 (2013); Tibbitt, M. W., Dahlman, J. E. & Langer, R. Emerging Frontiers in Drug Delivery. J Am Chem Soc, 138:704-717 (2016); Akinc, A., et al. Targeted delivery of RNAi therapeutics with endogenous and exogenous ligand-based mechanisms. Molecular therapy: the journal of the American Society of Gene Therapy 18, 1357-1364 (2010); Nair, J. K., et al. Multivalent N-acetylgalactosamine-conjugated siRNA localizes in hepatocytes and elicits robust RNAimediated gene silencing. J Am Chem Soc, 136:16958-16961 (2014); Ostergaard, M. E., et al. Efficient Synthesis and Biological Evaluation of 5'-GalNAc Conjugated Antisense Oligonucleotides. Bioconjugate chemistry (2015); Sehgal, A., et al. An RNAi therapeutic targeting antithrombin to rebalance the coagulation system and promote hemostasis in hemophilia. Nature Medicine, 21:492-497 (2015); Semple, S. C., et al. Rational design of cationic lipids for siRNA delivery. Nat Biotechnol, 28:172-176 (2010); Maier, M. A., et al. Biodegradable lipids enabling rapidly eliminated lipid nanoparticles for systemic delivery of RNAi therapeutics. Molecular therapy: the journal of the American Society of Gene Therapy, 21:1570-1578 (2013); Love, K. T., et al. Lipid-like materials for low-dose, in vivo gene silencing. Proc Nat Acad USA, 107:1864-1869 (2010); Akinc, A., et al. A combinat01ial library of lipid-like materials for delivery of RNAi therapeutics. Nat Biotechnol, 26:561-569 (2008); Eguchi, A., et al. Efficient siRNA delivery into primary cells by a peptide transduction domain-dsRNA binding domain fusion protein. Nat Biotechnol, 27:567-571 (2009); Zuckerman, J. E., et al. Correlating animal and human phase Ia/Ib clinical data with CALAA-01, a targeted, polymer-based nanoparticle containing siRNA. Proc Nat Acad USA, 111: 11449-11454 (2014); Zuckerman, J. E. & Davis, M. E. Clinical experiences with systemically administered siRNA-based therapeutics in cancer. Nature Reviews. Drug Discovery, 14:843-856 (2015); Hao, J., et al. Rapid Synthesis of a Lipocationic Polyester Library via RingOpening Pol ymelization of Functional V alerolactones for Efficacious siRN A Deli very. J Am Chem Soc, 29:9206-9209 (2015); Siegwart, D. J., et al. Combinatorial synthesis of chemically diverse core-shell nanoparticles for intracellular delivery. Proc Nat Acad USA, 108:12996-13001 (2011); Dahlman, J. E., et al. In vivo endothelial siRNA delivery using polymeric nanoparticles with low molecular weight. Nat Nano 9, 648-655 (2014); Soppimath, K. S., Aminabhavi, T. M., Kulkarni, A. R. & Rudzinski, W. E. Biodegradable polymeric nanoparticles as drug delivery devices. Journal of controlled release: official journal of the Controlled Release Society 70, 1-20 (2001); Kim, H. J., et al. Precise engineering of siRNA delivery vehicles to tumors using polyion complexes and gold nanoparticles. ACS Nano, 8:8979-8991 (2014); Krebs, M. D., Jeon, O. & Alsberg, E. Localized and sustained delivery of silencing RNA from macroscopic biopolymer hydrogels. J Am Chem Soc 131, 9204-9206 (2009); Zimmermann, T. S., et al. RNAi-mediated gene silencing in non-human primates. Nature, 441:111-114 (2006); Dong, Y., et al. Lipopeptide nanoparticles for potent and selective siRNA delivery in rodents and nonhuman primates. Proc Nat Acad USA, 111:3955-3960 (2014); Zhang, Y., et al. Lipid-modified aminoglycoside derivatives for in vivo siRNA delivery. Advanced Materials, 25:4641-4645 (2013); Molinaro, R., et al. Biomimetic proteolipid vesicles for targeting inflamed tissues. Nat Mater (2016); Hu, C. M., et al. Nanoparticle biointerfacing by platelet membrane cloaking. Nature, 526:118-121 (2015); Cheng, R., Meng, F., Deng, C., Klok, H.-A. & Zhong, Z. Dual and multi-stimuli responsive polymeric nanoparticles for programmed site-specific drug delivery. Biomaterials, 34:3647-3657 (2013);

Qiu, Y. & Park, K. Environment-sensitive hydrogels for drug delivery. Advanced Drug Delivery Reviews, 64, Supplement, 49-60 (2012); Mui, B. L., et al. Influence of Polyethylene Glycol Lipid Desorption Rates on Pharmacokinetics and Pharmacodynamics of siRNA Lipid Nanoparticles. Mol Ther Nucleic Acids 2, e139 (2013); Draz, M. S., et al. Nanoparticle-Mediated Systemic Delivery of siRNA for Treatment of Cancers and Viral Infections. Theranostics, 4:872-892 (2014); Otsuka, H., Nagasaki, Y. & Kataoka, K. PEGylated nanoparticles for biological and pharmaceutical applications. Advanced Drug Delivery Reviews, 55:403-419 (2003); Kauffman, K. J., et al. Optimization of Lipid Nanoparticle Formulations for mRNA Delivery in vivo with Fractional Factorial and Definitive Screening Designs. Nano Letters, 15:7300-7306 (2015); Zhang, S., Zhao, B., Jiang, H., Wang, B. & Ma, B. Cationic lipids and polymers mediated vectors for delivery of siRNA. Journal of Controlled Release 123, 1-10 (2007); Illum, L. & Davis, S. S. The organ uptake of intravenously administered colloidal particles can be altered using a non-ionic surfactant (Poloxamer 338). FEBS Letters, 167:79-82 (1984); Feigner, P. L., et al. Improved Cationic Lipid Formulations for In vivo Gene Therapy. Annals of the New York Academy of Sciences, 772:126-139 (1995); Meade, B. R. & Dowdy, S. F. Exogenous siRNA delivery using peptide transduction domains/cell penetrating peptides. Advanced Drug Delivery Reviews, 59:134-140 (2007); Endoh, T. & Ohtsuki, T. Cellular siRNA delivery using cell-penetrating peptides modified for endosomal escape. Advanced Drug Delivery Reviews, 61:704-709 (2009); and Lee, H., et al. Molecularly self-assembled nucleic acid nanoparticles for targeted in vivo siRNA delivery. Nat Nano, 7:389-393 (2012).

In various embodiments, the compounds and compositions of the invention can be conjugated to or delivered with other chemical or biological moieties, including, e.g., biologically active moieties. A biologically active moiety is any molecule or agent that has a biological effect, preferably a measurable biological effect. Chemical or biological moieties include, e.g., proteins, peptides, amino acids, nucleic acids (including, e.g., DNA, RNA of all types, RNA and DNA aptamers, antisense oligonucleotides, and antisense miRNA inhibitors), targeting ligands, carbohydrates, polysaccharides, lipids, organic compounds, and inorganic chemical compounds.

As used herein, the term targeting ligand can include a moiety that can be made accessible on the surface of a nanoparticle or as part of a delivery conjugate for the purpose of delivering the payload of the nanoparticle or delivery conjugate to a specific target, such as a specific bodily tissue or cell type, for example, by enabling cell receptor attachment of the nanoparticle or delivery conjugate. Examples of suitable targeting ligands include, but are not limited to, cell specific peptides or proteins (e.g., transferrin and monoclonal antibodies), aptamers, cell growth factors, vitamins (e.g., folic acid), monosaccharides (e.g., galactose and mannose), polysaccharides, arginine-glycine-aspartic acid (RGD), and asialoglycoprotein receptor ligands derived from N-acetylgalactosamine (GalNac). The ligand may be incorporated into the foregoing compounds of the invention using a variety of techniques known in the art, such as via a covalent bond such as a disulfide bond, an amide bond, or an ester bond, or via a non-covalent bond such as biotin-streptavidin, or a metal-ligand complex. Additional biologically active moieties within the scope of the invention are any of the known gene editing materials, including for example, materials such as oligonucleotides, polypeptides and proteins involved in CRISPR/Cas systems, Tales, Talens, and zinc fingers.

In various embodiments, the compounds and compositions of the invention can be encapsulated in a carrier material to form nanoparticles for intracellular delivery. Known carrier materials include cationic polymers, lipids or peptides, or chemical analogs thereof. Jeong et al., BIOCONJUGATE CHEM., Vol. 20, No. 1, pp. 5-14 (2009). Examples of a cationic lipid include dioleyl phosphatidylethanolamine, cholesterol dioleyl phosphatidylcholine, N-[1-(2,3-dioleoyloxy)propyl]-N,N,N-trimethylammonium chloride (DOTMA), 1,2-dioleoyloxy-3-(trimethylammonio) propane (DOTAP), 1,2-dioleoyl-3-(4'-trimethyl-ammonio) butanoyl-sn-glycerol (DOTB), 1,2-diacyl-3-dimethylammonium-propane (DAP), 1,2-diacyl-3-trimethylammonium-propane (TAP), 1,2-diacyl-sn-glycerol-3-ethylphosphocholin, 3 beta-[N—(N',N'-dimethylaminoethane)-carbamoyl]cholesterol (DCCholesterol), dimethyldioctadecylammonium bromide (DDAB), and copolymers thereof. Examples of a cationic polymer include polyethyleneimine, polyamine, polyvinylamine, poly(alkylamine hydrochloride), polyamidoamine dendrimer, diethylaminoethyl-dextran, polyvinylpyrrolidone, chitin, chitosan, and poly(2-dimethylamino)ethyl methacrylate. In one embodiment, the carrier contains one or more acylated amines, the properties of which may be better suited for use in vivo as compared to other known carrier materials.

In one embodiment, the carrier is a cationic peptide, for example KALA (a cationic fusogenic peptide), polylysine, polyglutamic acid or protamine. In one embodiment, the carrier is a cationic lipid, for example dioleyl phosphatidylethanolamine or cholesterol dioleyl phosphatidylcholine. In one embodiment, the carrier is a cationic polymer, for example polyethyleneimine, polyamine, or polyvinylamine.

In various embodiments, the compounds and compositions of the invention can be encapsulated in exosomes. Exosomes are cell-derived vesicles having diameters between 30 and 100 nm that are present in biological fluids, including blood, urine, and cultured medium of cell cultures. Exosomes, including synthetic exsosomes and exosome mimetics can be adapted for use in drug delivery according to the skill in the art. See, e.g., "A comprehensive overview of exosomes as drug delivery vehicles—endogenous nanocarriers for targeted cancer therapy" Biochim Biophys Acta. 1846(1):75-87 (2014); "Exosomes as therapeutic drug carriers and delivery vehicles across biological membranes: current perspectives and future challenges" Acta Pharmaceutica Sinica B, Available online 8 Mar. 2016 (In Press); and "Exosome mimetics: a novel class of drug delivery systems" International Journal of Nanomedicine, 7:1525-1541 (2012).

In various embodiments, the compounds and compositions of the invention can be encapsulated in microvesicles. Microvesicles (sometimes called, circulating microvesicles, or microparticles.) are fragments of plasma membrane ranging from 100 nm to 1000 nm shed from almost all cell types and are distinct from smaller intracellularly generated extracellular vesicles known as exosomes. Microvesicles play a role in intercellular communication and can transport mRNA, miRNA, and proteins between cells. Microvesicles, including synthetic microvesicles and microvesicle mimetics can be adapted for use in drug delivery according to the skill in the art. See, e.g., "Microvesicle- and exosome-mediated drug delivery enhances the cytotoxicity of Paclitaxel in autologous prostate cancer cells" Journal of Controlled Release, 220:727-737 (2015); "Therapeutic Uses of Exosomes" J Circ Biomark, 1:0 (2013).

In various embodiments, the compounds and compositions of the invention can be delivered using a viral vector. Viral vectors are tools commonly used by molecular biologists to deliver genetic material into cells. This process can be performed inside a living organism (in vivo) or in cell culture (in vitro). Viral vectors can be adapted for use in drug delivery according to the skill in the art. See, e.g., "Viruses as nanomaterials for drug delivery" Methods Mol Biol, 26:207-21 (2011); "Viral and nonviral delivery systems for gene delivery" Adv Biomed Res, 1:27 (2012); and "Biological Gene Delivery Vehicles: Beyond Viral Vectors" Molecular Therapy, 17(5):767-777 (2009).

General procedures for LNP formulation and characterization are provided in the Examples below, as are working examples of LNP formulations and other in vitro and in vivo tests. Other methods are known in the art and can be adapted for use with the present invention by those of ordinary skill.

Methods of Treatment, Reducing Gene Expression

In various aspects, the invention provides methods for using multi-conjugate oligonucleotides, for example for medical treatments, research, or for producing new or altered phenotypes in animals and plants.

In one aspect, the invention provides a method for treating a subject comprising administering an effective amount of a compound or composition according to the invention to a subject in need thereof. In such therapeutic embodiments, the oligonucleotide will be a therapeutic oligonucleotide, for example an siRNA or miRNA.

In this, and other embodiments, the compositions and compounds of the invention can be administered in the form of a pharmaceutical composition, in a delivery vehicle, or coupled to a targeting ligand.

In one aspect, the invention provides a method for silencing or reducing gene expression comprising administering an effective amount of a compound or composition according to the invention to a subject in need thereof. In such therapeutic embodiments, the oligonucleotide will be a oligonucleotide that silences or reduces gene expression, for example an siRNA or antisense oligonucleotide.

Similarly, the invention provides a method for silencing or reducing expression of two or more genes comprising administering an effective amount of a compound or composition according to the invention to a subject in need thereof, wherein the compound or composition comprises oligonucleotides targeting two or more genes. The compound or composition can comprise oligonucleotides targeting two, three, four, or more genes.

In one aspect, the invention provides a method for delivering two or more oligonucleotides to a cell per targeting ligand binding event comprising administering an effective amount of a compound or composition according to the invention to a subject in need thereof, wherein the compound or composition comprises a targeting ligand.

In one aspect, the invention provides a method for delivering a predetermined stoichiometric ratio of two or more oligonucleotides to a cell comprising administering an effective amount of a compound or composition according to the invention to a subject in need thereof, wherein the compound or composition comprises the predetermined stoichiometric ratio of two or more oligonucleotides.

As used herein, subject includes a cell or organism subject to the treatment or administration. The subject can be an animal, for example a mammal such as a laboratory animal (mouse, monkey) or veterinary patient, or a primate such as a human. Without limitation, a subject in need of the treatment or administration can include a subject having a disease (e.g., that may be treated using the compounds and compositions of the invention) or a subject having a condition (e.g., that may be addressed using the compounds and compositions of the invention, for example one or more genes to be silenced or have expression reduced).

General procedures for measurement of gene knockdown and animal experiments are provided in the Examples below, as are working example of other in vitro and in vivo tests. Other methods are known in the art and can be adapted for use with the present invention by those of ordinary skill.

The following examples are illustrative and not restrictive. Many variations of the technology will become apparent to those of skill in the art upon review of this disclosure. The scope of the technology should, therefore, be determined not with reference to the examples, but instead should be determined with reference to the appended claims along with their full scope of equivalents.

EXAMPLES

General Procedure: Single Chain Oligonucleotide Synthesis

Oligoribonucleotides were assembled on ABI 394 and 3900 synthesizers (Applied Biosystems) at the 10 μmol scale, or on an Oligopilot 10 synthesizer at 28 μmol scale, using phosphoramidite chemistry. Solid supports were polystyrene loaded with 2'-deoxythymidine (Glen Research, Sterling, Virginia, USA), or controlled pore glass (CPG, 520 Å, with a loading of 75 μmol/g, obtained from Prime Synthesis, Aston, PA, USA). Ancillary synthesis reagents, DNA-, 2'-O-Methyl RNA-, and 2'-deoxy-2'-fluoro-RNA phosphoramidites were obtained from SAFC Proligo (Hamburg, Germany). Specifically, 5'-O-(4,4'-dimethoxytrityl)-3'-O-(2-cyanoethyl-N,N-diisopropyl) phosphoramidite monomers of 2'-O-methyl-uridine (2'-OMe-U), 4-N-acetyl-2'-O-methyl-cytidine (2'-OMe-$C^{Ac}$), 6-N-benzoyl-2'-O-methyl-adenosine (2'-OMe-$A^{bz}$) and 2-N-isobutyrlguanosine (2'-OMe-$G^{iBu}$) were used to build the oligomer sequences. 2'-Fluoro modifications were introduced employing the corresponding phosphoramidites carrying the same nucleobase protecting groups as the 2'-OMe RNA building blocks. Coupling time for all phosphoramidites (70 mM in Acetonitrile) was 3 min employing 5-Ethylthio-1H-tetrazole (ETT, 0.5 Min Acetonitrile) as activator. Phosphorothioate linkages were introduced using 50 mM 3-((Dimethylaminomethylidene)amino)-3H-1,2,4-dithiazole-3-thione (DDTT, AM Chemicals, Oceanside, California, USA) in a 1:1 (v/v) mixture of pyridine and Acetonitrile. Upon completion of the solid phase synthesis including removal of the DMT group ("DMT off synthesis") oligonucleotides were cleaved from the solid support and deprotected using a 1:1 mixture consisting of aqueous methylamine (41%) and concentrated aqueous ammonia (32%) for 3 hours at 25° C. according to published methods (Wincott, F. et al: Synthesis, deprotection, analysis and purification of RNA and ribozymes. Nucleic Acids Res, 23:2677-2684 (1995).

Subsequently, crude oligomers were purified by anionic exchange HPLC using a column packed with Source Q15 (GE Healthcare) and an AKTA Explorer system (GE Healthcare). Buffer A was 10 mM sodium perchlorate, 20 mM Tris, 1 mM EDTA, pH 7.4 (Fluka, Buchs, Switzerland) in 20% aqueous Acetonitrile and buffer B was the same as buffer A with 500 mM sodium perchlorate. A gradient of 22% B to 42% B within 32 column volumes (CV) was employed. UV traces at 280 nm were recorded. Appropriate fractions were pooled and precipitated with 3M NaOAc, pH=5.2 and 70% Ethanol. Pellets were collected by centrifugation. Alternatively, desalting was carried out using Sephadex HiPrep columns (GE Healthcare) according to the manufacturer's recommendations.

Oligonucleotides were reconstituted in water and identity of the oligonucleotides was confirmed by electrospray ionization mass spectrometry (ESI-MS). Purity was assessed by analytical anion-exchange HPLC.

General Procedure: Lipid Nanoparticle Formulation 1,2-distearoyl-3-phosphatidylcholine (DSPC) was purchased from Avanti Polar Lipids (Alabaster, Alabama, USA). α-[3'-(1,2-dimyristoyl-3-propanoxy)-carboxamide-propyl]-ω-methoxy-polyoxyethylene (PEG-c-DOMG) was obtained from NOF (Bouwelven, Belgium). Cholesterol was purchased from Sigma-Aldrich (Taufkirchen, Germany).

The proprietary aminolipids KL22 and KL52 are disclosed in the patent literature (Constien et al. "Novel Lipids and Compositions for Intracellular Delivery of Biologically Active Compounds" US 2012/0295832 A1). Stock solutions of KL52 and KL22 lipids, DSPC, cholesterol, and PEG-c-DOMG were prepared at concentrations of 50 mM in ethanol and stored at −20° C. The lipids were combined to yield various molar ratios (see individual examples below) and diluted with ethanol to a final lipid concentration of 25 mM. siRNA stock solutions at a concentration of 10 mg/mL in $H_2O$ were diluted in 50 mM sodium citrate buffer, pH 3. KL22 and KL52 are sometimes referred to as XL 7 and XL 10, respectively, in the examples that follow.

The lipid nanoparticle (LNP) formulations were prepared by combining the lipid solution with the siRNA solution at total lipid to siRNA weight ratio of 7:1. The lipid ethanolic solution was rapidly injected into the aqueous siRNA solution to afford a suspension containing 33% ethanol. The solutions were injected by the aid of a syringe pump (Harvard Pump 33 Dual Syringe Pump Harvard Apparatus Holliston, MA).

Subsequently, the formulations were dialyzed 2 times against phosphate buffered saline (PBS), pH 7.4 at volumes 200-times that of the primary product using a Slide-A-Lyzer cassettes (Thermo Fisher Scientific Inc. Rockford, IL) with a MWCO of 10 kD (RC membrane) to remove ethanol and achieve buffer exchange. The first dialysis was carried out at room temperature for 3 hours and then the formulations were dialyzed overnight at 4° C. The resulting nanoparticle suspension was filtered through 0.2 µm sterile filter (Sarstedt, Nimbrecht, Germany) into glass vials and sealed with a crimp closure.

General Procedure: LNP Characterization

Particle size and zeta potential of formulations were determined using a Zetasizer Nano ZS (Malvern Instruments Ltd, Malvern, Worcestershire, UK) in 1×PBS and 15 mM PBS, respectively.

The siRNA concentration in the liposomal formulation was measured by UV-vis. Briefly, 100 µL of the diluted formulation in 1×PBS was added to 900 µL of a 4:1 (v/v) mixture of methanol and chloroform. After mixing, the absorbance spectrum of the solution was recorded between 230 nm and 330 nm on a DU 800 spectrophotometer (Beckman Coulter, Beckman Coulter, Inc., Brea, CA). The siRNA concentration in the liposomal formulation was calculated based on the extinction coefficient of the siRNA used in the formulation and on the difference between the absorbance at a wavelength of 260 nm and the baseline value at a wavelength of 330 nm.

Encapsulation of siRNA by the nanoparticles was evaluated by the Quant-iT™ RiboGreen® RNA assay (Invitrogen Corporation Carlsbad, CA). Briefly, the samples were diluted to a concentration of approximately 5 µg/mL in TE buffer (10 mM Tris-HCl, 1 mM EDTA, pH 7.5). 50 µL of the diluted samples were transferred to a polystyrene 96 well plate, then either 50 µL of TE buffer or 50 µL of a 2% Triton X-100 solution was added. The plate was incubated at a temperature of 37° C. for 15 minutes. The RiboGreen reagent was diluted 1:100 in TE buffer, 100 µL of this solution was added to each well. The fluorescence intensity was measured using a fluorescence plate reader (Wallac Victor 1420 Multilabel Counter; Perkin Elmer, Waltham, MA) at an excitation wavelength of ~480 nm and an emission wavelength of ~520 nm. The fluorescence values of the reagent blank were subtracted from that of each of the samples and the percentage of free siRNA was determined by dividing the fluorescence intensity of the intact sample (without addition of Triton X-100) by the fluorescence value of the disrupted sample (caused by the addition of Triton X-100).

General Procedure: Animal Experiments

Mouse strain C57BL/6N was used for all in vivo experiments. Animals were obtained from Charles River (Sulzfeld, Germany) and were between 6 and 8 weeks old at the time of experiments. Intravenously administered LNP formulations were injected by infusion of 200 µL into the tail vein. Subcutaneously administered compounds were injected in a volume of 100-200 µL. Blood was collected by submandibular vein bleed the day before injection ("prebleed") and during the experiment post injection at times indicated. Serum was isolated with serum separation tubes (Greiner Bio-One, Frickenhausen, Germany) and kept frozen until analysis. 7 days after compound administration, mice were anaesthetized by $CO_2$ inhalation and killed by cervical dislocation. Blood was collected by cardiac puncture and serum isolated as described above. Tissue for mRNA quantification was harvested and immediately snap frozen in liquid nitrogen.

General Procedures: Measurement of Gene Knockdown

Determination of serum protein levels was achieved using the following: Factor VII was analyzed using the chromogenic enzyme activity assay BIOPHEN FVII (#221304, Hyphen BioMed, MariaEnzersdorf, Austria) following the manufacturer's recommendations. Mouse serum was diluted 1:3000 before analysis. Absorbance of colorimetric development at 405 nm was measured using a Victor 3 multilabel counter (Perkin Elmer, Wiesbaden, Germany).

ApoB protein in serum was measured by ELISA (Cloud-Clone Corp./Hoelzel Diagnostics, Cologne, Germany, #SEC003Mu). A 1:5000 dilution of mouse serum was processed according to the manufacturer's instructions and absorbance at 450 nm measured using a Victor 3 multilabel counter (Perkin Elmer, Wiesbaden, Germany).

Transthyretin (TTR, also known as prealbumin) protein in serum was measured by ELISA (#KA2070, Novus Biologicals/Biotechne, Wiesbaden, Germany). A 1:4000 dilution of mouse serum was processed according to the manufacturer's instructions and absorbance at 450 nm measured using a Victor 3 multilabel counter (Perkin Elmer, Wiesbaden, Germany).

For quantification of mRNA levels, frozen tissue pieces (30-50 mg) were transferred to a chilled 1.5 mL reaction tube. 1 mL Lysis Mixture (Epicenter Biotechnologies, Madison, USA) containing 3.3 µL/ml Proteinase K (50 µg/µL) (Epicenter Biotechnologies, Madison, USA) was added and tissues were lysed by sonication for several seconds using a sonicator (HD2070, Bandelin, Berlin, Germany) and digested with Proteinase K for 30 min at 65° C. in a thermomixer (Thermomixer comfort, Eppendorf, Hamburg, Germany). Lysates were stored at −80° C. until analysis. For mRNA analysis, lysates were thawed and mRNA levels were quantified using either QuantiGene 1.0 (FVII, ApoB and GAPDH) or Quantigene 2.0 (TTR) branched DNA (bDNA) Assay Kit (Panomics, Fremont, Calif., USA, Cat-No: QG0004) according to the manufacturer's recommendations. As assay readout, the chemiluminescence signal was measured in a Victor 2 Light luminescence counter (Perkin Elmer, Wiesbaden, Germany) as relative light units (RLU). The signal for the corresponding mRNA was divided by the signal for GAPDH mRNA from the same lysate. Values are reported as mRNA expression normalized to GAPDH.

Example 1: Generation of Thiol-Terminated siRNA

Where necessary 3'- or 5'-terminal thiol groups were introduced via 1-O-Dimethoxytrityl-hexyl-disulfide, 1'-[(2-cyanoethyl)-(N,N-diisopropyl)]-phosphoramidite linker (NucleoSyn, Olivet Cedex, France). Upon completion of the solid phase synthesis and final removal of the DMT group ("DMT off synthesis") oligonucleotides were cleaved from the solid support and deprotected using a 1:1 mixture consisting of aqueous methylamine (41%) and concentrated aqueous ammonia (32%) for 6 hours at 10° C. Subsequently, the crude oligonucleotides were purified by anion-exchange high-performance liquid chromatography (HPLC) on an AKTA Explorer System (GE Healthcare, Freiburg, Germany). Purified ($C_6SSC_6$)-oligonucleotides were precipitated by addition of ethanol and overnight storage in the freezer. Pellets were collected by centrifugation. Oligonucleotides were reconstituted in water and identity of the oligonucleotides was confirmed by electrospray ionization mass spectrometry (ESI-MS). Purity was assessed by analytical anion-exchange and RP HPLC.

Each disulfide containing oligomer was then reduced using a 100 mM DL-Dithiothreitol (DTT) solution. 1.0 M DTT stock solution (Sigma-Aldrich Chemie GmbH, Munich, Germany, #646563) was diluted with Triethylammonium bicarbonate buffer (TEABc, 1M, pH 8.5, Sigma, #90360) and water to give a solution 100 mM each in DTT and TEABc. The oligonucleotide was dissolved in TEABc buffer (100 mM, pH 8.5) to yield a 1 mM solution. To accomplish the disulfide reduction a 50-100 fold molar DTT excess is added to the oligonucleotide solution. The progress of the reduction was monitored by analytical AEX HPLC on a Dionex DNA Pac 200 column (4×250 mm) obtained from Thermo Fisher. The reduced material, i.e., the corresponding thiol (C6SH), elutes prior to the starting material. After completion of the reaction, excess reagent is removed by size exclusion chromatography using a HiPrep column from GE Healthcare and water as eluent. Subsequently, the oligonucleotide is precipitated using 3M NaOAc (pH 5.2) and ethanol and stored at minus 20° C.

Example 2: General Procedure for Preparation of Mono-DTME Oligomer

Thiol modified oligonucleotide was dissolved in 300 mM NaOAc (pH 5.2) containing 25% acetonitrile to give a 20 OD/mL solution. 40 equivalents dithiobismaleimidoethane (DTME, Thermo Fisher, #22335) were dissolved in acetonitrile to furnish a 15.6 mM solution. The DTME solution was added to the oligonucleotide-containing solution and agitated at 25° C. on a Thermomixer (Eppendorf, Hamburg, Germany). Progress of the reaction was monitored by analytical AEX HPLC using a Dionex DNA Pac200 column (4×250 mm). Depending on the required purity level excess DTME is either removed by size exclusion HPLC using a HiPrep column (GE Healthcare) or the crude reaction mixture is purified by preparative AEX HPLC using a column packed with Source 15 Q resin commercially available from GE Healthcare.

Example 3: General Procedure for Preparation of Dimer Via DTME Functionality

The DTME modified oligonucleotide prepared according to the procedure in Example 2 was reacted with another oligonucleotide equipped with a thiol linker. This reaction could either be carried out on the single stranded sequence or after prior annealing of the complementary oligonucleotide of one of the reaction partners. Consequently, if desired, the DTME modified oligonucleotide was reacted with the thiol modified oligonucleotide directly, or was annealed with its complementary strand and the resulting duplex reacted with the thiol modified oligonucleotide. Alternatively, the thiol modified oligonucleotide was annealed with its complementary strand and this duplex reacted with the DTME modified single strand. In all cases the reaction was carried out in aqueous solution in the presence of 300 mM NaOAc (pH 5.2).

Example 4: General Procedure for Annealing of Single Stranded RNAs (ssRNAs) to Form Double Stranded RNA (dsRNA)

dsRNAs were generated from RNA single strands by mixing equimolar amounts of complementary sense and antisense strands and annealing in 20 mM NaCl/4 mM sodium phosphate pH 6.8 buffer. Successful duplex formation was confirmed by native size exclusion HPLC using a Superdex 75 column (10×300 mm) from GE Healthcare. Samples were stored frozen until use.

Example 5: General Procedure for Preparation of 3'- or 5'-$NH_2$ Derivatized Oligonucleotides RNA equipped with a C-6-aminolinker at the 5'-end of the sense strand was produced by standard phosphoramidite chemistry on solid phase at a scale of 140 µmol using an ÄKTA Oligopilot 100 (GE Healthcare, Freiburg, Germany) and controlled pore glass (CPG) as solid support (Prime Synthesis, Aston, PA, USA). Oligomers containing 2'-O-methyl and 2'-F nucleotides were generated employing the corresponding 2'-OMe-phosphoramidites, 2'-F-methyl phosphoramidites. The 5'-aminohexyl linker at the 5'-end of the sense strand was introduced employing the TFA-protected hexylaminolinker phosphoramidite (Sigma-Aldrich, SAFC, Hamburg, Germany). In case the hexylamino-linker was needed at the 3'-position, a phtalimido protected hexylamino-linker immobilized on CPG (Prime Synthesis, Aston, PA, USA) was used. Cleavage and deprotection was accomplished using a mixture of 41% methylamine in water and concentrated aqueous ammonia (1:1 v/v). Crude oligonucleotides were purified using anion exchange HPLC and a column (2.5×18 cm) packed with Source 15Q resin obtained from GE Healthcare.

Example 6: General Method for GalNAc Ligand Conjugation

The trivalent GalNAc ligand was prepared as outlined in Hadwiger et al., patent application US 2012/0157509 A1.

The corresponding carboxylic acid derivative was activated using NHS chemistry according to the following procedure:

3GalNAc-COOH (90 µmol, 206 mg) was dissolved in 2.06 mL DMF. To this solution N-Hydroxysuccinimide (NHS, 14.3 mg (99 µmol, 1.1 eq.) and Diisopropylcarbodiimide (DIC, 18.29 µL, 1.05 eq., 94 µmol) were added at 0° C. This solution was stirred overnight at ambient temperature. Completion of the reaction was monitored by TLC (DCM:MeOH=9:1).

The precursor oligonucleotide equipped with an amino-hexyl linker was dissolved in sodium carbonate buffer (pH 9.6):DMSO 2:3 v/v to give a 4.4 mM solution. To this solution an aliquot of the NHS activated GalNAc solution (1.25 eq, 116 µL) was added. After shaking for 1 hour at 25° C., another aliquot (116 µL) of the NHS activated GalNAc was added. Once RP HPLC analysis showed at least more than 85% conjugated material, the crude conjugate was precipitated by addition of ethanol and storage in the freezer overnight. The pellet was collected by centrifugation. The pellet was dissolved in 1 mL concentrated aqueous ammonia and agitated for 4 hours at room temperature in order to remove the O-acetates from the GalNAc sugar residues. After confirmation of quantitative removal of the O-acetates by RP HPLC ESI MS, the material was diluted with 100 mM Triethyl ammonium acetate (TEAA) and the crude reaction mixture was purified by RP HPLC using an XBridge Prep C18 (5 µm, 10×50 mm, Waters) column at 60° C. on an ÄKTA explorer HPLC system. Solvent A was 100 mM aqueous TEAA and solvent B was 100 mM TEAA in 95% CAN, both heated to 60° C. by means of a buffer pre-heater. A gradient from 5% to 25% B in 60 min with a flow rate of 3.5 mL/min was employed. Elution of compounds was observed at 260 and 280 nm. Fractions with a volume of 1.0 mL were collected and analyzed by analytical RP HPLC/ESI-MS. Fractions containing the target conjugate with a purity of more than 85% were combined. The correct molecular weight was confirmed by ESI/MS.

Example 7: Oligonucleotide Precursors

Using the methodologies described in the above examples the following single-stranded monomers, dimers and GalNAc tagged monomers and dimers were prepared:

TABLE 1

Oligonucleotide Precursors-Single Strands (X)

| SEQ ID | ID | FVII sense strands (5'-3') |
|---|---|---|
| 1 | X18791 | ($C_6SSC_6$)gcAfaAfgGfcGfuGfcCfaAfcUfcAf(invdT)($C_6NH_2$) |
| 2 | X18792 | ($C_6SSC_6$)gcAfaAfgGfcGfuGfcCfaAfcUfcAf(invdT)($C_6NH$)(GalNAc$_3$) |
| 3 | X18793 | (SHC$_6$)gcAfaAfgGfcGfuGfcCfaAfcUfcAf(invdT)($C_6NH$)(GalNAc$_3$) |
| 4 | X18794 | ($C_6SSC_6$)gcAfaAfgGfcGfuGfcCfaAfcUfcAf(invdT) |
| 5 | X19569 | (SHC$_6$)gcAfaAfgGfcGfuGfcCfaAfcUfcAf(invdT) |
| 6 | X19574 | (DTME)(SHC$_6$)gcAfaAfgGfcGfuGfcCfaAfcUfcAf(invdT) |

| | ID | FVII antisense strands (5'-3') |
|---|---|---|
| 7 | X18796 | UfsGfaGfuUfgGfcAfcGfcCfuUfuGfcusu(C655C6)dT |
| 8 | X18797 | UfsGfaGfuUfgGfcAfcGfcCfuUfuGfcusu(C6SH) |
| 9 | X18798 | UfsGfaGfuUfgGfcAfcGfcCfuUfuGfcusu(C6SH)(DTME) |

| | ID | ApoB sense strands (5'-3') |
|---|---|---|
| 10 | X19577 | ($C_6SSC_6$)cuAfuUfuGfgAfgAfgAfaAfuCfgAf(invdT) |
| 11 | X19578 | (SHC$_6$)cuAfuUfuGfgAfgAfgAfaAfuCfgAf(invdT) |
| 12 | X19579 | (DTME)(SHC$_6$)cuAfuUfuGfgAfgAfgAfaAfuCfgAf(invdT) |

TABLE 2

Oligonucleotide Single Stranded Sense and Antisense Pairs; and Resulting Duplexes (XD) After Annealing.

| SEQ ID | Duplex ID | SEQ ID | Single Strand ID | Sequence (5'-3') | Target/ Strand |
|---|---|---|---|---|---|
| 15 | XD-00376 | 13 | X01162 | GGAUfCfAUfCfUfCfAAGUfCfUfUfACfdTsdT | FVIIs |
| | | 14 | X00549 | GUfAAGACfUfUfUfGAGAUfGAUfCfCfdTsdT | FVIIas |
| 18 | XD-00030 | 16 | X00116 | GcAAAGGcGuGccAAcucAdTsdT | FVIIs |
| | | 17 | X00117 | UGAGUUGGcACGCCUUUGCdTsdT | FVIIas |
| 21 | XD-01078 | 19 | X02943 | GGAAUCuuAuAuuuGAUCcAsA | ApoBs |
| | | 20 | X02944 | uuGGAUcAAAuAuAAGAuUCcscsU | Apoas |

TABLE 2-continued

Oligonucleotide Single Stranded Sense and Antisense Pairs; and Resulting Duplexes (XD) After Annealing.

| SEQ ID | Duplex ID | SEQ ID | Single Strand ID | Sequence (5'-3') | Target/Strand |
|---|---|---|---|---|---|
| 24 | XD-00194 | 22 | X00539 | cuuAcGcuGAGuAcuucGAdTsdT | LUCs |
|  |  | 23 | X00540 | UCGAAGuACUcAGCGuAAGdTsdT | LUCas |

TABLE 3

Derivatized Oligonucleotide Single Stranded Sense and Antisense Pairs; and Resulting Duplexes After Annealing.

| SEQ ID | Duplex ID | SEQ ID | Single Strand ID | Sequence (5'-3') | Target |
|---|---|---|---|---|---|
| 27 | XD-06328 | 25 | X18790 | (GalNAc3)(NHC$_6$)gcAfaAfgGfcGfuGfcCfaAfcUfcAf(invdT) | FVII |
|  |  | 26 | X18795 | UfsGfaGfuUfgGfcAfcGfcCfuUfuGfcusu |  |
| 30 | XD-06728 | 28 | X20124 | (GalNAc3)(NHC$_6$)cuAfuUfuGfgAfgAfgAfaAfuCfgAf(invdT) | ApoB |
|  |  | 29 | X19583 | UfsCfgAfuUfuCfuCfuCfcAfaAfuAfgusu |  |
| 33 | XD-06386 | 31 | X20216 | (GalNAc3)(NHC$_6$)sAfsasCfaGfuGfuUfCfUfuGfcUfcUfaUfaAf(invdT) | TTR |
|  |  | 32 | X19584 | usUfsaUfaGfaGfcAfagaAfcAfcUfgUfususu |  |
|  |  | 34 | X19571 | gcAfaAfgGfcGfuGfcCfaAfcUfcAf(invdT)(C$_6$NH)(GalNAc3) | FVII |
| 36 | XD-05961 | 35 | X18788 | gcAfaAfgGfcGfuGfcCfaAfcUfcAf(invdT) | FVII |
|  |  | 26 | X18795 | UfsGfaGfuUfgGfcAfcGfcCfuUfuGfcusu |  |

TABLE 4

Single Stranded Oligonucleotide Dimers Linked by DTME

| SEQ ID | ID | Sequence (5'-3') | Target/Strand |
|---|---|---|---|
| 37 | X15049 | GGAAUCuuAuAuuuGAUCcAsA(SHC$_6$)(DTME)GGAUfCfAUfCfUfCfAAGUfCfUfUfACfdTsdT(SHC$_6$) | ApoBs/F7as |
| 38 | X12714 | GGAUfCfAUfCfUfCfAAGUfCfUfUfACfdTsdT(SHC$_6$)(DTME)GUfAAGACfUfUfGAGAUfGAUfCfCfdTsdT(SHC$_6$) | F7s/F7as |
| 39 | X19575 | (SHC$_6$)gcAfaAfgGfcGfuGfcCfaAfcUfcAf(invdT)(C$_6$NH)(GalNAc$_3$)(DTME)(SHC$_6$)gcAfaAfgGfcGfuGfcCfaAfcUfcAf(invdT) | F7s/F7s |
| 40 | X19819 | UfsGfaGfuUfgGfcAfcGfcCfuUfuGfcusu(C$_6$SH)(DTME)UfsGfaGfuUfgGfcAfcGfcCfuUfuGfcusu(C$_6$SH) | F7as/F7as |
| 41 | X20336 | (SHC$_6$)gcAfaAfgGfcGfuGfcCfaAfcUfcAf(invdT)(C$_6$NH)(GalNAc$_3$)(DTME)(SHC$_6$)cuAfuUfuGfgAfgAfgAfaAfuCfgAf(invdT) | F7s/ApoBs |

TABLE 5

Single Strand DTME Dimers and Corresponding Monomers; and Resulting Duplexes After Annealing

| SEQ ID | Duplex ID | SEQ ID | Single Strand ID | Sequence (5'-3') | Target/Strand |
|---|---|---|---|---|---|
| 42 | XD-05311 | 37 | X15049 | GGAAUCuuAuAuuuGAUCcAsA(SHC6)(DTME)GGAUfCfAUfCfUfCfAAGUfCfUfUfACfdTsdT(SHC6) | ApoBs--FVIIs |
|  |  | 14 | X00549 | 5'-GUfAAGACfUfUfGAGAUfGAUfCfCfdTsdT-3' + | FVIIas |
|  |  | 20 | X02944 | 5'-uuGGAUcAAAuAuAAGAuUCcscsU-3' | ApoBas |

TABLE 5-continued

Single Strand DTME Dimers and Corresponding Monomers; and Resulting Duplexes After Annealing

| SEQ ID | Duplex ID | SEQ ID | Single Strand ID | Sequence (5'-3') | Target/Strand |
|---|---|---|---|---|---|
| 43 | XD-05312 | 38 | X12714 | GGAUfCfAUfCfUfCfAAGUfCfUfUfACfdTsdT (SHC6)(DTME) GUfAAGACfUfUfGAGAUfGAUfCfCfdTsdT (SHC6) | FVIIs--FVIIas |
|  |  | 13 | X01162 | 5'-GGAUfCfAUfCfUfCfAAGUfCfUfUfACfdTsdT-3' | FVIIs |
|  |  | 14 | X00549 | 5'-GUfAAGACfUfUfGAGAUfGAUfCfCfdTsdT-3' | FVIIas |

TABLE 6

Chemically Synthesized Disulfide-Linked Dimers and Trimers

| SEQ ID | Single Strand ID | Sequence (5'-3') | Target/Strand |
|---|---|---|---|
| 44 | X20366 | usUfsaUfaGfaGfcAfagaAfcAfcUfgUfususu(C6SSC6) UfsCfgAfuUfuCfuCfuCfcAfaAfuAfgusu | TTRas/ApoBas |
| 45 | X22413 | AfsasCfaGfuGfuUfCfUfuGfcUfcUfaUfaAf(invdT)(C6SSC6) gcAfaAfgGfcGfuGfcCfaAfcUfcAf(invdT) | FVIIs/TTRs |
| 46 | X20256 | (SHC6)gcAfaAfgGfcGfuGfcCfaAfcUfcAf(invdT)(C6NH) (GalNAc3)(SPDP)(NHC6)cuAfuUfuGfgAfgAfgAfaAfuCfgAf (invdT)(C6SSC6)AfsasCfaGfuGfuUfCfUfuGfcUfcUfaUfaAf (invdT) | FVII/ApoB/TTr |
| 47 | X20366 | usUfsaUfaGfaGfcAfagaAfcAfcUfgUfususu(C6SSC6) UfsCfgAfuUfuCfuCfuCfcAfaAfuAfgusu | TTRas/ApoBas |
| 48 | X22413 | AfsasCfaGfuGfuUfCfUfuGfcUfcUfaUfaAf(invdT)(C6SSC6) gcAfaAfgGfcGfuGfcCfaAfcUfcAf(invdT) | FVIIs/TTRs |

Key: In the Sequence portion of Tables 1-6 above (and those that follow): upper case letters "A", "C", "G" and "U" represent RNA nucleotides. Lower case letters "c", "g", "a", and "u" represent 2'-O-methyl-modified nucleotides; "s" represents phosphorothioate; and "dT" represents deoxythymidine residues. Upper case letters A, C, G, U followed by "f" indicate 2'-fluoro nucleotides. "(SHC6)" represents a thiohexyl linker. "(DTME)" represents the cleavable homobifunctional crosslinker dithiobismaleimidoethane. "(BMPEG2)" represents the non-cleavable homobifunctional crosslinker 1,8-bismaleimido-diethyleneglycol. "C6NH2" and "C6NH" are used interchangeably to represent the aminohexyl linker. "C6SSC6" represents The dihexyldisulfide linker. "GalNAc3" and "GalNAc" are used interchangeably to represent the tri-antennary N-acetylgalactosamine ligand, whose chemical structure is shown in FIG. 1. "SPDP" represents the reaction product of the reaction of succinimidyl 3-(2-pyridyldithio)propionate with the aminolinker equipped RNA. "InvdT" means inverted thymidine. In general, sequences are written left to right from the 5'- to the 3'-terminus; however, sequences comprising the DTME or BMPEG2 crosslinker are linked via the 3'-ends, and in these sequences the second half needs to be read from right to left (to maintain 5'- to 3' orientation); or if the second half is read from left to right, then the orientation is 3'- to 5'.

In the Target/Strand portion of the chart: "F7" or "FVII" designates an siRNA sequence targeting the Factor VII transcript (or mRNA) (also known as Factor VII). "ApoB" designates an siRNA sequence targeting the apolipoprotein B transcript. "TTR" designates an siRNA sequence targeting the transthyretin transcript. Sense strand is designated "s"; antisense strand is designated "as".

Example 8: General Procedure to Generate Dimeric, Trimeric and Tetrameric siRNAs by Sequential Annealing For the preparation of dimeric, trimeric and tetrameric siRNAs, a stepwise annealing procedure was performed. The annealing was performed in water and utilized stepwise addition of complementary strands. No heating/cooling of the solution was required. After each addition, an aliquot of the annealing solution was removed and monitored for duplex formation using analytical RP HPLC under native conditions (20° C.). The required amounts to combine equimolar amounts of complementary single strands were calculated based on the extinction coefficients for the individual single strands computed by the nearest neighbor method. If the analytical RP HPLC trace showed excess single strand, additional amounts of the corresponding complementary strand were added to force duplex formation ("duplex titration").

Duplex titration was monitored using a Dionex Ultimate 3000 HPLC system equipped with a XBridge C18 Oligo BEH (2.5 m; 2.1×50 mm, Waters) column equilibrated to 20° C. The diagnostic wavelength was 260 nm. Buffer A was 100 mM Hexafluoro-isopropanol (HFIP), 16.3 mM triethylamine (TEA) containing 1% methanol, Buffer B had the same composition except MeOH was 95%. A gradient from 5% to 70% buffer B in 30 minutes was applied at a flow rate of 250 µL/min. The two complementary strands were run independently to establish retention times. Then the aliquot containing the duplex solution was analyzed and compared to the retention times of the constituent single strands. In case the duplex solution showed a significant amount of single strand the corresponding complementary strand was added to the duplex solution.

Example 9: Preparation of FVII-DTME-ApoB Heterodimer (XD-05311)

Figure 2:
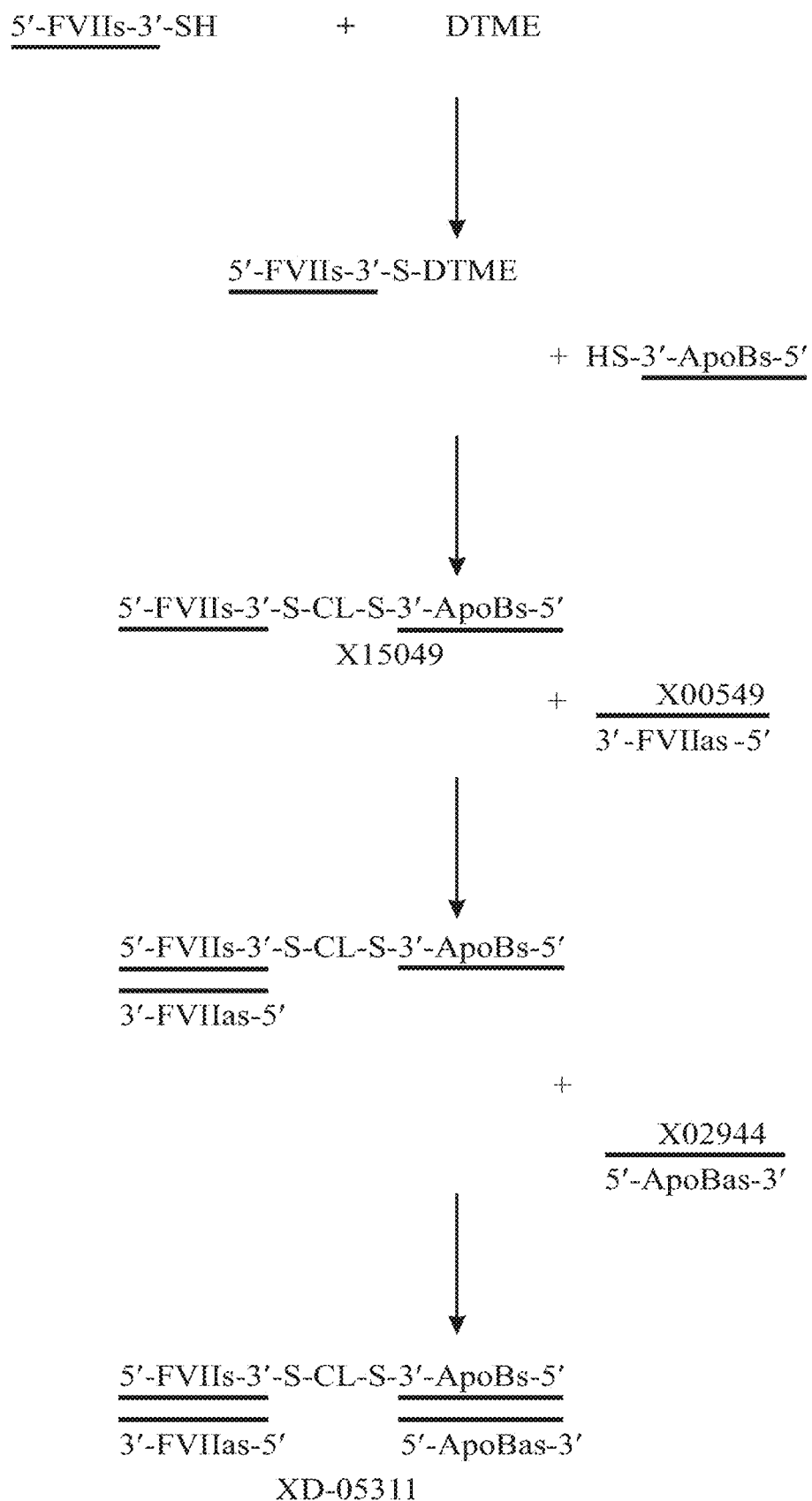
FIG. 2 presents a schematic of a synthesis of an FVII-ApoB heterodimer (XD-05311), which is discussed in connection with Example 9.

The FVII-ApoB heterodimer (XD-05311) was prepared in high purity by sequential combination of the following single strands using the methodology described in Example 8 and depicted in FIG. 2.

The single stranded heterodimer X15049 was purified on an ÄKTA explorer 100 (GE Healthcare) equipped with a ResourceQ column obtained from GE Healthcare. Buffer A was 10 mM sodium perchlorate, 20 mM Tris, 1 mM EDTA, pH 7.4 (Fluka, Buchs, Switzerland) in 20% aqueous Acetonitrile and buffer B was the same as buffer A but contained 500 mM sodium perchlorate. The column was maintained at 60° C. using a column oven. The flow rate was 4 mL/min. The crude material was loaded on to the column using the instrument's sample pump. Elutuin was recorded at 280 nm and a gradient from 15% B to 45% B in 45 minutes was employed. Appropriate fractions were pooled and precipitated by the addition of 3M sodium acetate (NaOAc, pH5.2)/ethanol 1/32 (v/v) and storage at minus 20° C. over night. The pellet was collected by centrifugation and the material reconstituted in water. The material was analyzed for purity using analytical AEX HPLC. Using a Dionex DNA Pac 200 column (4×250 mm) the material had a purity of 92.8% area. In addition, the material was analyzed by RP HPLC on a XBridge C18 Oligo BEH column from waters (2.5 m; 2.1×50 mm). Using this technique the material had 96.5% area.

Example 10: In Vivo Analysis of LNP-Formulated FVII-ApoB Heterodimer (XD-05311) (Animal Experiment MausRNAi-TV30)

Figure 3:
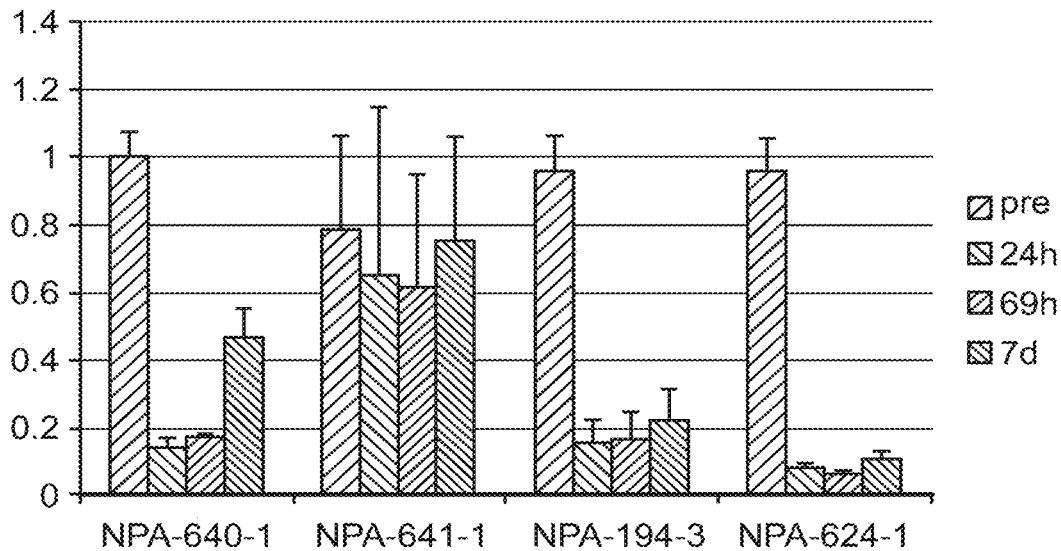
FIG. 3 presents data showing FVII activity from mouse serum in vivo, which is discussed in connection with Example 10.
Figure 4:
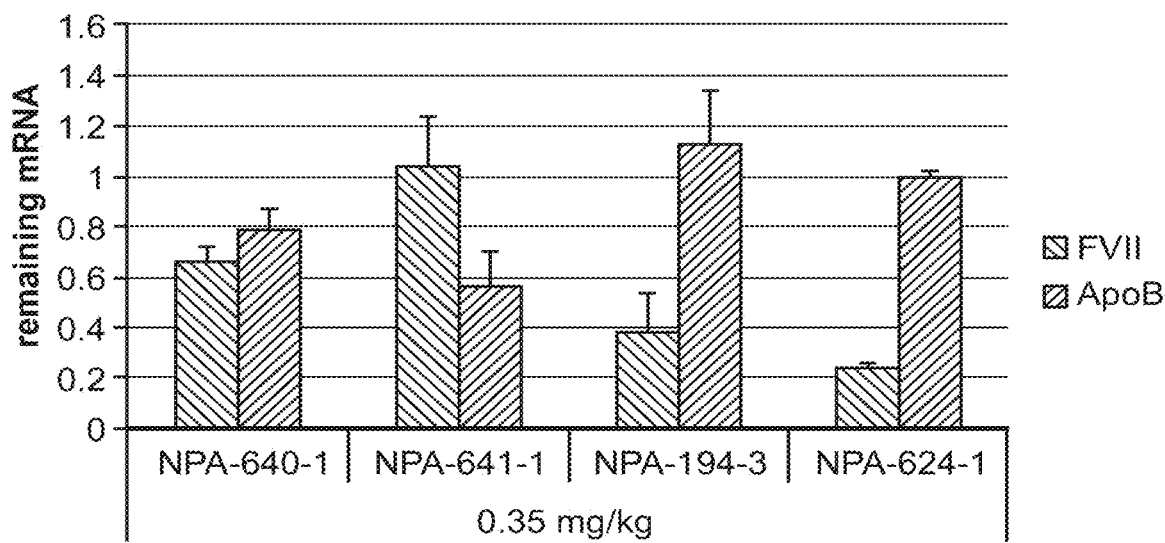
FIG. 4 presents data showing FVII and ApoB mRNA level from liver tissue in animal experiment MausRNAi-TV30, which is discussed in connection with Example 10.

A heterodimeric siRNA targeting Factor VII and ApoB (XD-05311) was formulated into LNP according to the General Procedure: Lipid Nanoparticle Formulation (above) and using the standard KL52 (XL10) formulation consisting of KL52/DSPC/Cholesterol/PEG-c-DMOG 50:10:38.5/1.5 mole %. A canonical siRNA for ApoB (XD-01078) and a canonical siRNA for FVII (XD-00030) were each formulated in the same LNP (XL10), and an additional canonical siRNA for FVII (XD-00030) was formulated in the standard KL22 (XL7) formulation consisting of KL22/DSPC/Cholesterol/PEG-c-DMOG 50:10:38.5/1.5 mole %. The LNP formulations, summarized in Table 7 below, were characterized according to General Procedure: LNP Characterization (above) and tested for in vivo efficacy in an animal experiment as described in General Procedure: Animal Experiments (above). Group size was n=3 mice for treatment groups and n=6 for saline control. All compounds were injected intravenously at a dose of 0.35 mg/kg. Blood was collected prior to injection, and at 24 hours, 69 hours, and 7 days post-injection at the time points described above and analyzed for FVII enzyme activity according to General Procedures: Measurement of Gene Knockdown (above). Results are shown in FIG. 3. mRNA levels of FVII and ApoB in liver lysates were measured at day 7 post injection, and are shown in FIG. 4.

TABLE 7

LNP-formulations used in animal experiment MausRNAi-TV30

| Formulation ID | siRNA | Lipid |
| --- | --- | --- |
| NPA-640-1 | Heterodimer FVII-ApoB (XD-05311) | XL10 Std |
| NPA-641-1 | ApoB (XD-01078) | XL10 Std |
| NPA-194-3 | FVII (XD-00030) | XL10 Std |
| NPA-624-1 | FVII (XD-00030) | XL7 Std |

Example 11: Preparation of 5'-GalNAc-FVII Canonical Control (XD-06328)

Figure 5:
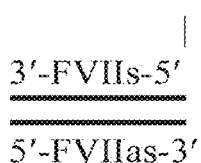
FIG. 5 presents a 5'-GalNAc-FVII canonical control, which is discussed in connection with Example 11.

5'-GalNAc-FVII Canonical Control (XD-06328) (see FIG. 5) was prepared by annealing ssRNA strands X18790 and X18795 by the methods described in Example 4. The product was obtained in 91.6% purity as determined by HPLC analysis.

Example 12: Preparation of 3'-GalNAc-FVII-DTME-FVII Homodimer with Cleavable Linker Joining 3' Antisense Strands and GalNAc Conjugated to External 3' End of Sense Strand (XD-06330)

Figure 6:
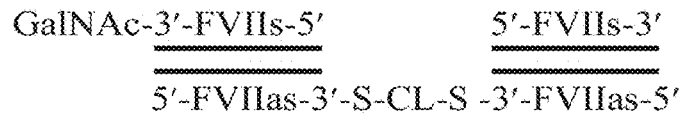
FIG. 6 presents a GalNAc-homodimer conjugate (XD-06330), which is discussed in connection with Example 12.

GalNAc-conjugated homodimeric siRNA XD-06330 targeting FVII (FIG. 6) was prepared (10 mg, 323 nmol) by combining the single stranded dimer X19819 stepwise with X18788 and X19571 according to the duplex titration method described in Example 8. The isolated material was essentially pure by HPLC analysis.

TABLE 8

Stoichiometries of Oligomers Used in Synthesis of GalNAc-FVII-DTME-FVII Homodimer (XD-06330)

| SEQ ID | ID | Target | E (L/mol * cm) | Nmol/OD | MW (free Acid) | MW Na salt | Req OD |
| --- | --- | --- | --- | --- | --- | --- | --- |
| 40 | X19819 | FVIIas-FVIIas | 389000 | 2.57 | 14405.6 | 15372.9 | 174 |
| 36 | X18788 | FVIIs | 193000 | 5.18 | 6545.3 | 6962.9 | 62.3 |
| 34 | X19571 | FVIIs | 193000 | 5.18 | 8161.0 | 8600.6 | 62.3 |
| 49 | XD-06330 | | | | 29111.9 | 30936.4 | |

Example 13: Preparation of 3'-GalNAc-FVII-DTME-FVII Homodimer with Cleavable Linker Joining 5' Sense Strands and GalNAc Conjugated to External 3' End of Sense Strand (XD-06360)

Figure 7:
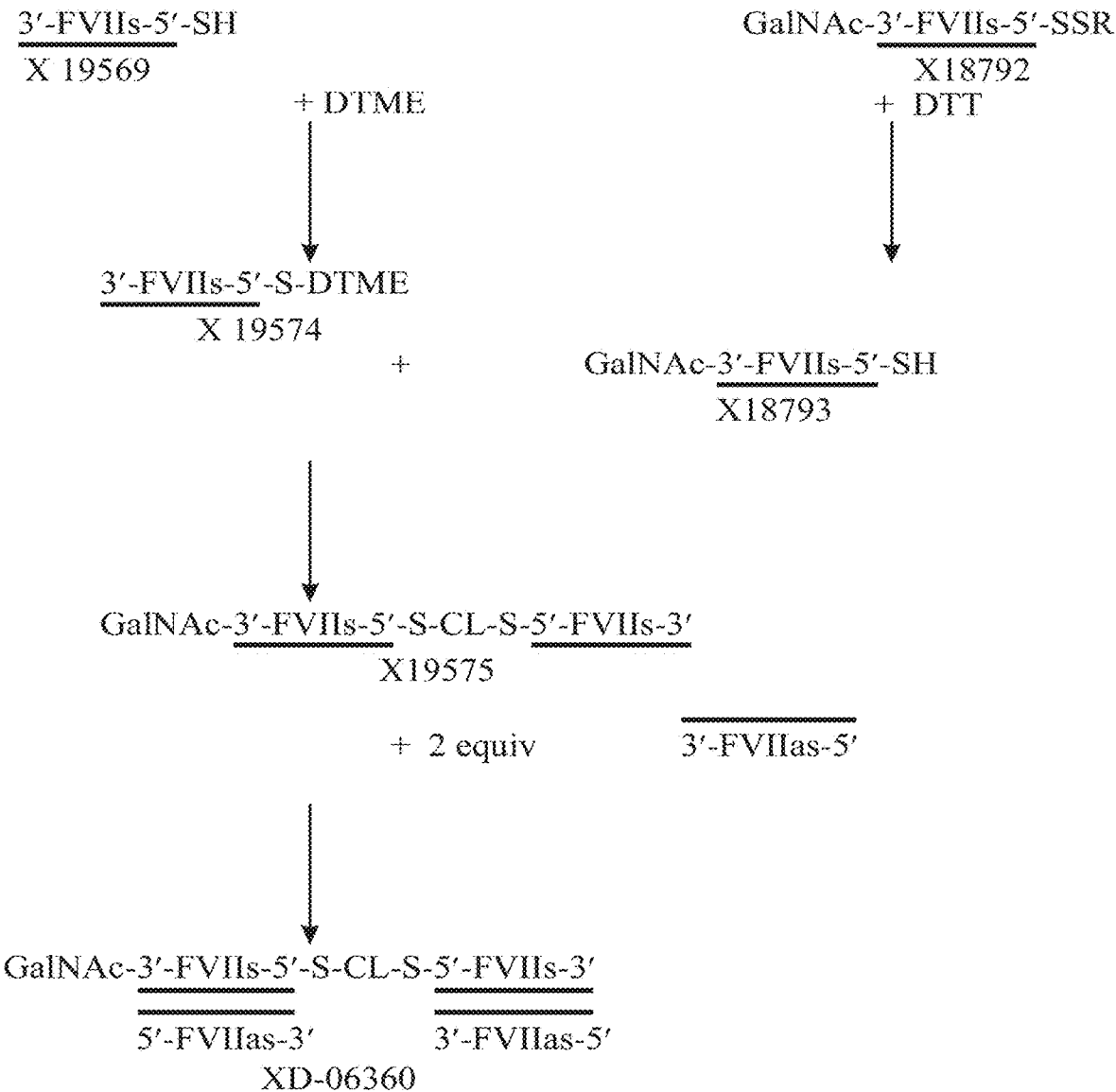
FIG. 7 presents a schematic of a synthesis of a GalNAc-homodimer conjugate (XD-06360), which is discussed in connection with Example 13.

GalNAc-conjugated homodimeric siRNA XD-06360 targeting FVII was prepared (11 mg, 323 nmol) by combining single strands stepwise using the synthesis strategy depicted in FIG. 7 and the methodology described in Example 8.

All reactive steps produced high quality material, with oligomer X19575 being determined to be 91.7 and 93.4% pure by ion exchange and reverse phase chromatography respectively, and oligomer XD-06360 being isolated in 86.8% purity as determined by nondenaturing reverse phase HPLC. The stoichiometries of the various oligomers used in the synthesis are shown in Table 9.

TABLE 9

Stoichiometries of Oligomers Used in Synthesis of GalNAc-FVII-FVII Homodimer (XD-06360)

| SEQ ID | ID | Target | E (L/mol *cm) | Nmol/OD | MW (free Acid) | MW Na salt | Req OD |
|---|---|---|---|---|---|---|---|
| 39 | X19575 | FVIIs-FVIIs | 384800 | 2.60 | 15413.1 | 16314.4 | 137 |
| 26 | X18795 | FVIIas | 194800 | 5.13 | 6849.4 × 2 | 7289.1 × 2 | 139 |
| 50 | XD06360 | | | | 29111.9 | 30892.6 | |

Example 14: Preparation of 5'-GalNAc-FVII-DTME-FVII Homodimer with Cleavable Linker Joining 3' Antisense Strands and GalNAc Conjugated to Internal 5' End of Sense Strand (XD-06329)

Figure 8:
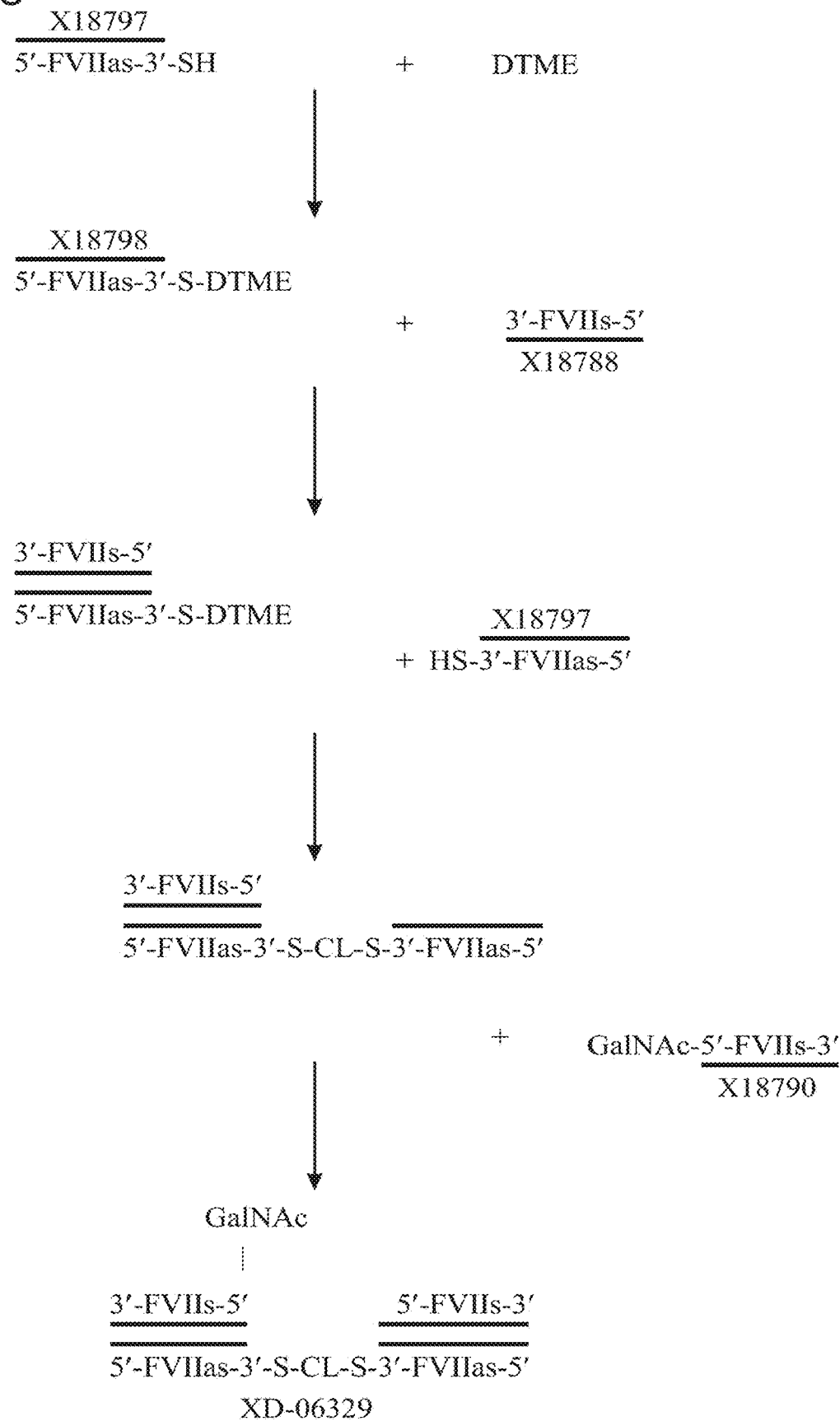
FIG. 8 presents a schematic of a synthesis of a GalNAc-homodimer conjugate (XD-06329), which is discussed in connection with Example 14.

GalNAc-conjugated homodimeric siRNA XD-06329 targeting FVII [SEQ ID 51] was prepared as depicted in FIG. 8 by annealing 1150 nmol of X18788 and 1150 nmol X18798. The sum of the ODs of the individual strands was 450 ODs and the combined solution, i.e., the duplex, had 394 ODs due to the hyperchromicity (394 ODs=1150 nmol duplex). This DTME modified duplex was reacted with 1150 nmol X18797 (3'-SH modified FVII antisense) (224 ODs). After HPLC purification, 364 ODs "half-dimer" siRNA was isolated. "Half-dimer" FVII siRNA (10 mg, 323 nmol, 174 ODs) was then annealed with 5'GalNAc-FVII sense (X18790) (323 nmol, 62.3 OD) to yield final product XD-06329.

Example 15: Determination of In Vivo FVII Gene Knockdown by FVII Homodimeric GalNAc Conjugates (XD-06329, XD-06330 and XD-06360)

Figure 9:
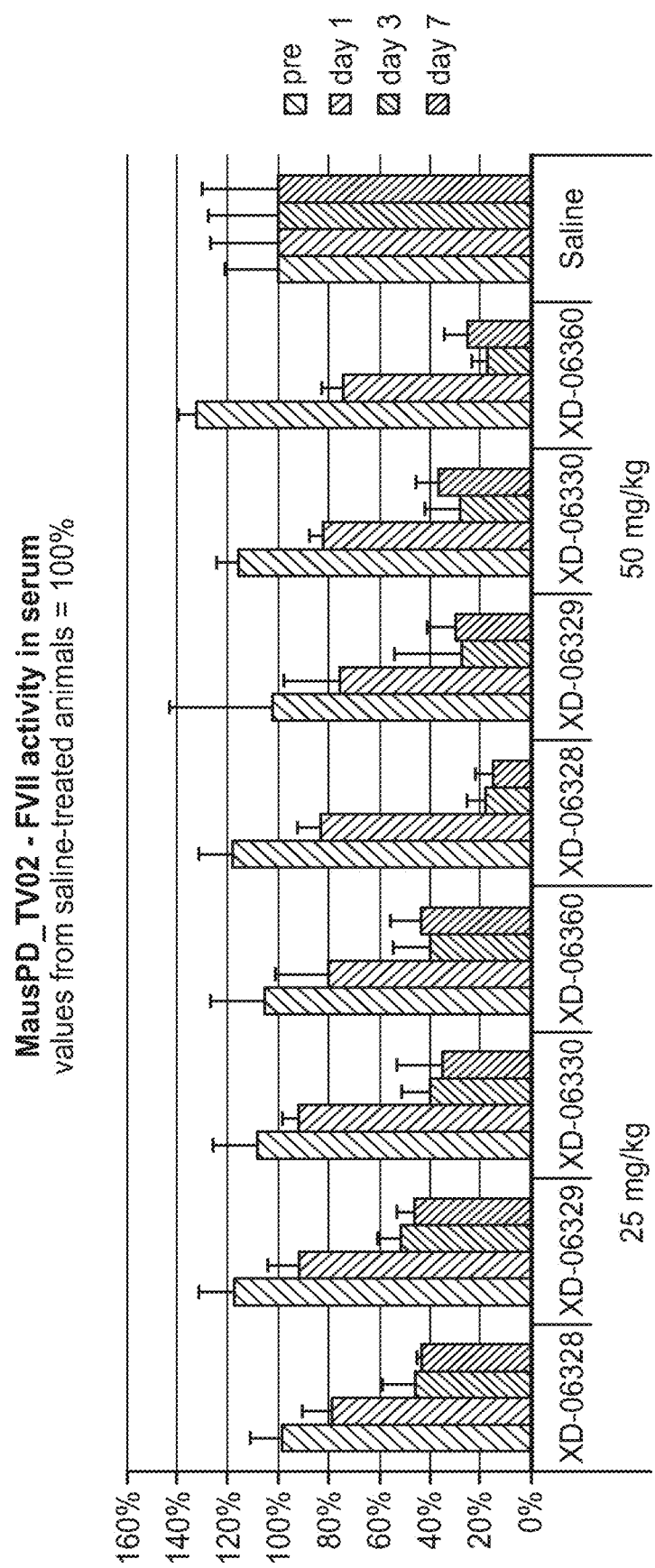
FIG. 9 presents data showing FVII activity in mouse serum (knockdown by FVII homodimeric GalNAc conjugates), which is discussed in connection with Example 15.

Three different variants of homodimeric, GalNAc-conjugated siRNAs targeted against Factor VII (XD-06329, XD-06330 and XD-06360) and a monomeric GalNAc-conjugated FVII-siRNA (XD-06328) were tested for in vivo efficacy in an animal experiment as described above (General Procedure: Animal Experiments). Group size was n=4 mice for treatment groups and n=5 for saline control. All compounds were injected subcutaneously at different doses (25 mg/kg or 50 mg/kg) in a volume of 0.2 mL. Blood was collected 1 day prior to treatment, and at 1, 3 and 7 days post-treatment, and analyzed for FVII enzyme activity. Results are shown in FIG. 9.

Silencing activity, onset of action, and potency of the homodimeric GalNAc-conjugates (XD-06329, XD-06330 and XD-06360) was comparable to the monomeric, canonical control (XD-06328) on a knockdown per unit weight basis. No signs of toxicity were observed (e.g., weight loss, abnormal behavior). However, upon normalizing for GalNAc content, the homodimeric GalNAc conjugates were all more effective at FVII knockdown than GalNAc monomer, thereby demonstrating more efficient siRNA uptake per ligand/receptor binding event. These results are shown in FIGS. 10A and 10B and 10C.

FIG. 10A. Factor VII serum activity after subcutaneous administration of GalNAc conjugates or PBS. Factor VII serum values at each time point are normalized to control mice, which were injected with 1×PBS. In this case, the amount of GalNAc injected in the animals was kept nearly constant. Factor VII serum activity was measured three days before injection (−3), or 1, 3, or 7 days following injection. Data are plotted as average+/−S.E.M., and N=3 mice/group. The bars at each datapoint (days −3, 1, 3, and 7) correspond, left to right, to X06328, X06329, X06330, and X06360, respectively.

FIG. 10B. Factor VII serum activity after subcutaneous administration of GalNAc conjugates or PBS. Factor VII serum values at each time point are normalized to control Factor VII values taken 3 days before injection. In this case, the amount of GalNAc injected in the animals was kept nearly constant. Factor VII serum activity was measured three days before injection (−3), or 1, 3, or 7 days following injection. Data are plotted as average+/−S.E.M. and N=3 mice/group. The bars at each data point (days −3, 1, 3, and 7) correspond, left to right, to X06328, X06329, X06330, and X06360, respectively.

Example 16: Preparation of Canonical GalNAc-siRNAs Independently Targeting FVII (XD-06328), ApoB (XD-06728) and TTR (XD-06386)

Three canonical siRNAs independently targeting FVII (XD-06328), ApoB (XD-06728) and TTR (XD-06386) (see FIG. 11) were independently prepared by solid phase synthesis. Three sense strands (X18790, X20124, X20216, respectively) were separately prepared with a 5'-hexylamine linker. Following cleavage and deprotection of the oligonucleotides and HPLC purification of the crude material conjugation of a per-acetylated GalNAc cluster to each oligo was achieved using NHS chemistry. Removal of the O-acetates by saponification was mediated by aqueous ammonia. The complementary antisense strands (X18795, X19583, and X19584, respectively) were synthesized by standard procedures provided above, followed by annealing to the GalNAc conjugated single strands to yield siRNAs targeting FVII (XD-06328), ApoB (XD-06728) and TTR (XD-06386) in 99.7, 93.1 and 93.8% purity respectively.

TABLE 10

GalNAc-siRNA Conjugates

| SEQ ID | Duplex ID | ssRNA | Sequence 5'-3' | |
|---|---|---|---|---|
| 27 | XD-06328 | X18790 | (GalNAc3)(NHC₆)gcAfaAfgGfcGfuGfcCfaAfcUfcAf(invdt) | FVII |
|  |  | X18795 | UfsGfaGfuUfgGfcAfcGfcCfuUfuGfcusu |  |
| 30 | XD-06728 | X20124 | (GalNAc3)(NHC₆)cuAfuUfuGfgAfgAfgAfaAfuCfgAf(invdT) | ApoB |
|  |  | X19583 | UfsCfgAfuUfuCfuCfuCfcAfaAfuAfgusu |  |
| 33 | XD-06386 | X20216 | (GalNAc3)(NHC₆)sAfsasCfaGfuGfuUfCfUfuGfcUfcUfaUfaAf(invdT) | TTR |
|  |  | X19584 | usUfsaUfaGfaGfcAfagaAfcAfcUfgUfususu |  |

Example 17: Preparation of GalNAc-FVII-ApoB-TTR Trimer with Cleavable Linkages on Sense Strands (XD06726)

Figure 13:
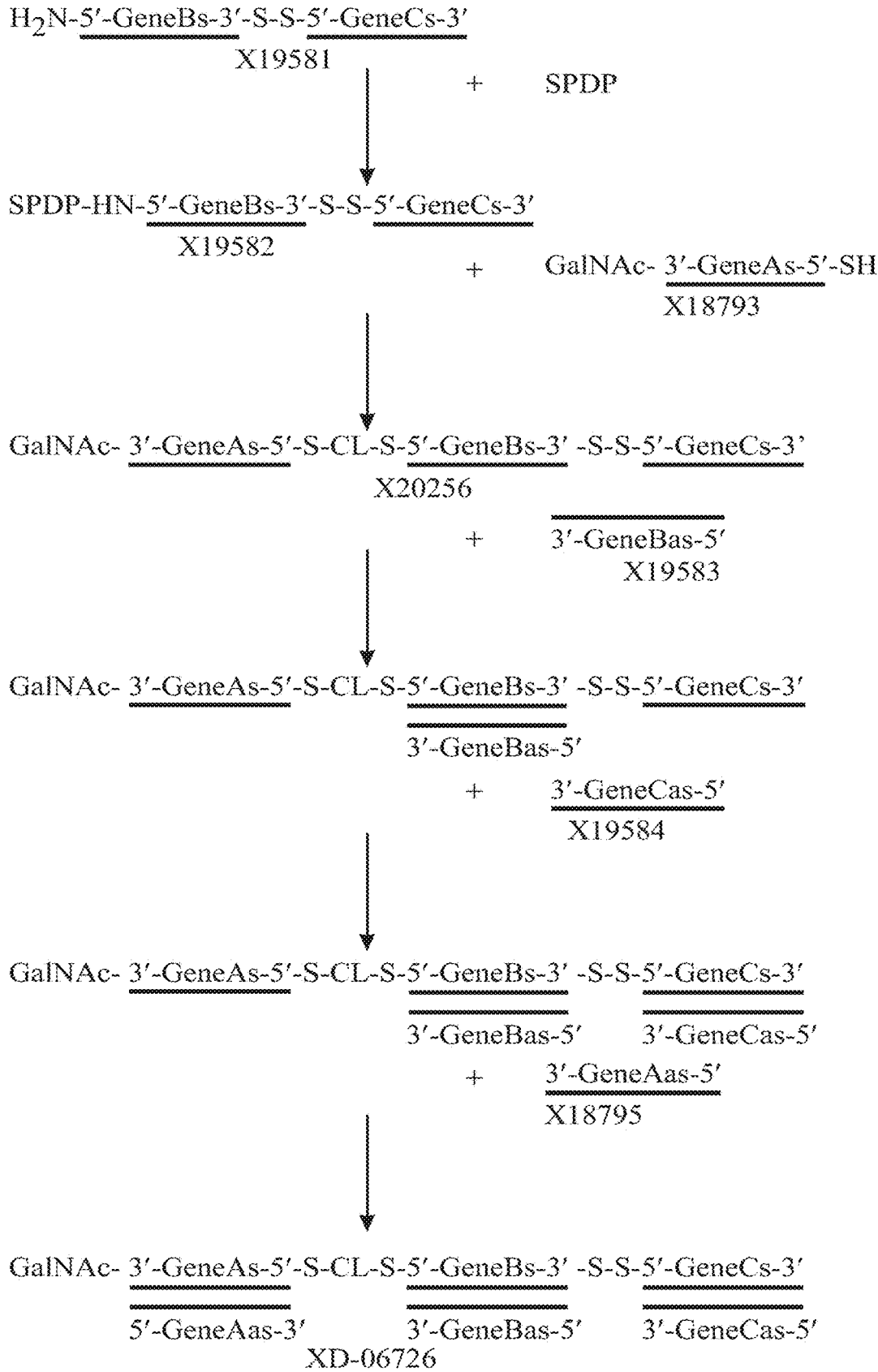
FIG. 13 presents a schematic of a synthesis strategy for a GalNAc-conjugated heterotrimer (XD06726), which is discussed in connection with Example 17. Key: In this example, "GeneA" is siFVII; "GeneB" is siApoB; and "GeneC" is siTTR.

A heterotrimer targeting FVII, ApoB and TTR conjugated to GalNAc (see FIG. 12) was synthesized using a hybrid strategy of solid phase and solution phase, as depicted in FIG. 13.

FIG. 13: Synthesis Strategy for GalNAc-Conjugated Heterotrimer (XD06726)

The dimer X19581 was made using solid phase chemistry with an aminohexyl linker on the 5'-end using the corresponding commercially available TFA protected phosphoramidite (SAFC Proligo, Hamburg, Germany). The sequence was cleaved from the solid support, deprotected and purified according to the conditions outlined above. In order to install an additional disulfide linker, the oligonucleotide's 5'-aminohexyllinker was reacted with SPDP (succinimidyl 3-(2-pyridyldithio)propionate)

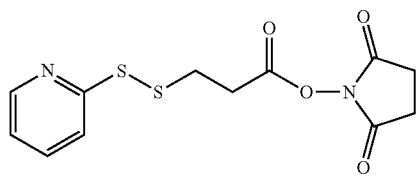 [SMILES: O=C(CCSSc1ccccn1)ON1C(=O)CCC1=O]

available from Sigma (#P3415). 928 nmol (400 OD) oligonucleotide was dissolved in 4.7 mL 100 mM TEAB, pH8.5, containing 20% Dimethyl formamide (DMF). To this solution was added a solution of 1.4 mg (4.6 μmol, 5 eq) SPDP in 100 μL DMF. Once analytical RP HPLC indicated consumption of the starting material, the crude reaction mixture was purified on a C18 XBridge column (10×50 mm) purchased from Waters. RP purification was performed on an ÄKTA explorer HPLC system. Solvent A was 100 mM aqueous TEAA and solvent B was 100 mM TEAA in 95% ACN. Solvents were heated to 60° C. by means of a buffer pre-heater and the column was kept in an oven at the same temperature. A gradient from 0% to 35% B in 45 min with a flow rate of 4 mL/min was employed. Elution of compounds was observed at 260 and 280 nm. Fractions with a volume of 1.5 mL were collected and analyzed by analytical RP HPLC/ESI-MS. Suitable fractions were combined and the oligonucleotide X19582 precipitated at minus 20° C. after addition of ethanol and 3M NaOAc (pH5.2). Identity was confirmed by RP-HPLC ESI-MS.

In order to prepare the single stranded trimer, the above oligonucleotide X19582 (255 nmol) was dissolved in 1.3 mL water. To this solution 306 nmol (1.2 eq) of the thiol modified oligonucleotide X18793 was added. The reaction mixture contained 200 mM TEAA and 20% acetonitrile. Progress of the reaction was followed by RP HPLC. Once the starting material was consumed the reaction mixture was purified using the same conditions as described in the previous paragraph, with the exception that the gradient was run from 0% B to 30% B in 45 min.

The single-stranded heterotrimer X20256 (containing linked sense strands of siFVII, siApoB and siTTR) was obtained in high purity. The sequence of X20256 is shown in Table 11.

TABLE 11

| SEQ ID | ID | Sequence | Target/Strand |
|---|---|---|---|
| 52 | X20256 | (SHC₆)gcAfaAfgGfcGfuGfcCfaAfcUfcAf(invdT)(C₆NH)(GalNAc3)(SPDP)(NHC₆)cuAfuUfuGfgAfgAfgAfaAfuCfgAf(invdT)(C₆SSC₆)AfsasCfaGfuGfuUfCfUfuGfcUfcUfaUfaAf(invdT) | FVIIs/ApoBs/TTRs |

Note: In principle the above sequence is accessible through a single solid phase synthesis. In this case, SPDP and C6NH2 would be replaced by the C₆SSC₆ phosphoramidite. However, due to the sequence length of the entire construct such a synthesis would be challenging.

Thereafter, the heterotrimeric duplex construct (XD-06726), simultaneously targeting FVII, ApoB and TTR, 7 mg (150 nmol), was prepared by sequentially adding the antisense single strands stepwise to the sense-strand heterotrimeric intermediate (X20256) according to the duplex titration method described Example 8.7 mg of material was obtained which was essentially pure by HPLC.

TABLE 12

Stoichiometries of Oligomers Used in Synthesis of GalNAc-FVII-ApoB-TTR Trimer (XD-06726).

| SEQ ID | ID | Target | E (L/mol * cm) | Nmol/OD | MW (free Acid) | MW Na salt | Req OD |
|---|---|---|---|---|---|---|---|
| 52 | X20256 | FVIIs-Apobs-TTRs | 623900 | 1.60 | 22690.8 | 24075.7 | 94 |
| 29 | X19583 | ApoBas | 206500 | 4.84 | 6762.4 | 7202.1 | 31 |
| 32 | X19584 | TTRas | 240400 | 4.16 | 7596.1 | 8079.7 | 36 |
| 26 | X18795 | FVIIas | 194800 | 5.13 | 6849.4 | 7289.1 | 29 |
| 53 | XD-06726 | | | | 43898.7 | 46646.6 | |

Example 18: Preparation of GalNAc-FVII-ApoB-TTR Trimer with Cleavable Linkages on Alternating Sense and Antisense Strands (XD06727)

Figure 14:
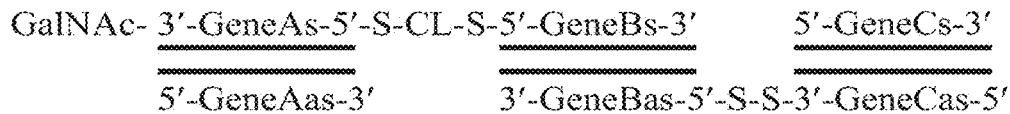
FIG. 14 presents a GalNAc-heterotrimer conjugate (XD06727), which is discussed in connection with Example 18. Key: In this example, "GeneA" is siFVII; "GeneB" is siApoB; and "GeneC" is siTTR.
Figure 15:
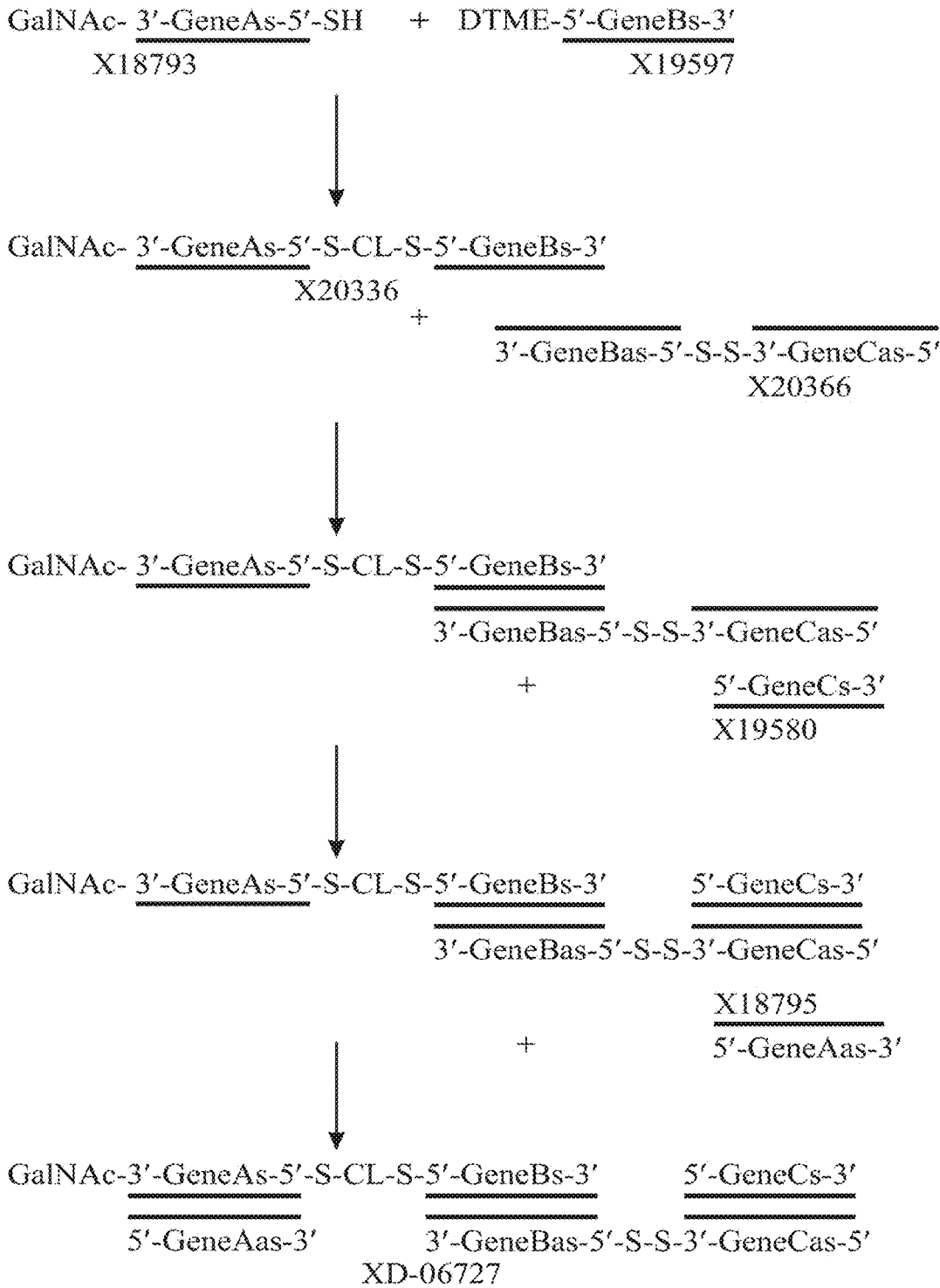
FIG. 15 presents a schematic of a synthesis strategy for GalNAc-Conjugated Heterotrimer (XD06727), which is discussed in connection with Example 18. Key: In this example, "GeneA" is siFVII; "GeneB" is siApoB; and "GeneC" is siTTR.

9 mg (192 nmol) of Trimeric siRNA XD-06727 (see FIG. 14), simultaneously targeting FVII, ApoB and TTR, was prepared in high purity by combining single strands stepwise as depicted in FIG. 15, using the methodology described in Example 8.

TABLE 13

Stoichiometries of Oligomers use in synthesis of GalNAc-siFVII-siApoB-siTTR Trimer (XD-06727)

| SEQ ID | ID | Target | E (L/mol * cm) | 1 OD | MW (free Acid) | MW Na salt | Req OD |
|---|---|---|---|---|---|---|---|
| 42 | X20336 | FVIIs-ApoBs | 404300 | 2.47 nmol | 15440.1 | 16341.4 | 78 |
| 49 | X20366 | ApoBas-TTRas | 446700 | 2.24 nmol | 14748.9 | 15716.1 | 86 |
| | X19580 | TTRs | 220300 | 4.54 nmol | 7105.6 | 7567.2 | 42 |
| 26 | X18795 | FVIIas | 194800 | 5.13 nmol | 6849.4 | 7289.1 | 37 |
| 54 | XD-06727 | | | | 44144 | 46913.8 | |

Figure 16:
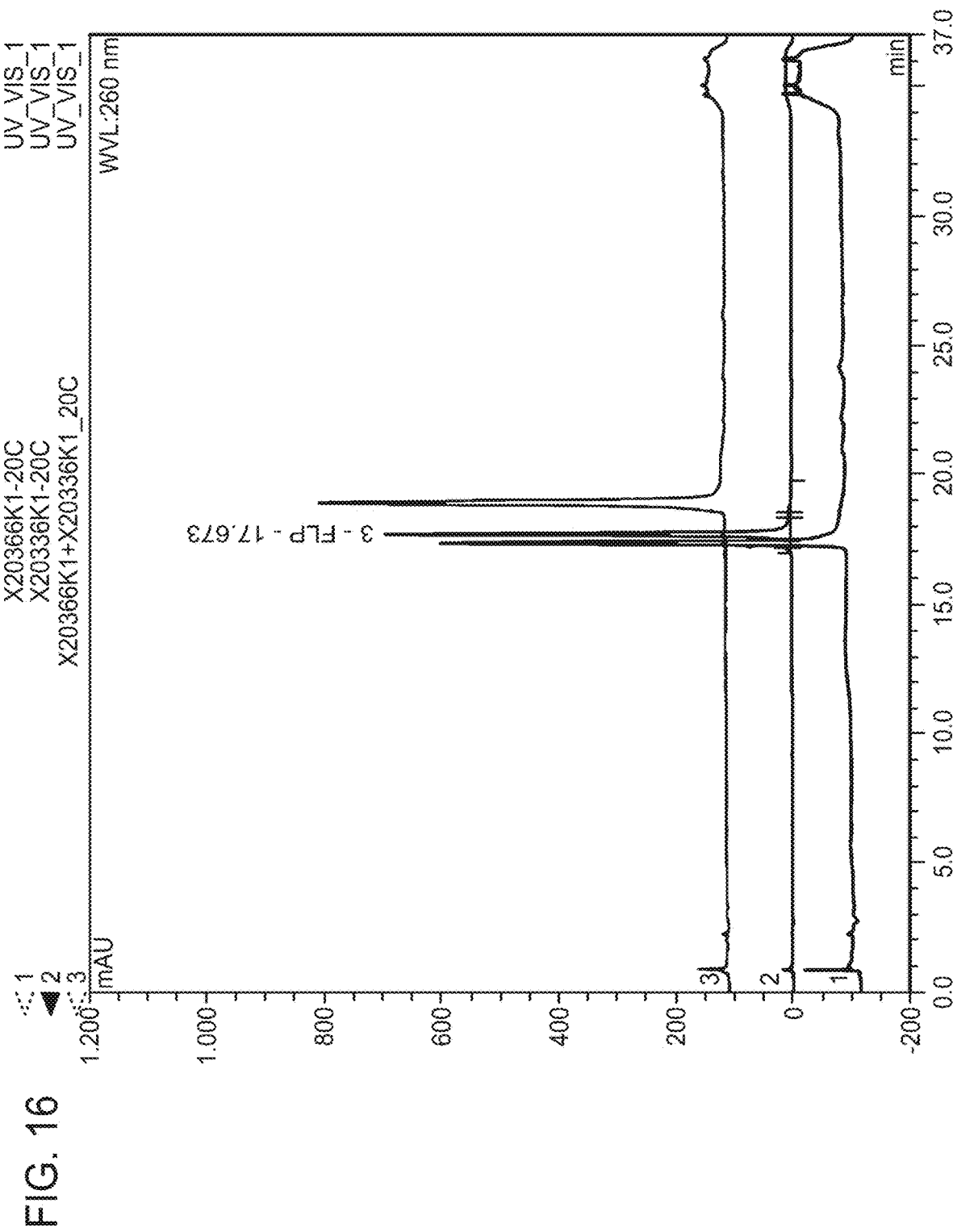
FIG. 16 presents data for an HPLC analysis of reaction of action of X20336 to X20366, which is discussed in connection with Example 18.
Figure 17:
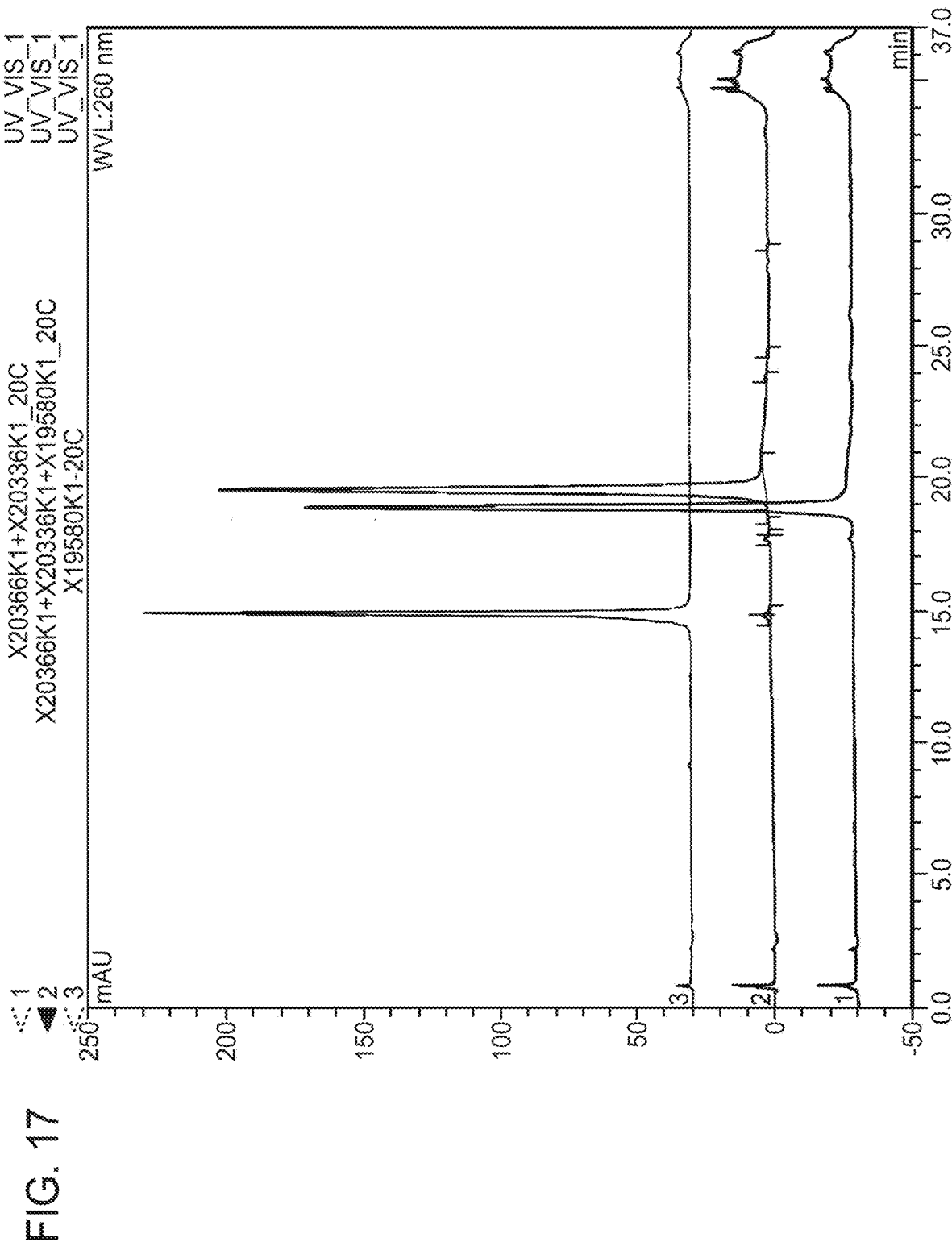
FIG. 17 presents data for an HPLC analysis of addition of X19580 to the reaction, which is discussed in connection with Example 18.
Figure 18:
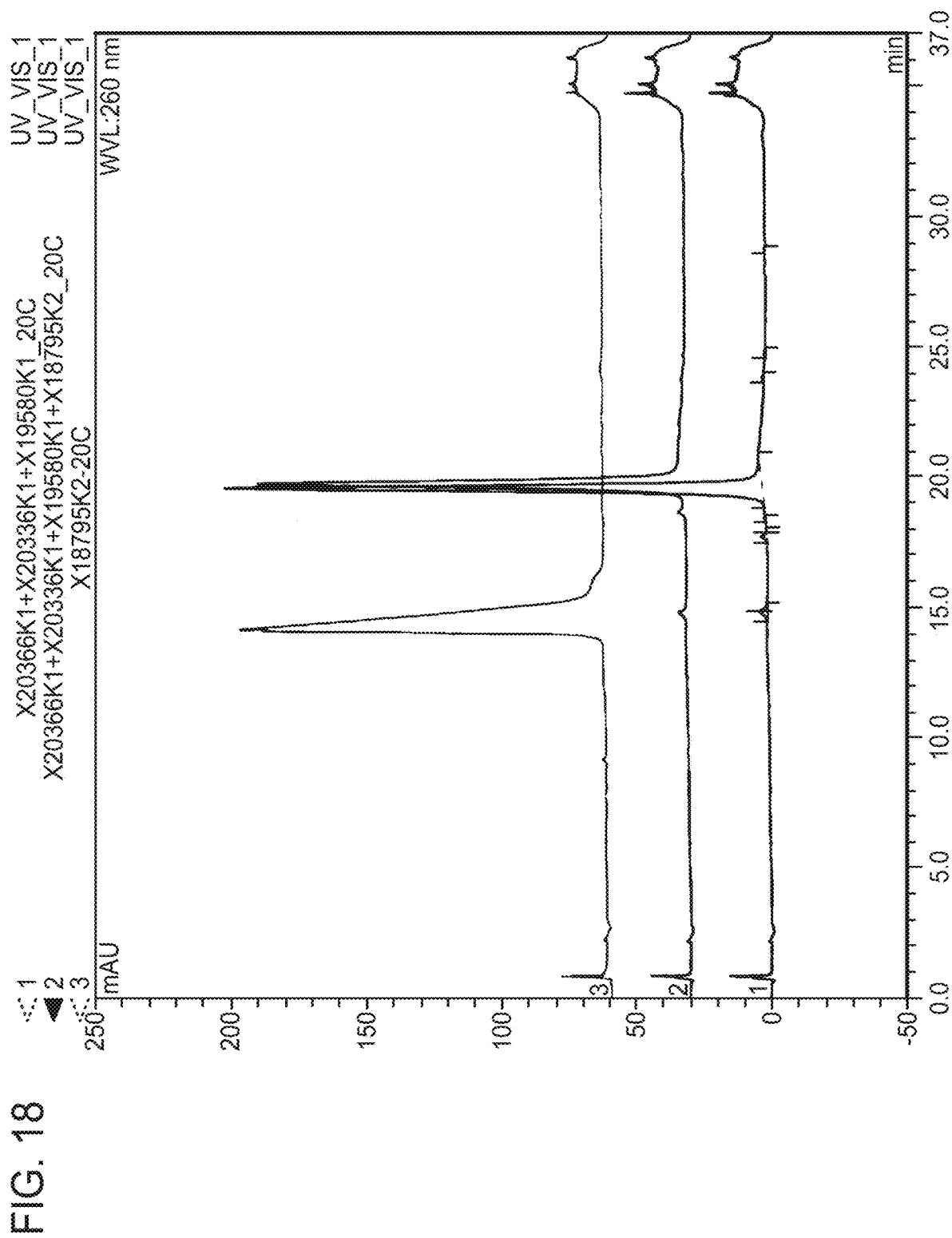
FIG. 18 presents data for an HPLC analysis of addition of X18795 (5'-siFVIIantisense-3') to reaction mixture to yield XD-06727, which is discussed in connection with Example 18.
Figure 19A:
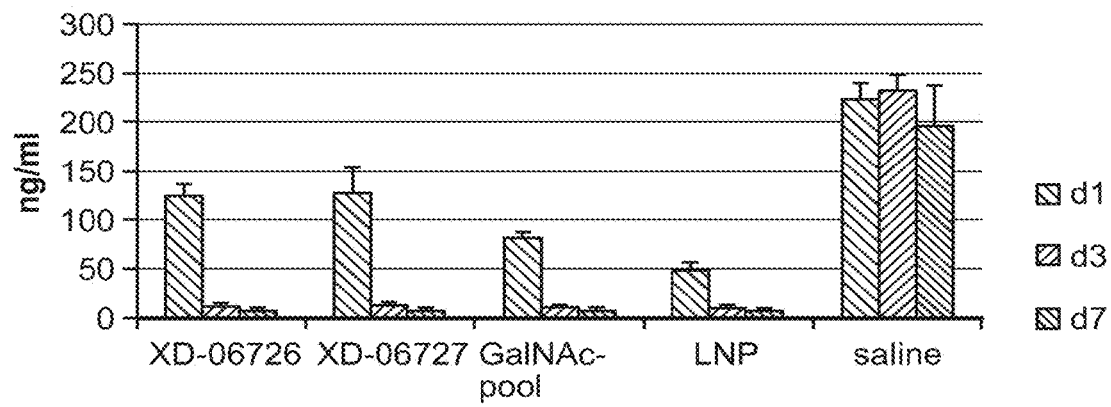
FIGS. 19A and 19B present data for TTR protein levels in serum samples (measured by ELISA), which is discussed in connection with Example 20.
Figure 19B:
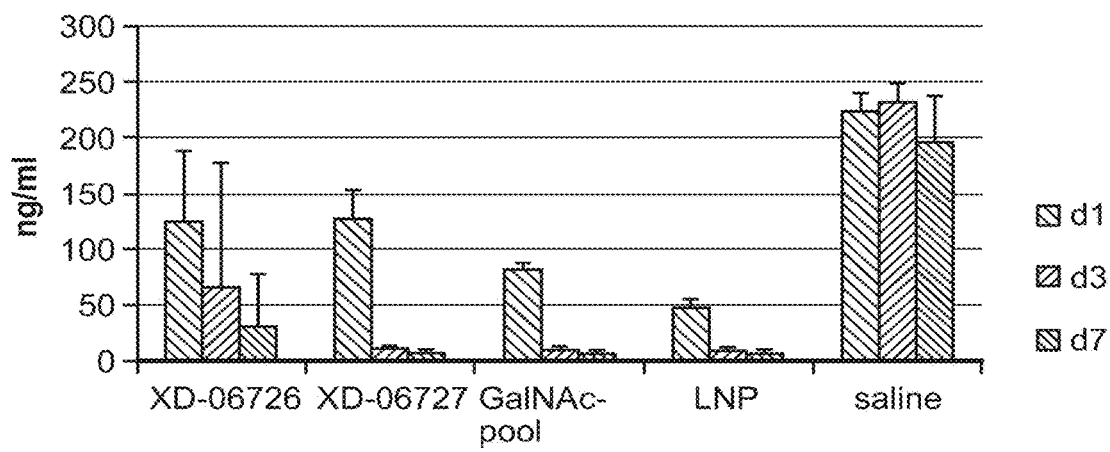
Figure 20A:
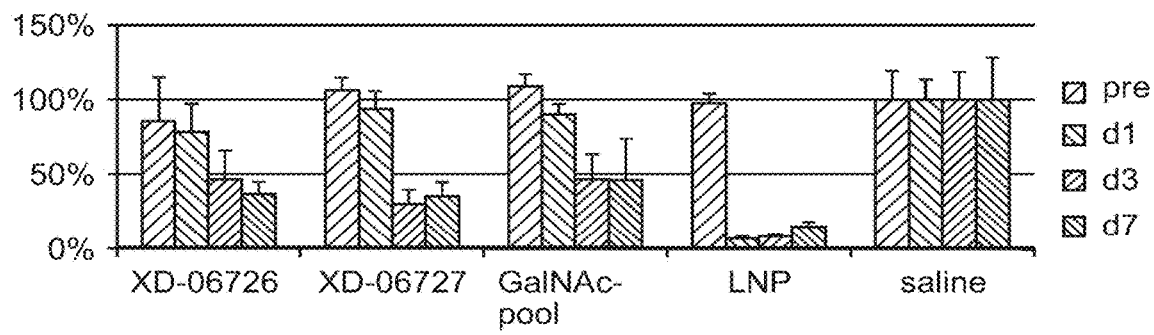
FIGS. 20A and 20B present data for FVII enzymatic activity in serum samples, which is discussed in connection with Example 20.
Figure 20B:
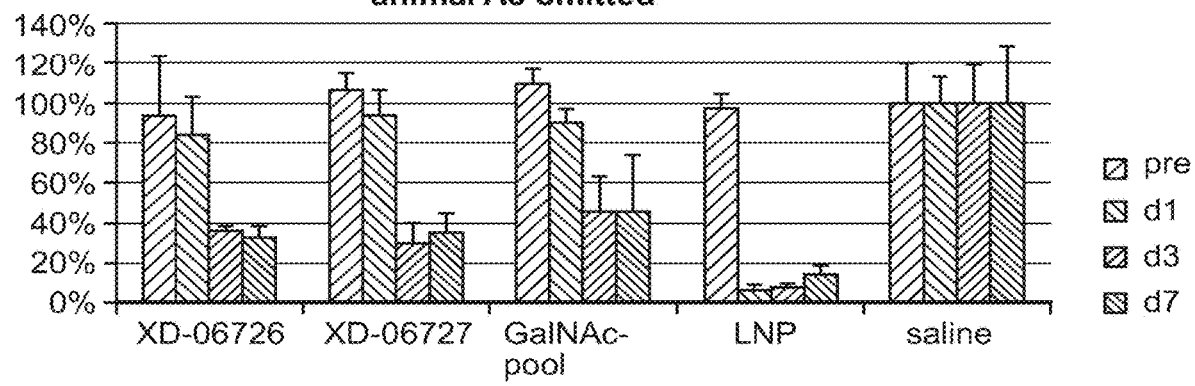
Figure 21A:
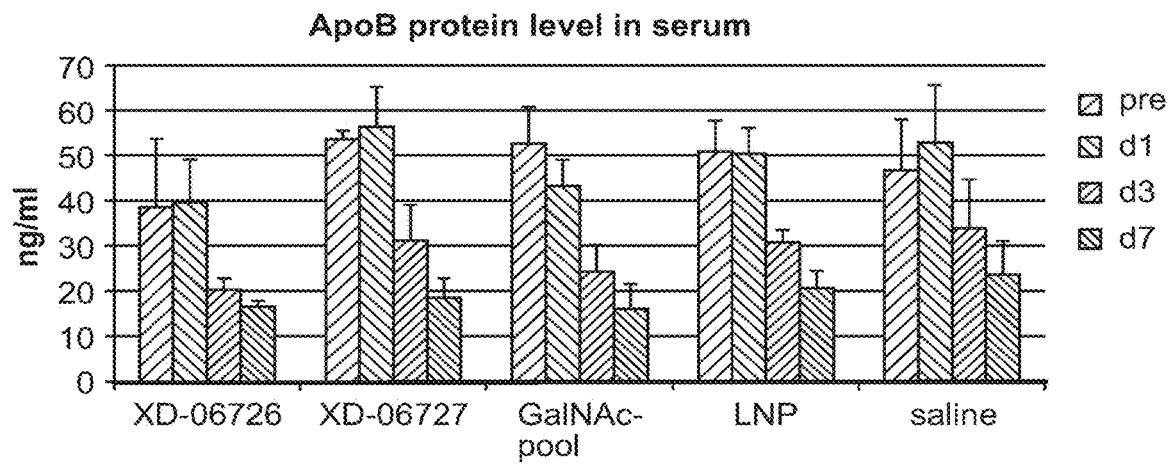
FIGS. 21A and 21B present data for ApoB protein levels in serum samples (measured by ELISA), which is discussed in connection with Example 20.
Figure 21B:
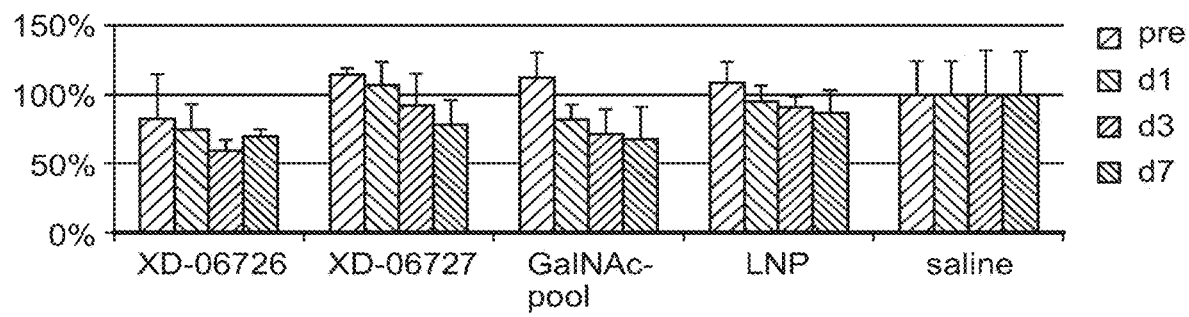

The synthesis that produced the heterotrimer (XD-06727) is highly efficient. In this example, nearly 100% conversion of the reactants was achieved at each step. See FIGS. 16, 17, and 18.

Example 19: Preparation of LNP Formulation of Pooled siRNAs Individually Targeting FVH, ApoB and TTR Monomeric siRNAs targeting FVII (XD-00030), ApoB (XD-01078) and TTR (XD-06729 were formulated in Lipid Nanoparticles and characterized using the methodologies described in General Procedure: Lipid Nanoparticle Formulation and General Procedure: LNP Characterization. The lipid composition was XL10:DSPC:Cholesterol:PEG-DOMG/50:10:38.5:1.5 molar percent. 88% encapsulation was achieved and the resulting particles were 83 nm in size with a zeta potential of 2.2 mV and a PDI of 0.04.

Figure 22A:
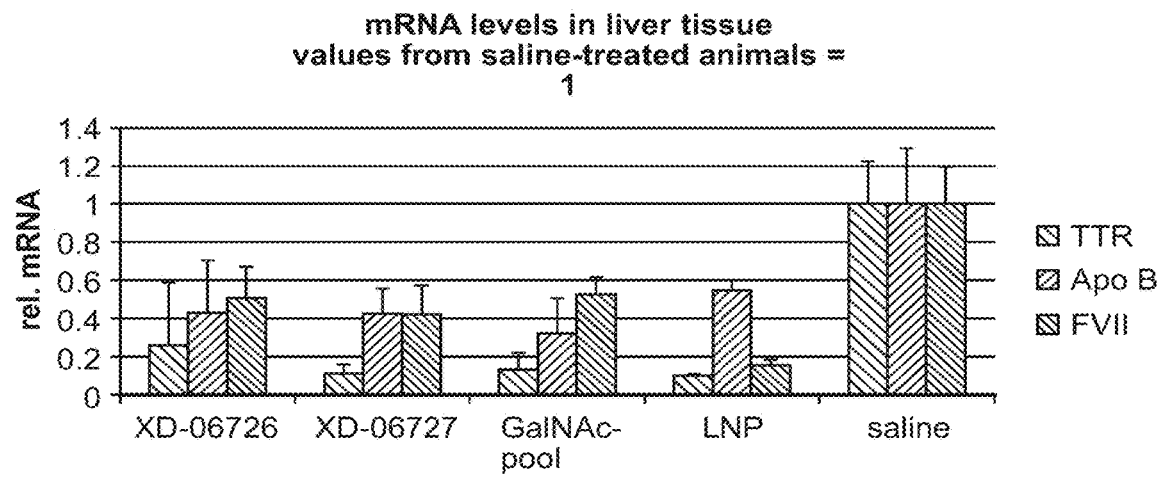
FIGS. 22A and 22B present target knockdown in liver data, which is discussed in connection with Example 20.
Figure 22B:
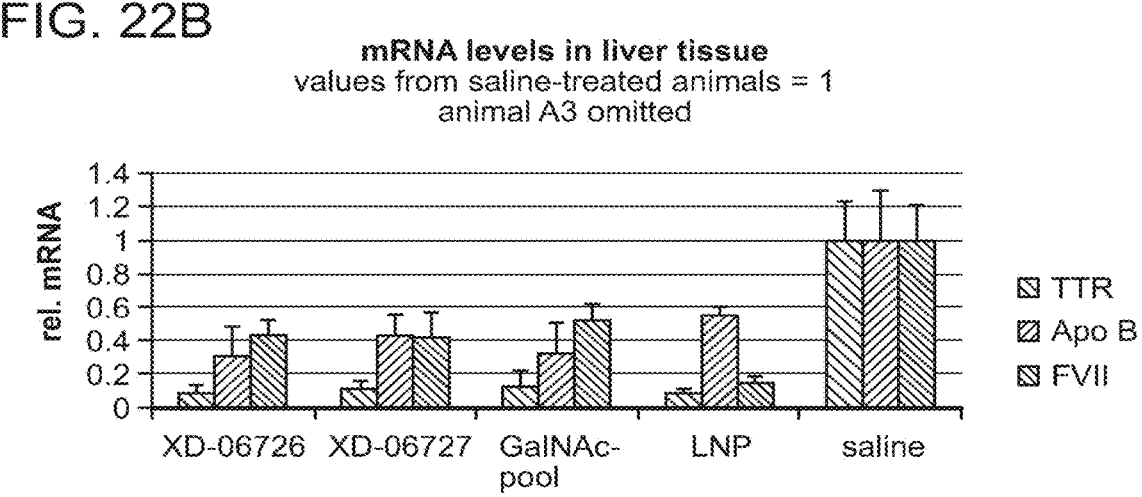

Example 20: Assessment of mRNA Knockdown by GalNAc-Conjugated Heterotrimeric SiRNAs To determine the in vivo efficacy of heterotrimeric GalNAc-conjugated siRNAs (targeted to FVII, ApoB and TTR), an animal experiment was performed as described above (General Procedure: Animal Experiments) using a group size of n=4 mice for treatment groups and n=5 for saline controls. The heterotrimers XD-06726 and XD-06727 as well as a pool of 3 monomeric GalNAc-conjugated siRNAs (XD-06328 targeting FVII; XD-06386 targeting TTR and XD-06728 targeting ApoB) were injected subcutaneously (0.1 mL volume) at a concentration of 50 mg/kg total RNA for the trimers and 17 mg/kg for each of the monomeric conjugates. For comparison, a pool of LNP-formulated siRNAs (NPA-741-1) directed against the same targets (FVII (XD-00030), ApoB (XD-01078) and TTR (XD-06729)) was injected intravenously at 0.5 mg/kg per siRNA. Blood was collected as described above (General Procedure: Animal Experiments) 1 day prior to treatment and at 1, 3 and 7 days post-treatment, and serum levels of FVII, ApoB and TTR measured according to the General Procedures: Measurement of Gene Knockdown. Results are shown in FIGS. 19A and 19B, 20A and 20B, and 21A and 21B. mRNA levels in liver lysates were measured at day 7 post injection (FIGS. 22A and 22B).

One animal in group A (XD-06726) did not show any effect on TTR serum levels. The second of the two TTR protein graphs shows data with values omitted for the non-responding animal.

For comparison, the values from the animal showing poor TTR response have been omitted from the second FVII graph.

ApoB serum levels show a high variation, both within the animals of one group and between the different time-points of the saline control.

Knockdown of all three genes was also measured using a bDNA assay for mRNA from liver tissue according to the General Procedures: Measurement of Gene Knockdown, above. Target gene levels were normalized to the housekeeper GAPDH.

Example 21: Preparation
GalNAc-FVII-ApoB-TTR-FVII Tetramer
(XD-07140)

Figure 23:
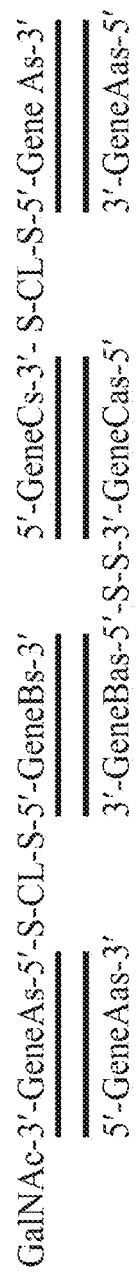
FIG. 23 presents a GalNAc-heterotetramer conjugate (XD-07140), which is discussed in connection with Example 21. Key: In this example, "GeneA" is siFVII; "GeneB" is siApoB; and "GeneC" is siTTR.
Figure 24:
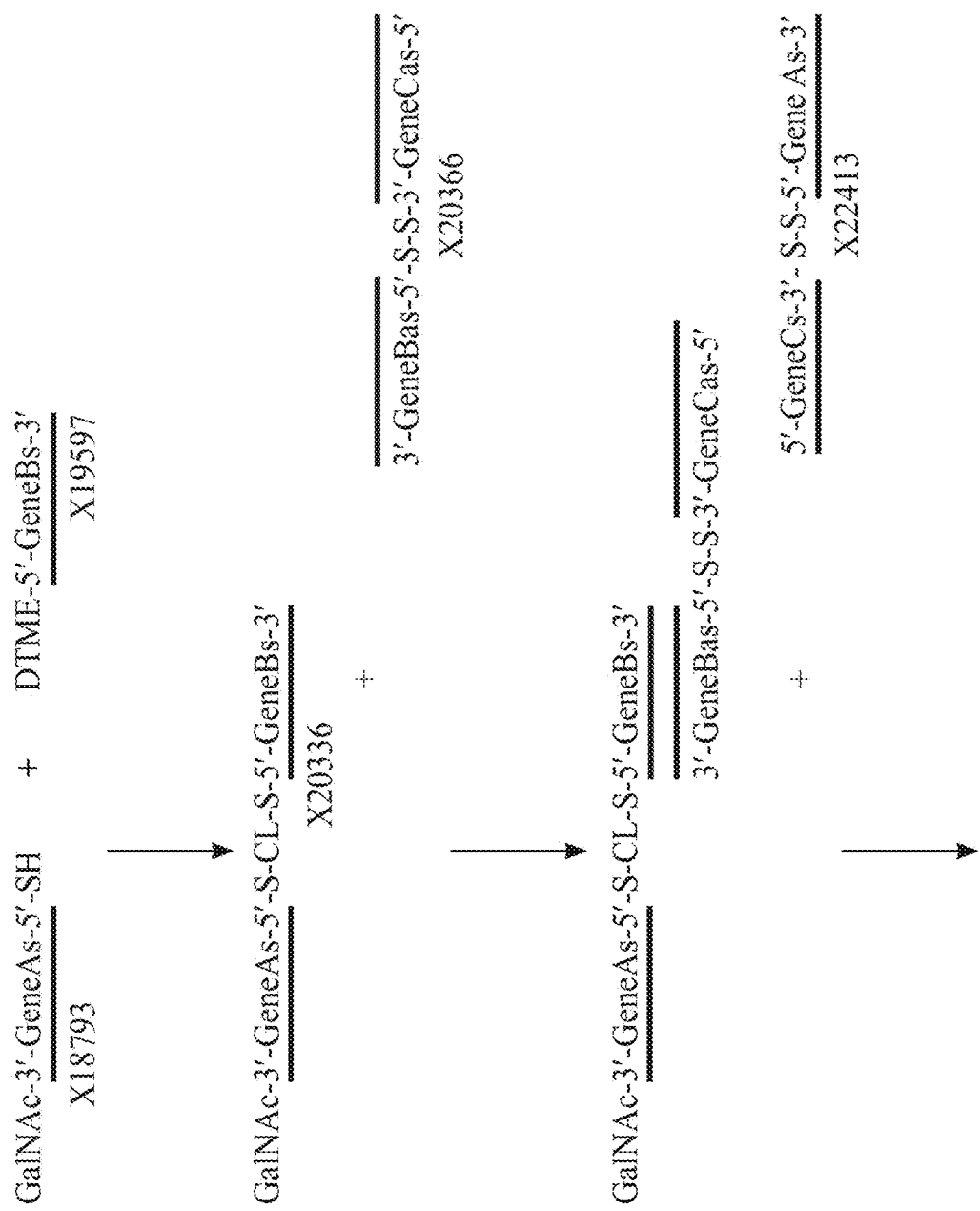
FIG. 24 presents a schematic of a synthesis of a GalNAc-heterotetramer conjugate (XD-07140), which is discussed in connection with Example 21. Key: In this example, "GeneA" is siFVII; "GeneB" is siApoB; and "GeneC" is siTTR.
Figure 24:
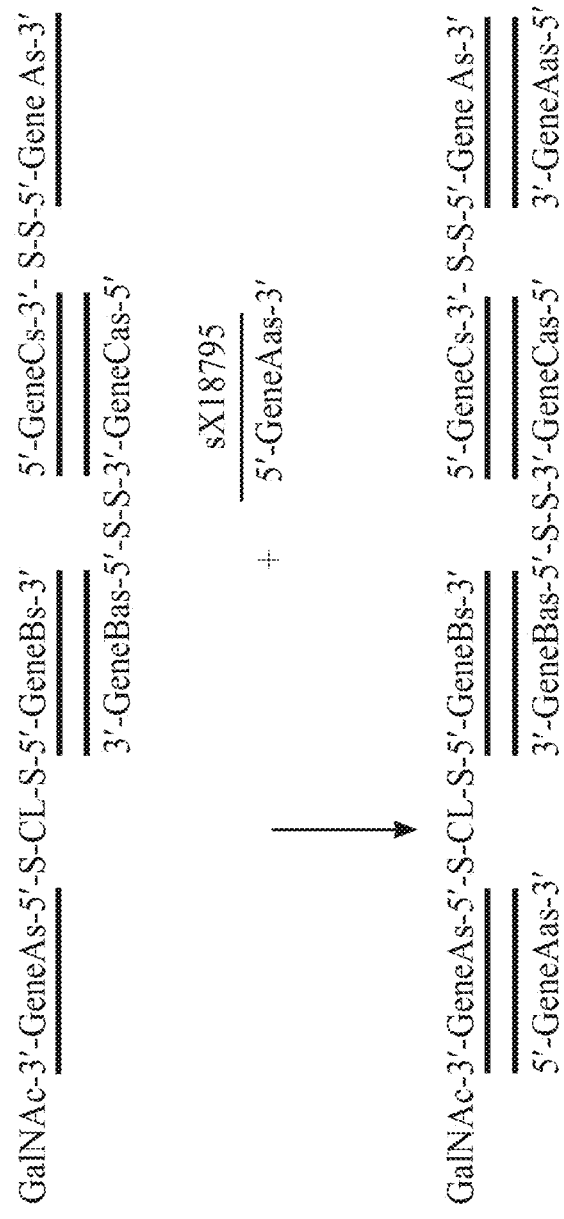
Figure 25:
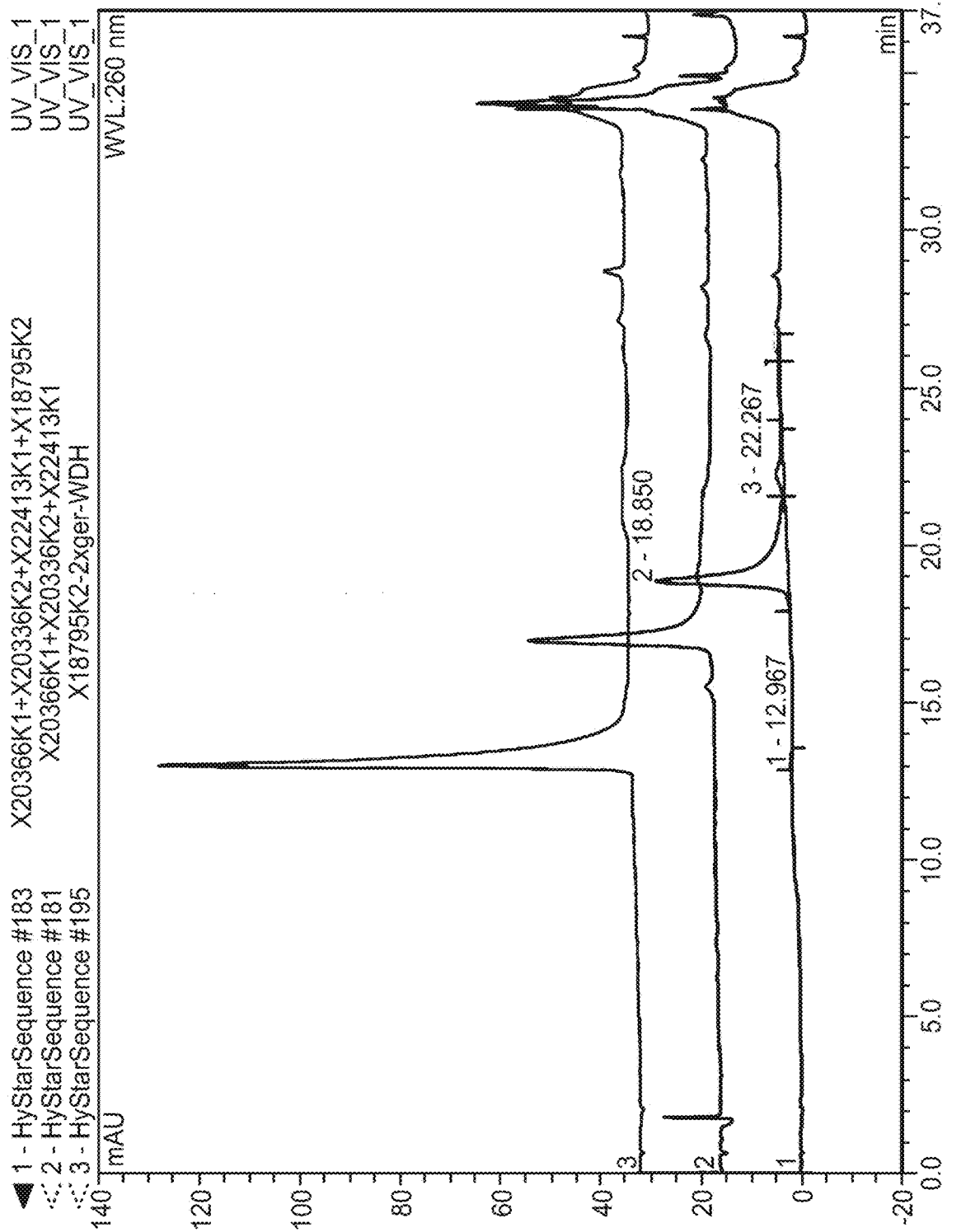
FIG. 25 presents a HPLC Analysis of a GalNAc-siFVII-siApoB-siTTR-siFVII Tetramer (XD-07140), which is discussed in connection with Example 21.

12.4 nmol of the tetrameric siRNA XD-07140 (see FIG. 23), simultaneously targeting FVII, ApoB and TTR, was prepared by combining single strands stepwise as depicted in FIG. 24, and according to the duplex titration method described in Example 8. HPLC analysis showed the product was obtained in high purity.

TABLE 14

Stoichiometries of Oligomers used in Synthesis of
GalNAc-FVII-ApoB-TTR-FVII Tetramer (XD--07140)

| SEQ ID | ID | Target | E (L/mol * cm) | 1 OD | MW (free Acid) | MW Na salt | Req OD |
|---|---|---|---|---|---|---|---|
| 42 | X20336 | FVIIs-ApoBs | 404300 | 2.47 nmol | 15440.1 | 16341.4 | 5 |
| 49 | X20366 | ApoBas-TTRas | 446700 | 2.24 nmol | 14748.9 | 15716.1 | 5.5 |
| 45 | X22416 | TTRs-FVIIs | 412100 | 2.52 nmol | 14041.3 | 14964.5 | 4.9 |
| 26 | X18795 | FVIIas | 194800 | 5.13 nmol | 6849.4 × 2 | 7289.1 × 2 | 4.8 |
| 55 | XD-07140 | | | | 57929.1 | 46913.8 | |

Example 22: Generation of Mixtures of Multimeric siRNAs

Mixtures of multimeric siRNAs in dynamic equilibria, and methods of manufacturing them, are described in Mok et al., "Multimeric small interfering ribonucleic acid for highly efficient sequence-specific gene silencing," NATURE MATERIALS, Vol. 9, March 2010. As described therein, the mixtures comprise linear chains of chemically linked siRNAs, wherein the chains are of varying lengths. In this Example, there follows a series of experiments conducted to investigate the effect of different annealing conditions on the efficiency of the Mok et al. synthesis reaction and the characteristics of the final product.

TABLE 15

Starting Materials for Multimeric siRNA Mixtures

| SEQ ID | Description | Axo ID | Sequence (5'-3') |
|---|---|---|---|
| 13 | F7 sense (s) | X01162 | GGAUfCfAUfCfUfCfAAGUfCfUfUfACfdTsdT |
| 56 | 3'-thiol-F7s | X12006 | GGAUfCfAUfCfUfCfAAGUfCfUfUfACfdTsdT (SHC6) |
| 14 | F7 antisense (as) | X00549 | GUfAAGACfUfUfGAGAUfGAUfCfCfdTsdT |
| 57 | 3'-thiol-F7as | X12007 | GUfAAGACfUfUfGAGAUfGAUfCfCfdTsdT (SHC6) |
| 58 | F7 homodimer (s-c-s) | X12710 | GGAUfCfAUfCfUfCfAAGUfCfUfUfACfdTsdT (SHC6)(DTME) GGAUfCfAUfCfUfCfAAGUfCfUfUfACfdTsdT (SHC6) |
| 59 | homodimer (as-c-as) | X12711 | GUfAAGACfUfUfGAGAUfGAUfCfCfdTsdT (SHC6)(DTME) GUfAAGACfUfUfGAGAUfGAUfCfCfdTsdT (SHC6) |
| 60 | homodimer (s-nc-s) | X12712 | GGAUfCfAUfCfUfCfAAGUfCfUfUfACfdTsdT (SHC6)(BMPEG2) GGAUfCfAUfCfUfCfAAGUfCfUfUfACfdTsdT (SHC6) |
| 61 | homodimer (as-nc-as) | X12713 | GUfAAGACfUfUfGAGAUfGAUfCfCfdTsdT(SHC6) (BMPEG2) GUfAAGACfUfUfGAGAUfGAUfCfCfdTsdT (SHC6) |

Key: In the Description portion of the chart: "F7" means siRNA sequence targeting the Factor VII gene (also known as Factor VII). Sense strand is designated "s"; antisense strand is designated "as". The chemical linkers joining the strands are designated as "c" for cleavable and "nc" for noncleavable.

In the Sequence portion of this chart (and those that follow): upper case letters "A", "C", "G" and "U" represent RNA nucleotides. Lower case letter "s" represents phosphorothioate and "dT" represents deoxythymidine residues. Upper case letters A, C, G, U followed by "f" indicate 2'-fluoro nucleotides. "(SHC6)" represents a thiohexyl linker. "(DTME)" represents the cleavable homobifunctional crosslinker dithiobismaleimidoethane. "(BMPEG2)" represents the non-cleavable homobifunctional crosslinker 1,8-bismaleimido-diethyleneglycol. In general, sequences are written from the 5'- to the 3'-terminus; however, sequences comprising the DTME or BMPEG2 crosslinker are linked via the 3'-ends, and in these sequences the second half needs to be read from right to left, i.e., 3'- to 5'.

The sequences shown in Table 15 were made following the synthetic methodology described above in General Procedure: Single Chain Oligonucleotide Synthesis.

Figure 26:
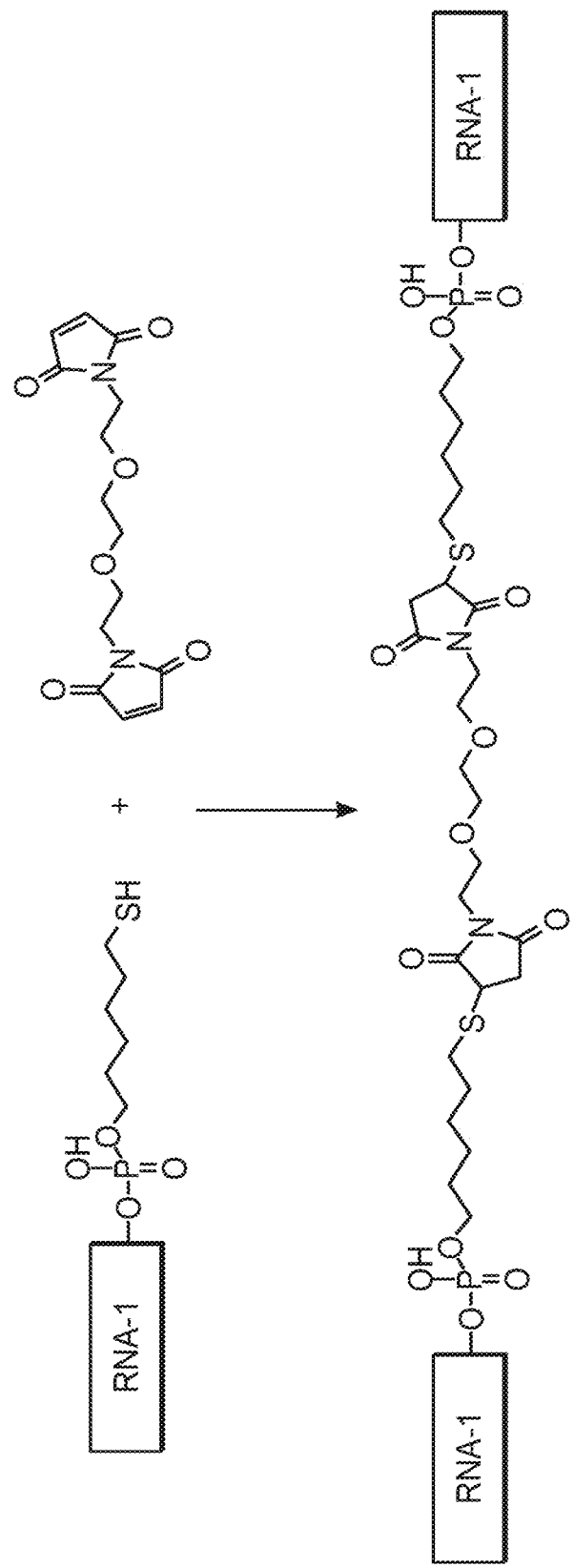
FIG. 26 presents a synthesis of a homodimer, which is discussed in connection with Example 22.

Subsequent to the solid phase assembly of the sequences, deprotection and preparative AEX HPLC purification of the sense and antisense oligonucleotides, the single stranded homodimers were formed by combining the 3'-thiol modified single stranded oligonucleotide and the respective homobifunctional crosslinker (DTME or BMPEG2, both purchased from Pierce). To this end, the oligonucleotide was dissolved in 100 mM triethylammonium acetate, pH 7, to give a 1.4 mM solution. A freshly prepared solution of the homobifunctional crosslinker (5 mg/mL) in acetonitrile was added to the solution containing the oligonucleotide. The reaction mixture was agitated at 25° C. on a thermoshaker. The reaction was monitored by analytical AEX HPLC using a Dionex DNA Pac 200 column (4×250 mm). Once the starting material was consumed the reaction was quenched by the addition of a mixture of sodium acetate (3M, pH 5.2) and ethanol 1:32 (v/v). The crude material was precipitated overnight in the freezer. The pellet was dissolved in water and purified by AEX HPLC using a column filled with source 15 Q resin (GE Healthcare). Fractions of appropriate purity were combined and precipitated again. The pellet was dissolved in water and quantified by measuring the absorption at 260 nm. A generic depiction of the synthesis of a homodimer using BMPEG2 as linker is shown in FIG. 26.

Analytical data for the sequences shown in the Table 15 above are listed in Table 16, as follows:

TABLE 16

Analytical Data for Starting Materials

| Description | ID | Purity (IEX HPLC, %) | Mol weight (calculated) | Mol weight (measured) |
|---|---|---|---|---|
| F7 sense (s) | X01162 | 93.5 | 6629.1 | 6629.4 |
| 3'-thiol-s | X12006 | 93.4 | 6826.4 | 6825.3 |
| F7 antisense (as) | X00549 | 94.2 | 6726.2 | 6726.0 |
| 3'-thiol-as | X12007 | 94.2 | 6923.4 | 6922.1 |
| homodimer (s-c-s) | X12710 | 84.9 | 13967.2 | 13969.3 |
| homodimer (as-c-as) | X12711 | 87.2 | 14159.2 | 14157.7 |
| homodimer (s-nc-s) | X12712 | 89.9 | 13961.1 | 13959.7 |
| homodimer (as-nc-as) | X12713 | 87.2 | 14155.1 | 14153.1 |

Table 17 shows the single stranded homodimers that were annealed to produce duplexed multimeric siRNA mixtures, XD-05305 (having noncleavable linkages) and XD-05306 (having cleavable linkages). Initially, generic annealing conditions were used: complementary single strands were combined in 1×PBS and placed into a water bath kept at 70° C. for 10 minutes. Then, the water bath was cooled down to 25° C. over a period of 3 hours.

TABLE 17

Sequences Used in Production of Duplexed Multimeric siRNA Mixtures

| Duplex-ID | Description | Axo ssRNA ID | Sequence (5'-3') |
|---|---|---|---|
| XD-05305 | (s-nc-s) | X12712 | GGAUfCfAUfCfUfCfAAGUfCfUfUfUfACfdTsdT(SHC6)(BMPEG2)GGAUfCfAUfCfUfCfAAGUfCfUfUfUfACfdTsdT(SHC6) |
|  | (as-nc-as) | X12713 | GUfAAGACfUfUfGAGAUfGAUfCfCfdTsdT(SHC6)(BMPEG2)GUfAAGACfUfUfGAGAUfGAUfCfCfdTsdT(SHC6) |
| XD-05306 | (s-c-s) | X12710 | GGAUfCfAUfCfUfCfAAGUfCfUfUfUfACfdTsdT(SHC6)(DTME)GGAUfCfAUfCfUfCfAAGUfCfUfUfUfACfdTsdT(SHC6) |
|  | (as-c-as) | X12711 | GUfAAGACfUfUfGAGAUfGAUfCfCfdTsdT(SHC6)(DTME)GUfAAGACfUfUfGAGAUfGAUfCfCfdTsdT(SHC6) |

Figure 27:
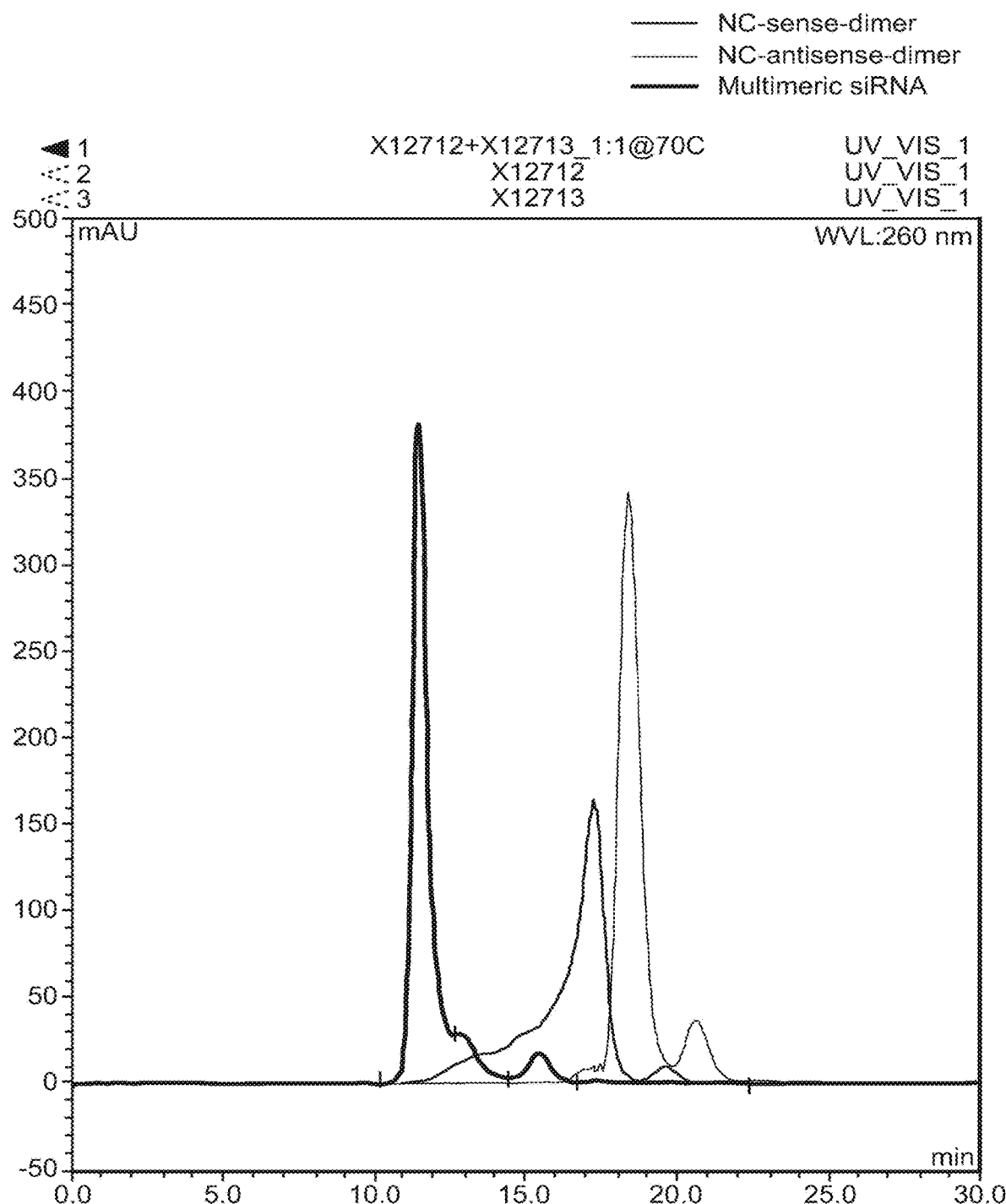
FIG. 27 presents an SEC HPLC analysis of XD-05305, which is discussed in connection with Example 22.

In order to establish a baseline for potentially improved annealing conditions over those shown in the prior art (Mok et al, NATURE MATERIALS, Vol. 9, March 2010), the non-cleavable homodimers X12712 and X12713 were used. A comparison of the annealing conditions published by Mok et al. (hereinafter "Park") and a proprietary set of standard annealing conditions (hereinafter "Axolabs" conditions) was conducted. The Park conditions were: 1×PBS, 1 hour, 37° C. The Axolabs conditions were: 1×PBS, 10 minutes at 70° C., cooling down to 25° C. over a period of 3 hours. FIG. 27 demonstrates that SEC HPLC separates single stranded dimers from multimeric siRNA. The NC-sense-dimer corresponds to the middle peak, the NC-antisense-dimer corresponds to the right peak, and the multimeric siRNA corresponds to the left peak.

Figure 28:
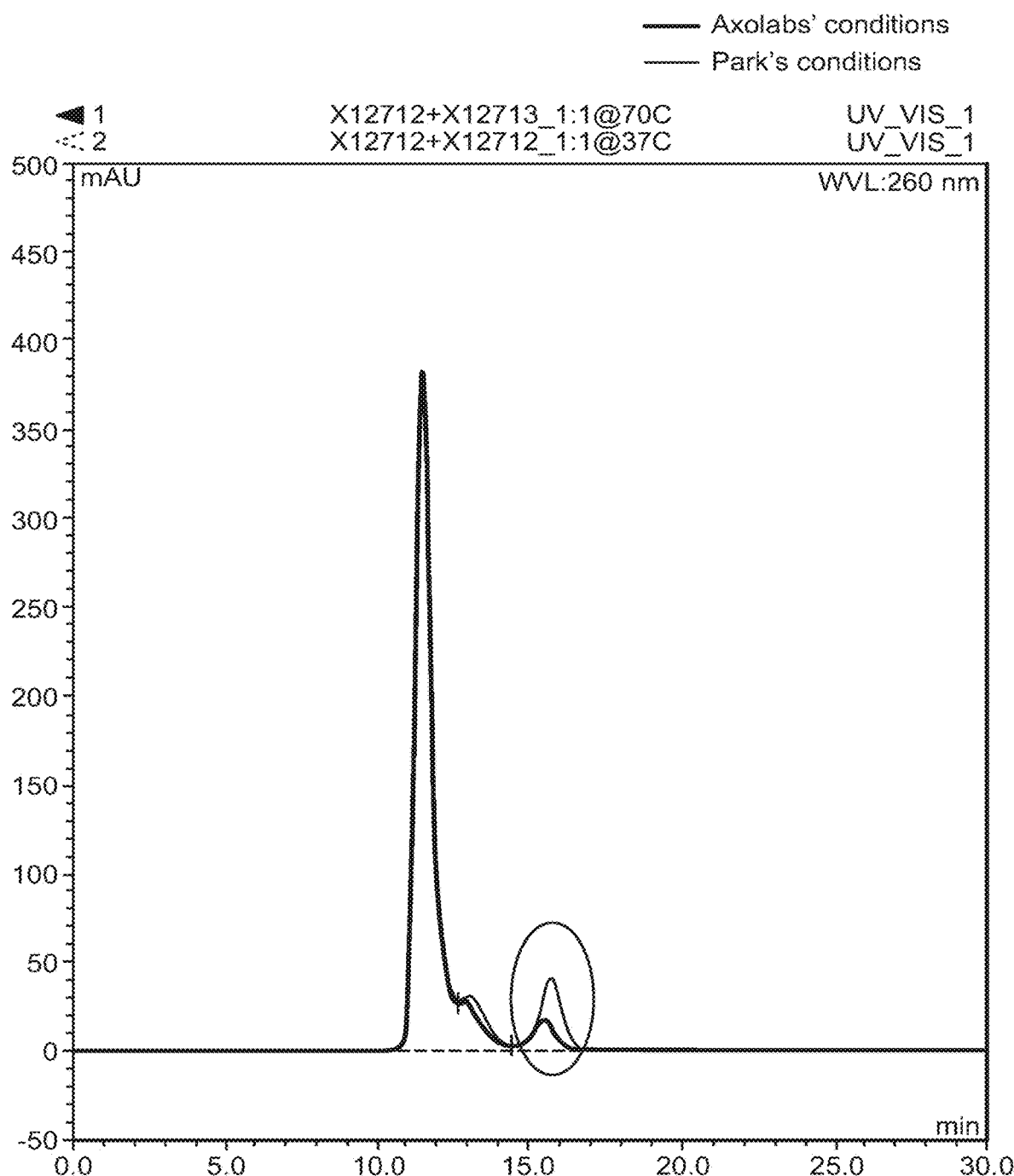
FIG. 28 presents an SEC HPLC Analysis of XD-05305, which is discussed in connection with Example 22.

Further, FIG. 28 demonstrates that the integral of the multimeric siRNA appears to be independent of the annealing conditions; whereas the fraction of short dsRNA is not. The higher peak in the circled region around t=15.0 min corresponds to the "Park's conditions" and the lower peak in the circled region corresponds to the "Axolabs' conditions."

The Axolabs annealing conditions shift more material into the multimeric siRNA fraction.

Figure 29:
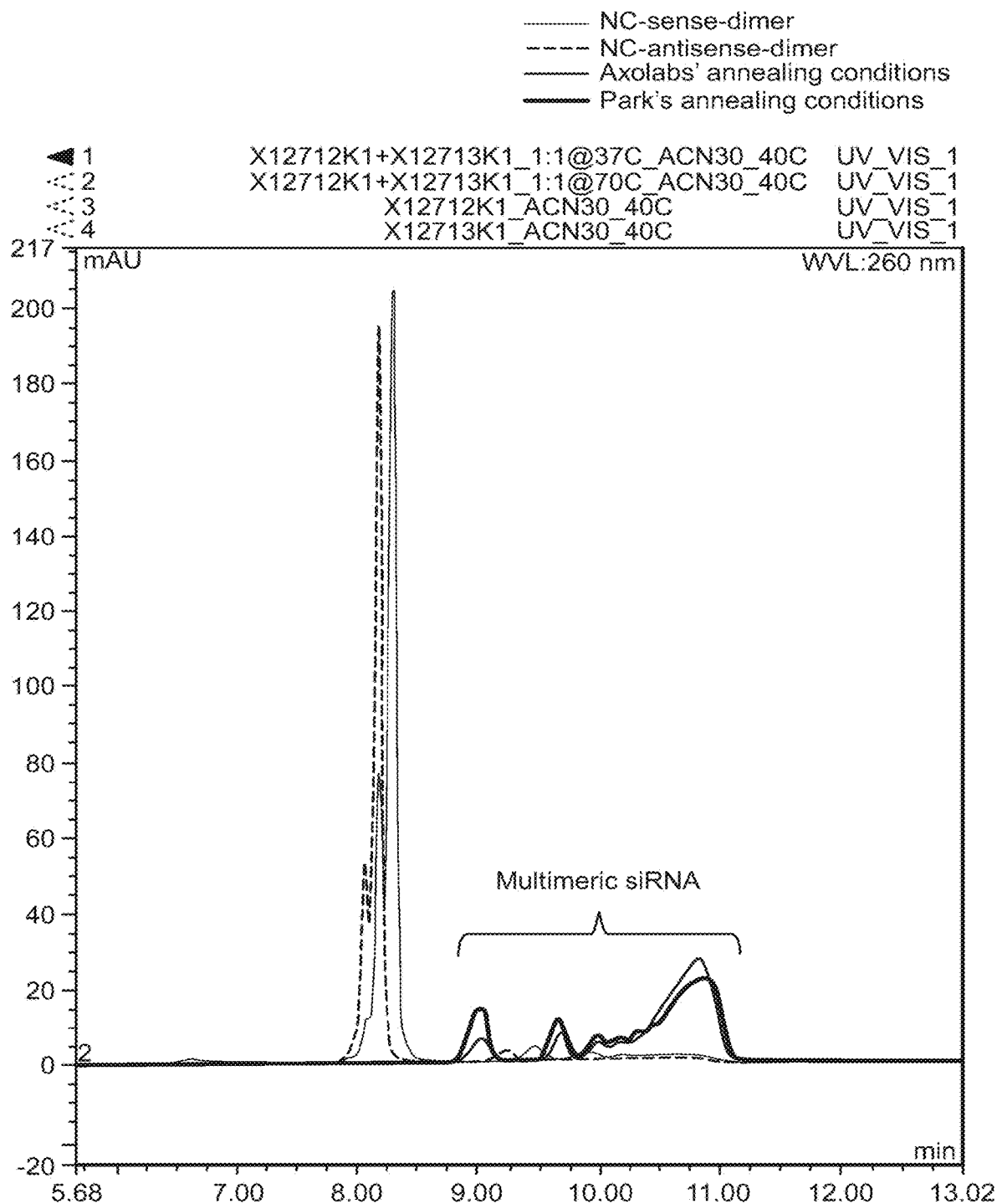
FIG. 29 presents an IEX HPLC analysis of XD-05305, which is discussed in connection with Example 22.

Scouting of a series of different native HPLC conditions (buffer, temperature, content of acetonitrile) resulted in the ability to partially separate the multimeric siRNAs, as demonstrated in FIG. 29. The highest peak corresponds to the NC-sense-dimer, the leftmost peak corresponds to the NC-antisense dimer, the highest peak in the "multimeric siRNA" region around t=9-11 min corresponds to the "Axolabs' annealing conditions," and the second highest peak in the "multimeric siRNA" region corresponds to "Park's annealing conditions."

Further, this analysis confirmed that annealing at higher temperature minimizes shorter multimers and favors longer ones. Further, we found that using SEC and IEX HPLC analysis, it was not possible to assign the distribution of X-mer siRNAs in the mixtures analyzed.

Figure 30:
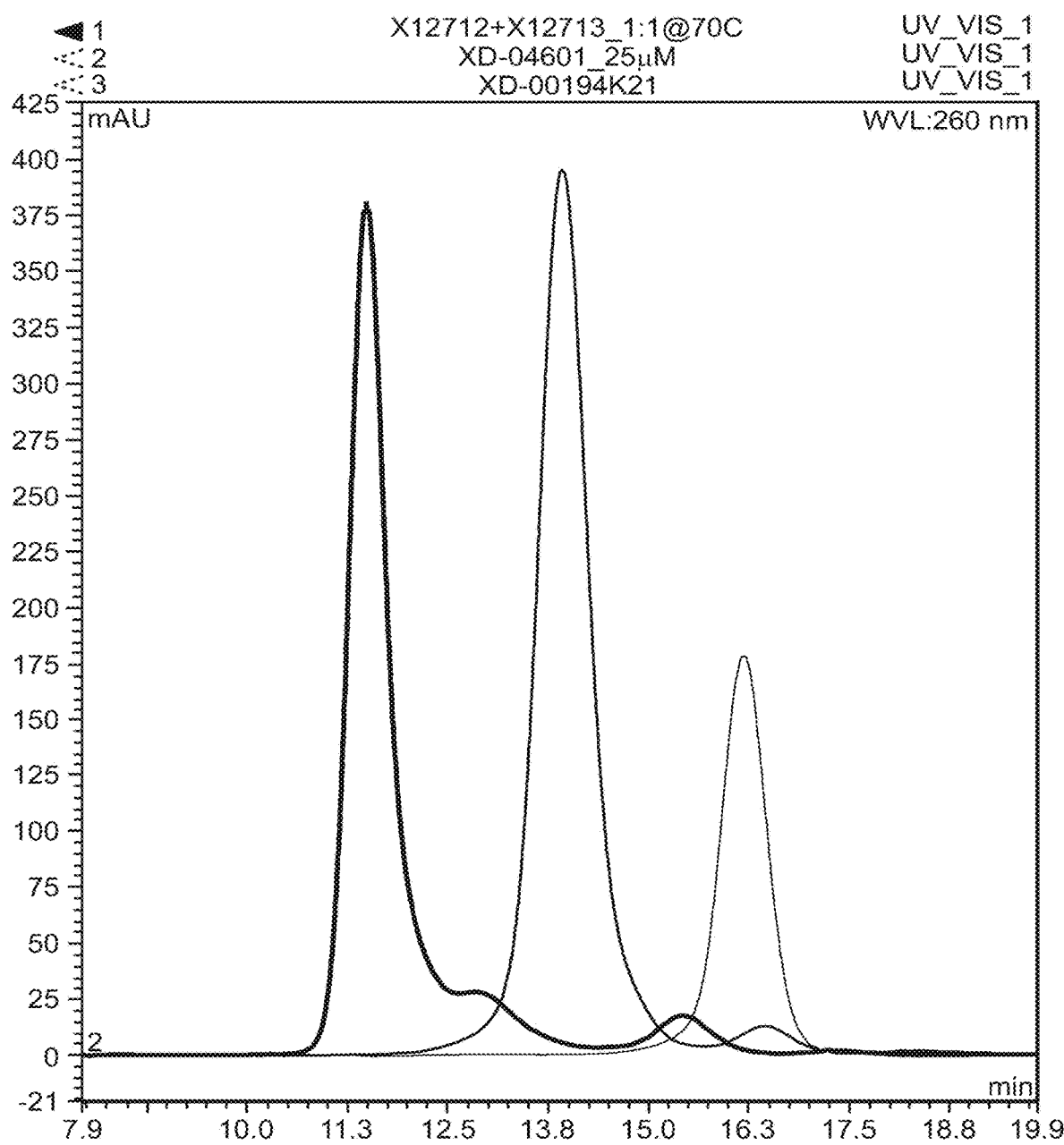
FIG. 30 presents an SEC HPLC analysis of XD-05305, which is discussed in connection with Example 22. Multimeric siRNA is the left-hand peak; dimeric siRNA is the middle peak; and canonical siRNA is the right-hand peak.

Baseline separation of various siRNA constituents of the multimeric siRNA mixtures was achieved by SEC HPLC Analysis, as shown in FIG. 30. Multimeric siRNA is the left-hand peak; dimeric siRNA is the middle peak; and canonical siRNA is the right-hand peak.

Using HPLC-based methods and a Superdex 200 10/300 GL column, additional annealing conditions were investigated with the aim to minimize the fraction of material that rarely oligomerizes. Specifically, Table 18 shows the parameters that were analyzed and the results that were obtained using the noncleavable F7 homodimers.

Based on these results, it was determined that optimized annealing conditions comprise high RNA concentration (~250 µM), low salt concentration (~0.2×PBS), reaction temperature around 70-80 (for about 10 min), and slow cooling to room temperature (2 h).

Figure 31:
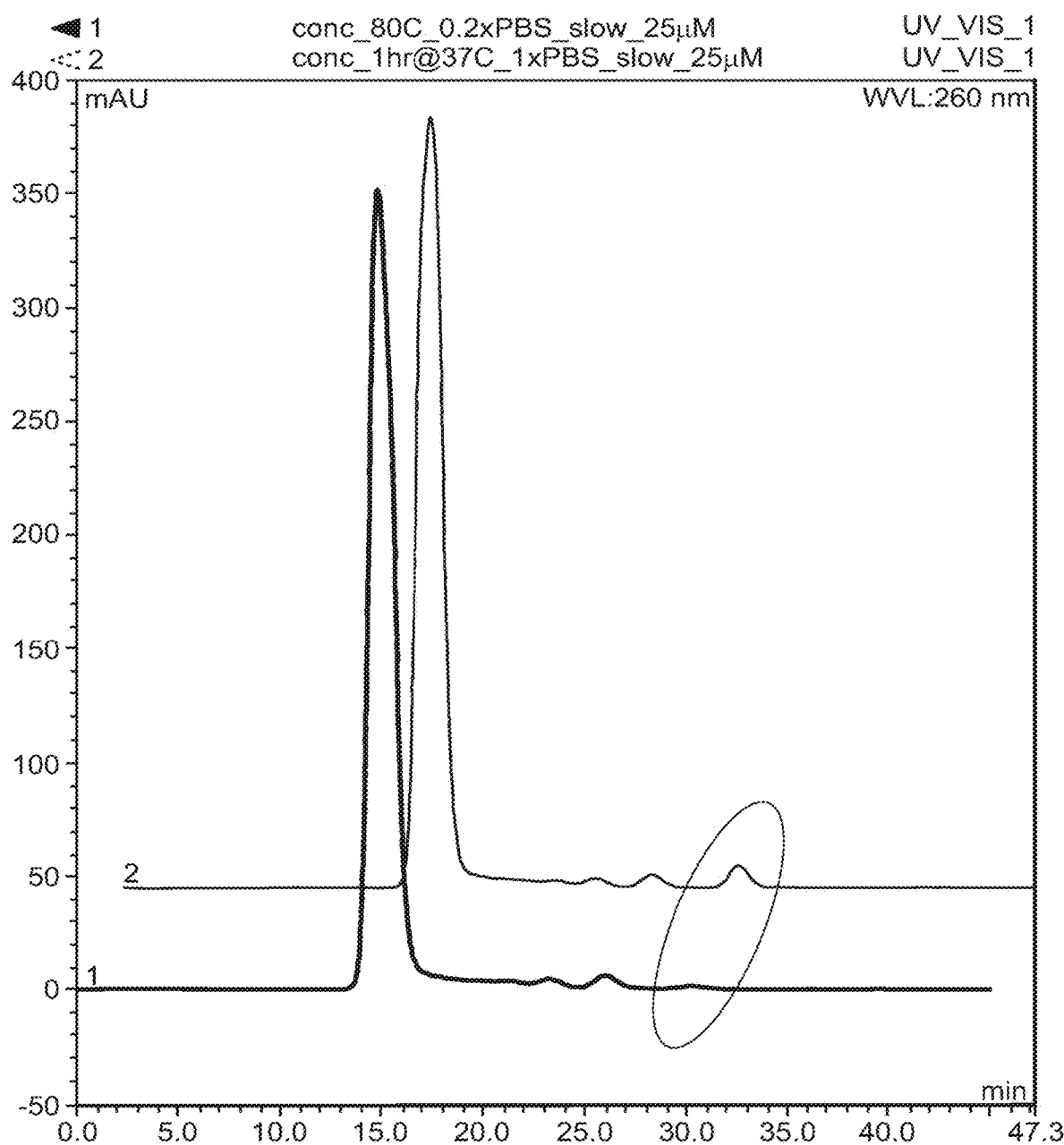
FIG. 31 presents the effect of salt concentration and reaction temperature on a multimeric siRNA mixture, which is discussed in connection with Example 22.

FIG. 31 demonstrates the effect of salt concentration and reaction temperature on the multimeric siRNA mixture.

Next the optimized annealing conditions were selected and two additional experiments were run to determine if it is possible to control the reaction so as to minimize the amount of extremely high molecular weight multimeric species in the final mixture (on the theory that the lower molecular weight species will be more active in vivo and potentially more easily formulated into LNP, if LNP is used as a delivery vehicle).

Figure 32:
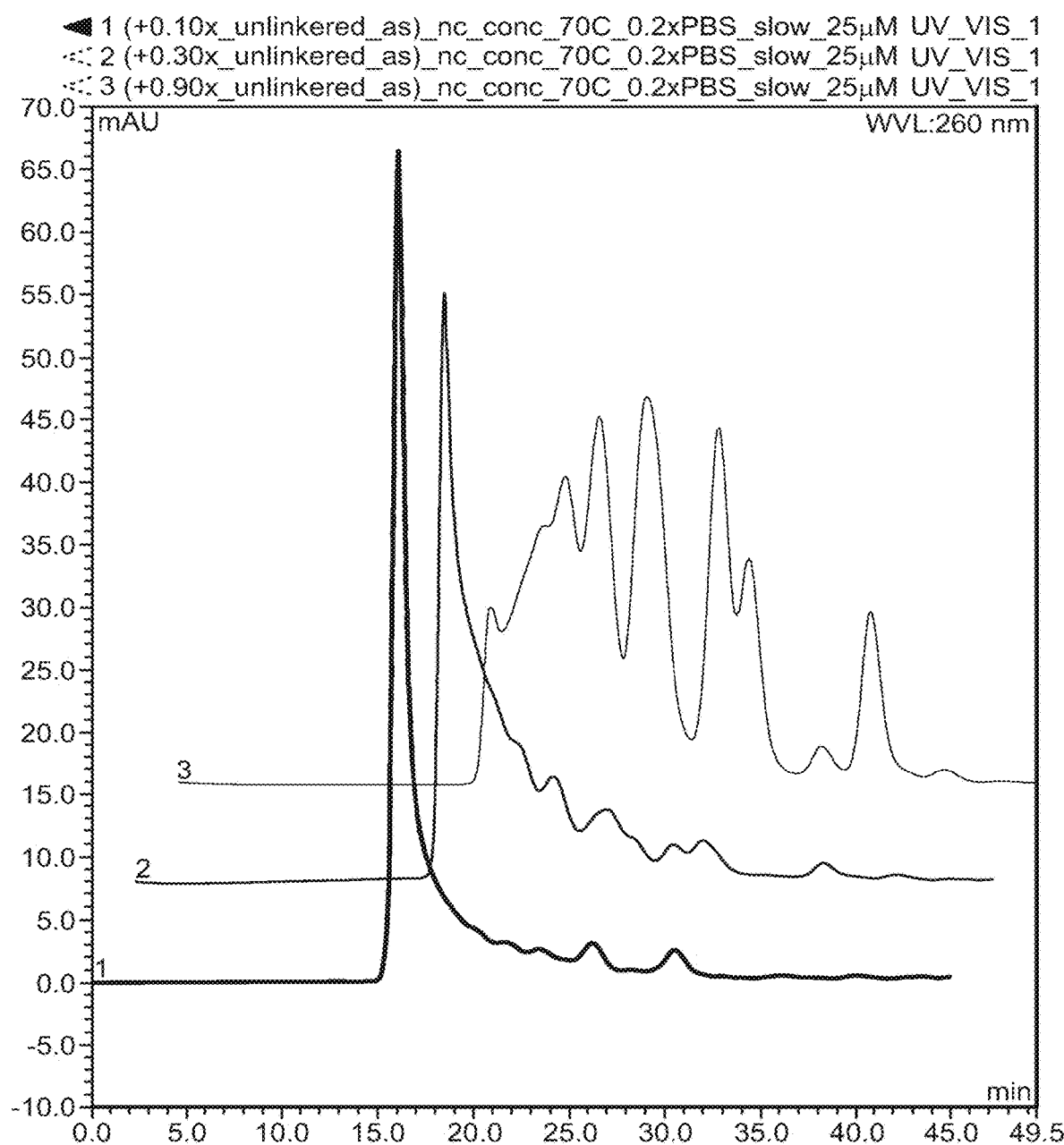
FIG. 32 presents data showing that the higher the concentration of termination strand (in this case, the antisense strand was used as the terminator), the smaller the multimerized siRNA fraction. The data is discussed in connection with Example 22.
Figure 33:
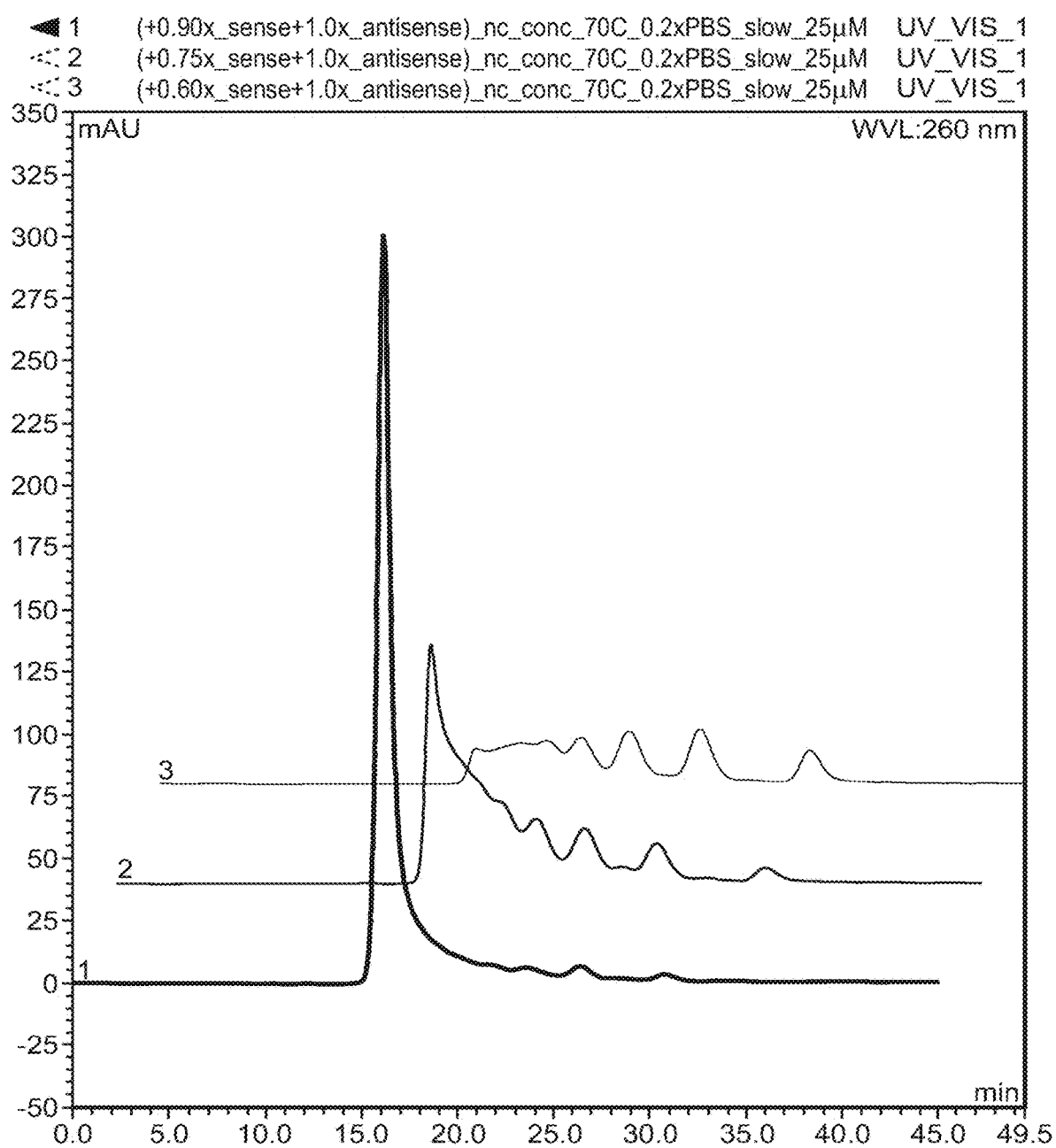
FIG. 33 presents data showing that the smaller the concentration of sense homodimer, the smaller the multimerized siRNA fraction. The data is discussed in connection with Example 22.

In the first of these, the optimized annealing conditions were repeated in the presence of 0.1, 0.3 and 0.9 equivalents of single stranded monomer (lacking any linker) acting as a termination strand. The results, shown in FIG. 32 (below), show that the higher the concentration of termination strand (in this case, the antisense strand was used as the terminator), the smaller the multimerized siRNA fraction.

In the second experiment, the optimized annealing conditions were performed with sub-stoichiometric amounts of the non-cleavable sense homodimer X12712; specifically, 90 mol %, 75 mol % and 60 mol % of the sense homodimer versus 100 mol % of the antisense homodimer X12711 were used in the annealing reaction. The results, shown in FIG.

TABLE 18

Annealing conditions and Results

| Annealing Conditions | Results |
| --- | --- |
| Temperature versus Cooling Rate: 1 × PBS, 250 µM, at 70° C., 80° C. and 90° C. (for 10 min each time point) with subsequent slow cooling to room temperature (2 h) versus quick cooling by placing samples in ice water bath | No significant changes observed. Quick snap cooling does not offer any advantage. No significant benefit from increased temperature. |
| Temperature versus High Salt Concentration: 10 × PBS, 250 µM, at 70° C., 80° C. and 90° C. (for 10 min each time point) with subsequent slow cooling to room temperature (2 h) | Higher salt concentration increases the portion of smaller multimeric siRNA species. |
| Temperature versus Low Salt Concentration: 0.2 × PBS, 250 µM, at 70° C. 80° C. and 90° C. (for 10 min each time point) with subsequent slow cooling to room temperature (2 h) | Lower salt concentration appears to be optimal for the formation of multimeric siRNAs. Again, temperature has less of an impact. |
| Temperature, Diluted Annealing, Baseline Salt: 1 × PBS, 25 µM (1:10), at 70° C., 80° C. and 90° C. (for 10 min each time point) with subsequent slow cooling to room temperature (2 h) | Higher temperatures destroyed the formation of multimeric siRNA |
| Temperature, Diluted Annealing, Higher Salt: 10 × PBS, 25 µM (1:10), at 70° C., 80° C. and 90° C. (for 10 min each time point ) with subsequent slow cooling to room temperature (2 h) | Increasing the salt concentration at least partially restored the formation of multimeric siRNAs at 80° C., but not at 90° C. |
| Temperature, Diluted Annealing, Lower Salt: 0.2 × PBS, 25 µM (1:10), at 70° C., 80° C. and 90° C. (for 10 min each time point) with subsequent slow cooling to room temperature (2 h) | Consistent with what was observed with annealing at 250 µM |

33, show that the smaller the concentration of sense homodimer, the smaller the multimerized siRNA fraction.

Figure 34A:
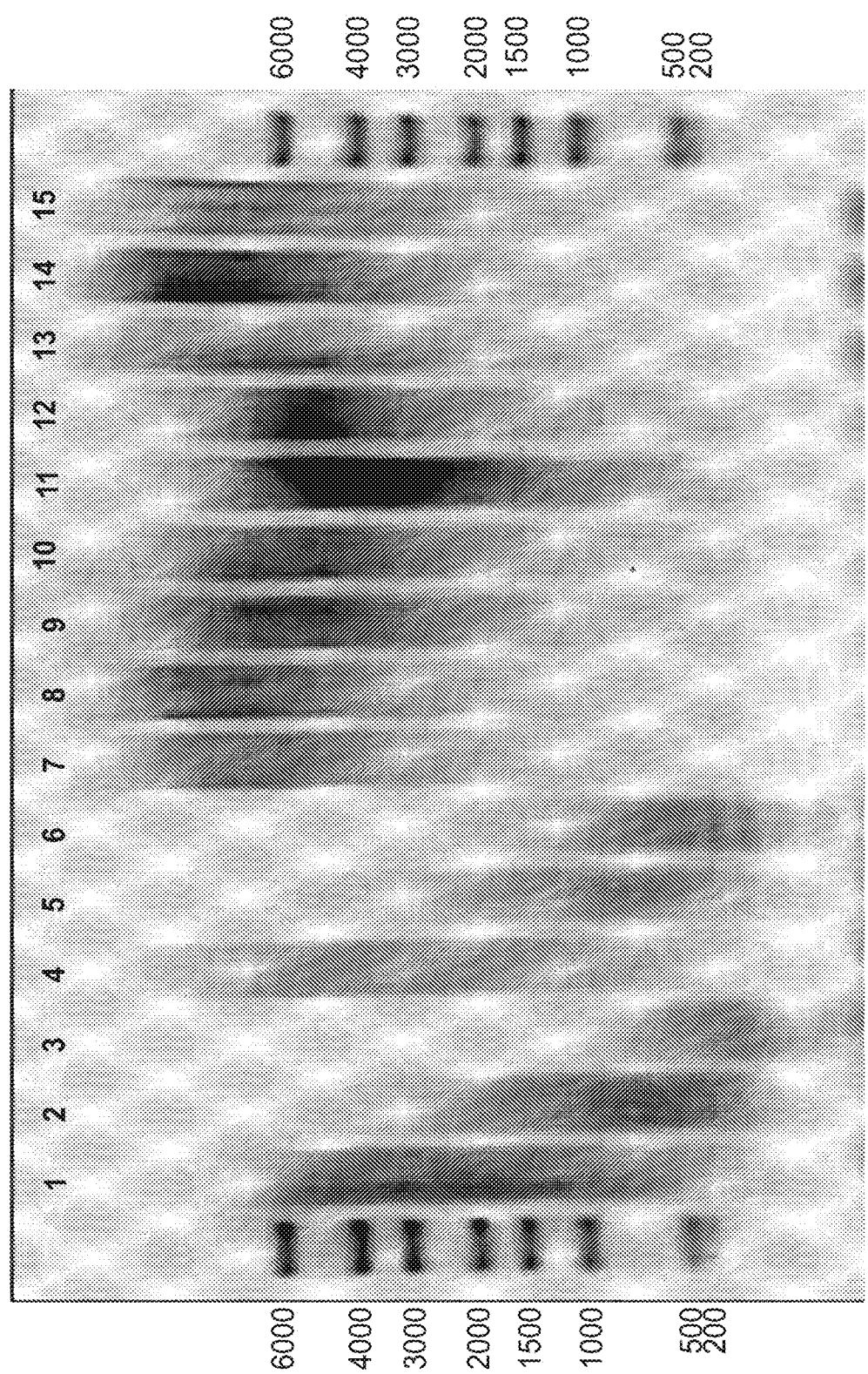
FIG. 34A presents the gel for sample nos. 1-15, which is discussed in connection with Example 22.
Figure 34B:
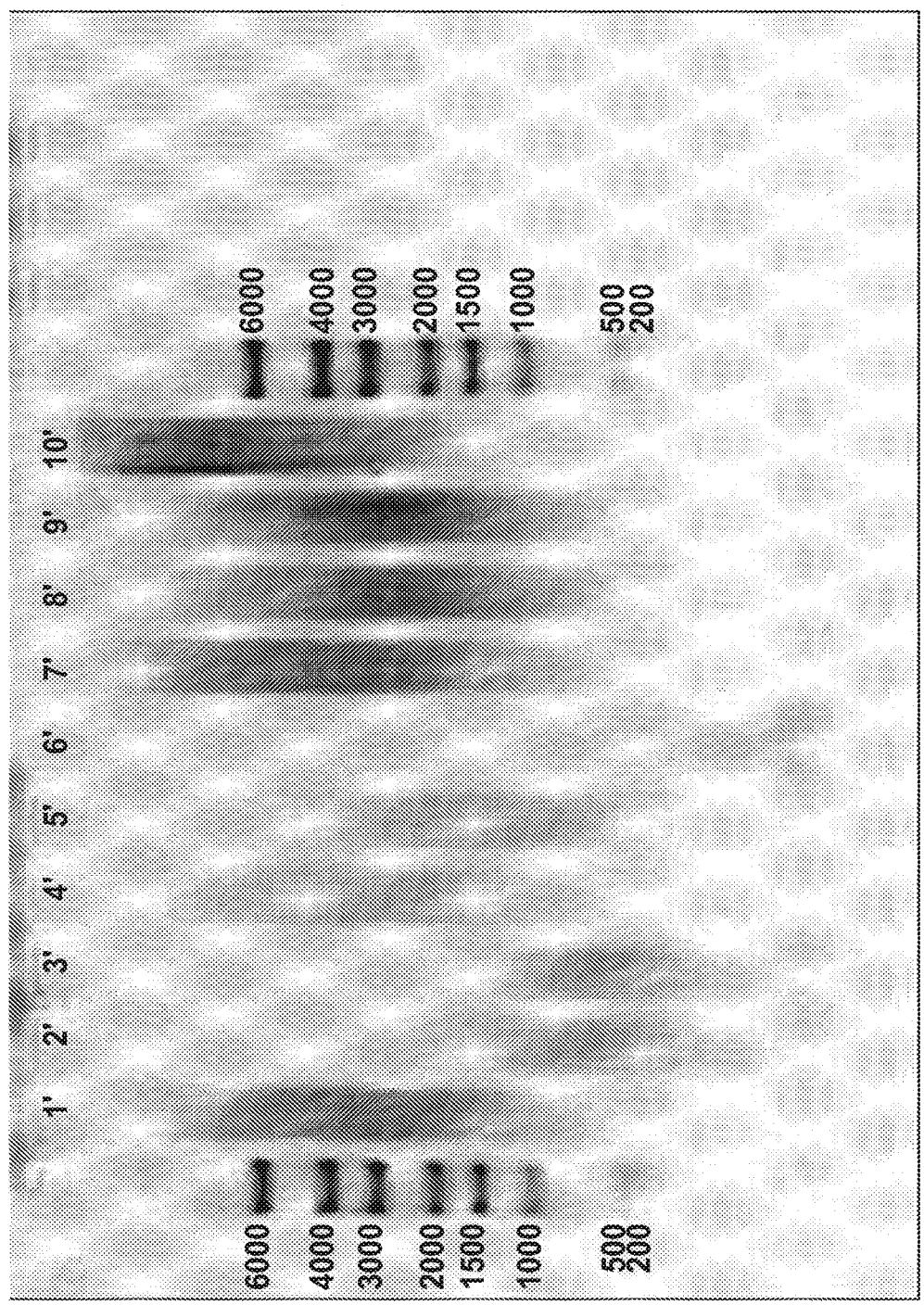
FIG. 34B presents the gel for sample nos. 1'-10', which is discussed in connection with Example 22.

After annealing, the various "terminator" samples and "sub-stoichometric" samples were analyzed on a 2% agarose gel in TAE buffer employing 140 mA for 2 hours. Bands were made visible using GelRed Staining. FIG. 34A represents the gel for sample nos. 1-15. FIG. 34B represents the gel for sample Nos. 1'-10'.

TABLE 19 lists the samples present in the gels and their characteristics:

| Molar Ratios | Reaction Conditions | Sample # |
|---|---|---|
| +0.5x_unlinkered_as | 70 C._250 μM_0.2 × PBS | 1 |
| +1.5x_unlinkered_as | 70 C._250 μM_0.2 × PBS | 2 |
| +4.5x_unlinkered_as | 70 C._250 μM_0.2 × PBS | 3 |
| 4.5_s + 5_as | 70 C._250 μM_0.2 × PBS | 4 |
| 3.75_s + 5_as | 70 C._250 μM_0.2 × PBS | 5 |
| 3.0_s + 5_as | 70 C._250 μM_0.2 × PBS | 6 |
| 5_s + 5_as | 70 C._250 μM_1 × PBS | 7 |
| 5_s + 5_as | 80 C._250 μM_1 × PBS | 8 |
| 5_s + 5_as | 90 C._250 μM_1 × PBS | 9 |
| 5_s + 5_as | 70 C._250 μM_10 × PBS | 10 |
| 5_s + 5_as | 80 C._250 μM_10 × PBS | 11 |
| 5_s + 5_as | 90 C._250 μM_10 × PBS | 12 |
| 5_s + 5_as | 70 C._250 μM_0.2 × PBS | 13 |
| 5_s + 5_as | 80 C._250 μM_0.2 × PBS | 14 |
| 5_s + 5_as | 90 C._250 μM_0.2 × PBS | 15 |
| 5_s + 5_as | 70 C._25 μM_1 × PBS | 1' |
| 5_s + 5_as | 80 C._25 μM_1 × PBS | 2' |
| 5_s + 5_as | 90 C._25 μM_1 × PBS | 3' |
| 5_s + 5_as | 70 C._25 μM_10 × PBS | 4' |
| 5_s + 5_as | 80 C._25 μM_10 × PBS | 5' |
| 5_s + 5_as | 90 C._25 μM_10 × PBS | 6' |
| 5_s + 5_as | 70 C._25 μM_0.2 × PBS | 7' |
| 5_s + 5_as | 80 C._25 μM_0.2 × PBS | 8' |
| 5_s + 5_as | 90 C._25 μM_0.2 × PBS | 9' |
| 5_s + 5_as | 37 C._250 μM_1 × PBS | 10' |

Key: Left-hand column: "+0.5x_unlink_as" means that the sample (#1) was prepared with 10% excess unlinked antisense strand X00549 (as terminator); "+1.5x_unlinkered_as" means that the sample (#2) was prepared with 30% excess unlinked antisense strand X00549 (as terminator); "+4.5x_unlinkered_as" means that the sample (#3) was prepared with 90% excess unlinked antisense strand X00549 (as terminator); for the remaining samples #4-10', X_s+Y_as means the sample was prepared with X nmol sense linked homodimer and Y nmol linked antisense homodimer (e.g., Sample #4, was prepared with 4.5 nmol of linked sense homodimer and 5 nmol of linked antisense homodimer). Sequence X00549:5'-GUfAAGACfU-fUfGAGAUfGAUfCfCfdTsdT-3'. Middle column: reaction conditions are provided in terms of temperature (° C.), RNA concentration (μM), and salt concentration (as PBS).

In summary, these experiments demonstrate that analysis of the multimeric siRNA mixtures is challenging due to the large size of the multimerized siRNA units within the mixture. SEC HPLC analysis is well suited to establish a ration of multimerized (up to the 5- or 6-mer) versus dimerized siRNA units, but failed to provide insights with respect to the extent of multimerization in a given sample. Native agarose gel helps to visualize the extent of multimerization. Further, annealing conditions have a profound influence on the extent of multimerization in the final mixture. For example, when equimolar annealings are performed, very high molecular weight multimeric siRNA formations can be observed (e.g., more than 6000 bp equivalents). Generally, annealing should be performed at high RNA concentrations (≥250 μM), low salt concentrations (e.g., ~0.2×PBS) and reaction temperatures around 70-80° C. The extent of multimerization can be reduced by performing non-equimolar annealings. Multimerizations concentrated in the range of 200-500 DNA bp equivalent (e.g., gel lanes 3 and 6 in FIG. 34A) can be made either by the addition of a terminator single strand or by reducing the amount of one strand significantly.

The samples from gel lane 6 in FIG. 34A and gel lane 10' in FIG. 34B were selected for testing in mice after formulation into LNPs. Sample #10' had an RNA concentration of 250 μM consisting of equal parts sense homodimer and antisense homodimer, and was annealed for 1 hour at 37° C. in 1×PBS. Sample #6, at an RNA concentration of 250 μM consisting of a molar ratio of 3 (sense homodimer) to 5 (antisense homodimer) and 0.2× PBS, was placed into a water bath at 70° C. and cooled down over a period of 3 hours. The resulting multimeric siRNA mixtures were formulated into LNPs according to General Procedure: Lipid Nanoparticle Formulation and analyzed according to General Procedure: LNP Characterization. The compositions and analytical data for the LNP experiment are presented in Tables 20, 21 and 22.

TABLE 20

| Formulation ID | sRNA | Formulation composition mole % | Size (no) | PDI | Zeta (ov) | Conc (mg/ml) | % |
|---|---|---|---|---|---|---|---|
| NPA-624-1 | FVII (XD-00030) | KL22/DSPC/Cholesterol/PEG-c-DOMG 50:10:38.5:1.5 | 69.73 | 0.05 | −0.4 | 0.71 | 63% |
| NPA-194-3 | FVII (XD-00030) | KL52/DSPC/Cholesterol/PEG-c-DOMG 50:10:38.5:1.5 | 91.02 | 0.07 | −2.6 | 0.51 | 83% |
| NPA-625-1 | Multimer lane 6 (XD-05305) (X12712K1 + X12713K1) | KL52/DOPE/Cholesterol/PEG-c-DOMG 40:10:48.5:1.5 | 113.2 | 0.10 | −4.4 | 0.11 | 76% |
| NPA-626-1 | Multimer lane 6 (XD-05305) (X12712K1 + X12713K1) | KL52/DOPE/Cholesterol/PEG-c-DOMG 40:30:28.5:1.5 | 106.2 | 0.05 | −4.6 | 0.14 | 75% |
| NPA-627-1 | Multimer cleavable (XD-05306) (X12710K1 + X12711K1) | KL52/DOPE/Cholesterol/PEG-c-DOMG 40:10:48.5:1.5 | 129.6 | 0.10 | 0.0 | 0.13 | 92% |

TABLE 20-continued

| Formulation ID | sRNA | Formulation composition mole % | Size (no) | PDI | Zeta (ov) | Conc (mg/ml) | % |
|---|---|---|---|---|---|---|---|
| NPA-628-1 | Multimer cleavable (XD-05306) (X12710K1 + X12711K1) | KL52/DOPE/Cholesterol/ PEG-c-DOMG 40:15:43.5:1.5 | 116.4 | 0.07 | −5.3 | 0.14 | 89% |
| NPA-629-2 | Multimer cleavable (XD-05306) (X12710K1 + X12711K1) | KL52/DOPE/Cholesterol/ PEG-c-DOMG 40:20:38.5:1.5 | 142.2 | 0.09 | −6.7 | 0.15 | 99% |
| NPA-630-1 | Multimer cleavable (XD-05306) (X12710K1 + X12711K1) | KL52/DOPE/Cholesterol/ PEG-c-DOMG 40:25:33.5:1.5 | 118.9 | 0.04 | −5.6 | 0.15 | 86% |
| NPA-631-1 | Multimer cleavable (XD-05306) (X12710K1 + X12711K1) | KL52/DOPE/Cholesterol/ PEG-c-DOMG 40:30:28.5:1.5 | 102.8 | 0.03 | −3.7 | 0.16 | 90% |
| NPA-632-1 | Multimer cleavable (XD-05306) (X12710K1 + X12711K1) | KL52/DOPE/Cholesterol/ PEG-c-DOMG 40:40:18.5:1.5 | 90.88 | 0.06 | −1.8 | .016 | 83% |
| NPA-623-2 | Multimer lane 6 (XD-05305) (X12712K1 + X12713K1) | KL52/DOPE/Cholesterol/ PEG-c-DOMG 40:20:38.5:1.5 | 129.1 | 0.06 | −4.9 | .015 | 95% |

TABLE 21

| Formulation ID | sRNA | Formulation composition mole % | Size (no) | PDI | Zeta (ov) | Conc (mg/ml) | % |
|---|---|---|---|---|---|---|---|
| NPA-642-1 | Multimer cleavable lane 6 (XD-05306) (X12710K1 + X12711K1) | KL22/DOPE/Cholesterol/ PEG-c-DOMG 40:20:38.5:1.5 | 62.45 | 0.07 | −2.4 | 0.19 | 93% |
| NPA-643-1 | Multimer cleavable lane 10' (XD-05306) (X12710K1 + X12711K1) | KL22/DOPE/Cholesterol/ PEG-c-DOMG 40:20:38.5:1.5 | 61.67 | 0.08 | −2.5 | .019 | 92% |
| NPA-644-1 | Multimer cleavable lane 6 (XD-05306) (X12710K1 + X12711K1) | Invivofectamine 2.0 | 69.52 | 0.02 | 1.2 | 0.42 | 97% |
| NPA-645-1 | Multimer cleavable lane 10' (XD-05306) (X12710K1 + X12711K1) | Invivofectamine 2.0 | 87.71 | 0.11 | 1.2 | 0.44 | 100% |
| NPA-646-1 | FVII (XD-00376) | Invivofectamine 2.0 | 67.04 | 0.07 | 2.2 | 0.46 | 100% |

TABLE 22

Defined-length Dimeric (2-mer) siRNA Duplexes. Defined dimeric siRNA:

| Duplex-ID | Description | sRNA ID | Sequence (5'-3') |
|---|---|---|---|
| XD-04600 | F (s-c-s) | X12710 | GGAUfCfAUfCfUfCfAAGUfCfUfUfACfdTsdT(SHC6)(DTME) GGAUfCfAUfCfUfCfAAGUfCfUfUfACfdTsdT(SHC6) |
| | | X00549 | GUfAAGACfUfUfGAGAUfGAUfCfCfdTsdT |
| XD-04601 | H (s-nc-s) | X12712 | GGAUfCfAUfCfUfCfAAGUfCfUfUfACfdTsdT(SHC6)(BMPEG2) GGAUfCfAUfCfUfCfAAGUfCfUfUfACfdTsdT(SHC6) |
| | B | X00549 | GUfAAGACfUfUfGAGAUfGAUfCfCfdTsdT |

Example 23: Analysis of LNP-Formulated Mixtures of FVII Multimeric siRNA (Animal Experiment MausRNAi-TV29130)

Figure 35:
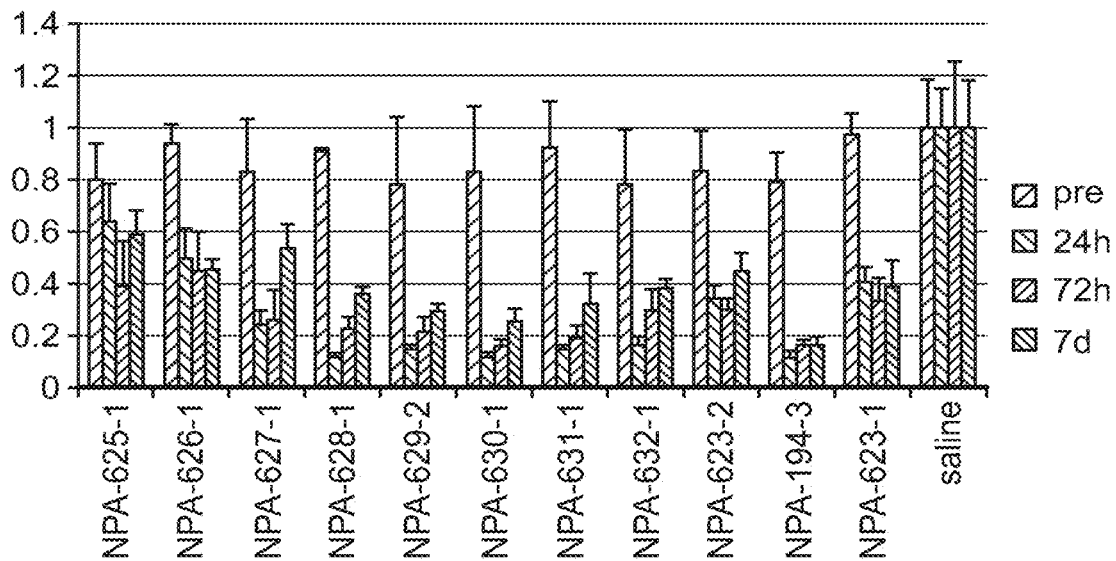
FIG. 35 presents data showing FVII activity determined from mouse serum in animal experiment MausRNAi-TV29, which is discussed in connection with Example 23.
Figure 36:
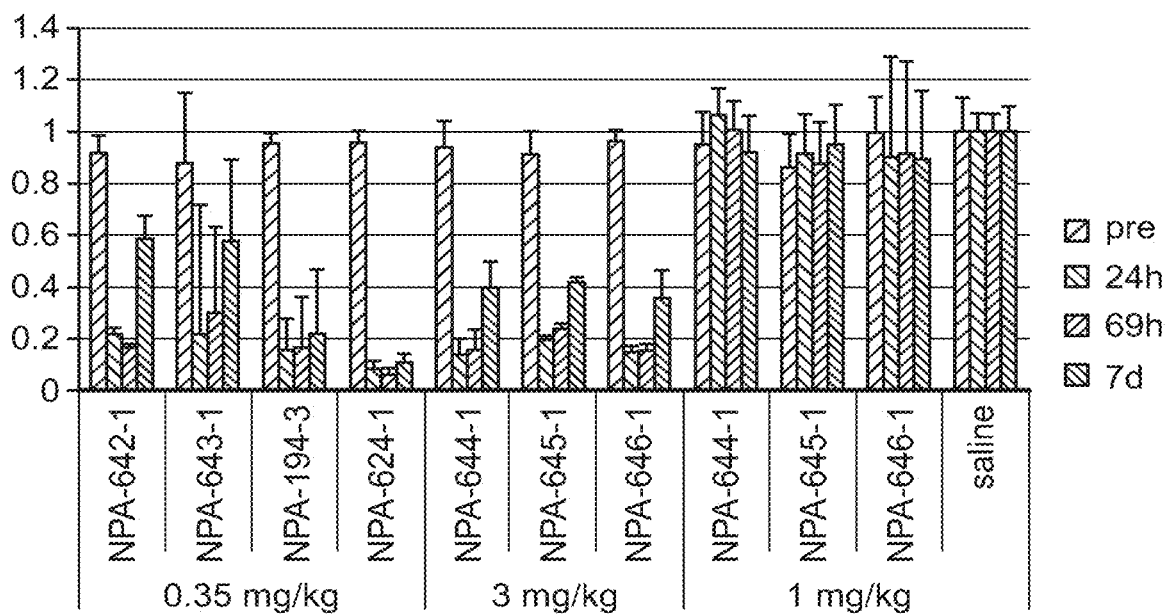
FIG. 36 presents data showing FVII activity determined from mouse serum in animal experiment MausRNAi-TV30, which is discussed in connection with Example 23.

To determine the in vivo efficacy of mixtures of multimeric siRNAs (targeted to FVII) formulated in LNPs of different lipid composition (listed in Table 23), an animal experiment was performed as described above (General Procedure: Animal Experiments). Compounds were injected intravenously at a dose of 0.35 mg/kg siRNA. Multimeric siRNAs formulated with Invivofectamine 2.0 were injected at a dose of 1 mg/kg and 3 mg/kg. LNP-formulated canonical FVII siRNA (XD-00030) was included as positive control. Group size was n=3 mice for treatment groups and n=6 for saline controls. Blood was collected at the time points noted in the graphs below and analyzed for FVII enzyme activity. Results are shown in FIG. 35.

TABLE 23

LNP-formulations used for animal experiment MausRNAi-TV29

| Formulation-ID | lipids | siRNA |
|---|---|---|
| NPA-625-1 | XL10 DOPE 10 | Multimer lane 6 (XD-05305) (X12712K1 + X12713K1) |
| NPA-626-1 | XL10 DOPE 30 | Multimer lane 6 (XD-05305) (X12712K1 + X12713K1) |
| NPA-627-1 | XL10 DOPE 10 | Multimer cleavable (XD-05306) (X12710K1 + X12711K1) |
| NPA-628-1 | XL10 DOPE 15 | Multimer cleavable (XD-05306) (X12710K1 + X12711K1) |
| NPA-630-1 | XL10 DOPE 25 | Multimer cleavable (XD-05306) (X12710K1 + X12711K1) |
| NPA-631-1 | XL10 DOPE 30 | Multimer cleavable (XD-05306) (X12710K1 + X12711K1) |
| NPA-632-1 | XL10 DOPE 40 | Multimer cleavable (XD-05306) (X12710K1 + X12711K1) |
| NPA-623-2 | XL10 DOPE 20 | Multimer lane 6 (XD-05305) (X12712K1 + X12713K1) |
| NPA-629-2 | XL10 DOPE 20 | Multimer cleavable (XD-05306) (X12710K1 + X12711K1) |
| NPA-194-3 | XL10 std | XD-00030 (FVII monomer) |
| NPA-624-1 | XL7 std | XD-00030 (FVII monomer) |

When comparing different payloads (payloads having cleavable vs. noncleavable linkers) in the same formulations, we observe that the cleavable payloads performed better than the non-cleavable payloads (e.g., NPA-625-1 vs. NPA-62701; NPA-626-1 vs. NPA-631-1; and NPA-629-1 vs. NPA-623).

TABLE 24

LNP-formulations used in animal experiment MausRNAi-TV30

| Formulation-ID | siRNA | lipids |
|---|---|---|
| NPA-642-1 | Multimer cleavable lane 6 (XD-05306) (X12710K1 + X12711K1) | XL DOPE 20 |
| NPA-643-1 | Multimer cleavable lane 10' (XD-05306) (X12710K1 + X12711K1) | XL DOPE 20 |
| NPA-644-1 | Multimer cleavable lane 6 (XD-05306) (X12710K1 + X12711K1) | Invivofectamine 2.0 |
| NPA-645-1 | Multimer cleavable lane 10' (XD-05306) (X12710K1 + X12711K1) | Invivofectamine 2.0 |
| NPA-646-1 | FVII (XD-00376) | Invivofectamine 2.0 |

Example 24: Manufacture of FVII HeteroDimer of FVIIsense: FVIIantisense (X12714) and Resulting Mixture of Multimers (XD-05312)

A variation on the F7-ApoB heterodimer of Example 9 was made from chemically linking siF7 sense strand to siF7 antisense strand to form a single-stranded heterodimer targeting F7, as depicted in FIG. 37.

Heterodimer X12714 appears in lane 12 in the gel depicted in FIG. 38. Gel analysis conditions were: 1.5 µg/lane; 2% agarose gel in 1×TAE; 140 mA; 130 min; Gel red staining (1:10000).

Example 25: Sequence Selection for ApoB Screen

No suitable siRNA against Murine ApoB was known before the present invention. Accordingly, dsRNA design was carried out to identify specific dsRNAs targeting mouse ApoB. First, known mRNA sequences of mouse (*Mus musculus*) ApoB (NM_009693.2 listed as SEQ ID NO:62 and XM_006515078.1 listed as SEQ ID NO:63 were downloaded from NCBI Reference Sequence database, release 73).

From this initial set of sequences those harbouring a SNP (single nucleotide polymorphism) in their corresponding target site sequence (positions 2-18 of 19mer) in mouse ApoB mRNA (SEQ ID NO. 64) as indicated by the NCBI dbSNP (build 146) were excluded.

In identifying RNAi agents, the selection was limited to 19mer sense and antisense sequences, having at least 1 or 2 mismatches, respectively, to any other sequence in the mouse NCBI Ref Seq database (release 73), which we assumed to represent the comprehensive mouse transcriptome.

Selection of candidates was further limited by elimination of 19mer sense and antisense strands harbouring seed sequences (nucleotides 2-7 of the 5' terminus) identical to known mouse miRNA seed sequences (nucleotides 2-7 of the 5' terminus) as listed in miRBase (University of Manchester, release 21).

In addition, all sense and antisense sequences containing five or more consecutive G's (poly-G sequences) were excluded from the selection. The sequences identified are presented in Table 25.

TABLE 25

Core sequences of double stranded RNAs (dsRNAs) targeting mouse ApoB mRNA.

| SEQ ID NO | Sense strand core sequence (5'-3') | SEQ ID NO | Antisense strand core sequence (5'-3') |
|---|---|---|---|
| 65 | CAACCAGUGUACCCUUAAA | 77 | UUUAAGGGUACACUGGUUG |
| 66 | CUGUGUACGAAGUACAAAA | 78 | UUUUGUACUUCGUACACAG |

TABLE 25-continued

Core sequences of double stranded RNAs (dsRNAs) targeting mouse ApoB mRNA.

| SEQ ID NO | Sense strand core sequence (5'-3') | SEQ ID NO | Antisense strand core sequence (5'-3') |
|---|---|---|---|
| 67 | CAACCUAUGAACUCCUAAA | 79 | UUUAGGAGUUCAUAGGUUG |
| 68 | GCUUACGGCUCAACAAUUU | 80 | AAAUUGUUGAGCCGUAAGC |
| 69 | GCACGUGAUGGACUAUCAA | 81 | UUGAUAGUCCAUCACGUGC |
| 70 | CUAUUUGGAGAGAAAUCGA | 82 | UCGAUUUCUCUCCAAAUAG |
| 71 | GAGAUUAUUGAUCGAAUCA | 83 | UGAUUCGAUCAAUAAUCUC |
| 72 | CCGUGUAAAUCUAGCAAAA | 84 | UUUUGCUAGAUUUACACGG |
| 73 | GCAUUUAGAUCAAUUGAGA | 85 | UCUCAAUUGAUCUAAAUGC |
| 74 | GGUUUUAAUGGAUAAAUCA | 86 | UGAUUUAUCCAUUAAAACC |
| 75 | GACUUUGCAGAGCAAUAUU | 87 | AAUAUUGCUCUGCAAAGUC |
| 76 | CUUACGGGUCAUCCAAAAA | 88 | UUUUUGGAUGACCCGUAAG |

The selected sequences from Table 25 were synthesized with chemical modifications as presented in Table 26A and 26B.

TABLE 26A

| SEQ ID | Duplex-ID | SEQ ID | ss-ID | Sequence (5'-3') |
|---|---|---|---|---|
| 91 | XD-05962 | 89 | X18815 | caAfcCfaGfuGfuAfcCfcUfuAfaAfdTsdT |
| 94 | XD-05963 | 92 | X18817 | cuGfuGfuAfcGfaAfgUfaCfaAfaAfdTsdT |
| 97 | XD-05964 | 95 | X18819 | caAfcCfuAfuGfaAfcUfcCfuAfaAfdTsdT |
| 100 | XD-05965 | 98 | X18821 | gcUfuAfcGfgCfuCfaAfcAfaUfuUfdTsdT |
| 103 | XD-05966 | 101 | X18823 | gcAfcGfuGfaUfgGfaCfuAfuCfaAfdTsdT |
| 106 | XD-05967 | 104 | X18825 | cuAfuUfuGfgAfgAfgAfaAfuCfgAfdTsdT |
| 109 | XD-05968 | 107 | X18827 | gaGfaUfuAfuUfgAfuCfgAfaUfcAfdTsdT |
| 112 | XD-05969 | 110 | X18829 | ccGfuGfuAfaAfuCfuAfgCfaAfaAfdTsdT |
| 115 | XD-05970 | 113 | X18831 | gcAfuUfuAfgAfuCfaAfuUfgAfgAfdTsdT |
| 118 | XD-05971 | 116 | X18833 | ggUfuUfuAfaUfgGfaUfaAfaUfcAfdTsdT |
| 121 | XD-05972 | 119 | X18835 | gaCfuUfuGfcAfgAfgCfaAfuAfuUfdTsdT |
| 124 | XD-05973 | 122 | X18837 | cuUfaCfgGfgUfcAfuCfcAfaAfaAfdTsdT |

TABLE 26B

| SEQ ID | Duplex-ID | SEQ ID | as-ID | Sequence (5'-3') |
|---|---|---|---|---|
| 91 | XD-05962 | 90 | X18816 | UfUfuAfaGfgGfuAfcAfcUfgGfuUfgdTsdT |
| 94 | XD-05963 | 93 | X18818 | UfUfuUfgUfaCfuUfcGfuAfcAfcAfgdTsdT |
| 97 | XD-05964 | 96 | X18820 | UfUfaGfgAfgUfuCfaUfaGfgUfuGfdTsdT |
| 100 | XD-05965 | 99 | X18822 | AfAfaUfuGfuUfgAfgCfcGfuAfaGfcdTsdT |
| 103 | XD-05966 | 102 | X18824 | UfUfgAfuAfgUfcCfaUfcAfcGfuGfcdTsdT |
| 106 | XD-05967 | 105 | X18826 | UfCfgAfuUfuCfuCfuCfcAfaAfuAfgdTsdT |

TABLE 26B-continued

| SEQ ID | Duplex-ID | SEQ ID | as-ID | Sequence (5'-3') |
|---|---|---|---|---|
| 109 | XD-05968 | 108 | X18828 | UfGfaUfuCfgAfuCfaAfuAfaUfcUfcdTsdT |
| 112 | XD-05969 | 111 | X18830 | UfUfuUfgCfuAfgAfuUfuAfcAfcGfgdTsdT |
| 115 | XD-05970 | 114 | X18832 | UfCfuCfaAfuUfgAfuCfuAfaAfuGfcdTsdT |
| 118 | XD-05971 | 117 | X18834 | UfGfaUfuUfaUfcCfaUfuAfaAfaCfcdTsdT |
| 121 | XD-05972 | 120 | X18836 | AfAfuAfuUfgCfuCfuGfcAfaAfgUfcdTsdT |
| 124 | XD-05973 | 123 | X18838 | UfUfuUfuGfgAfuGfaCfcCfgUfaAfgdTsdT | wherein lower case letters "c", "g", "a" and "u" represent 2'-O-methylmodified nucleotides, "s" represents phosphorothioate and "dT" represents deoxythymidine residues. Upper case letters A, C, G, U followed by "f" indicate 2'-fluoro nucleotides. The modified dsRNAs presented in Tables 26A and 26B correspond to the unmodified dsRNAs presented in Table 25, as follows: SEQ ID NO:89-124 are the modified sequences corresponding to the unmodified sequences presented as SEQ ID NO:65-88.

Example 26: In Vitro Evaluation of siRNAs Targeting ApoB

The activity of the siRNAs in Table X directed against mouse ApoB mRNA was tested in the murine liver cell line NMuLi.

ApoB mRNA content was quantified by branched DNA in total mRNA isolated from cells incubated with ApoB specific siRNAs. Cells were obtained from American Type Culture Collection (Rockville, Md., Cat. No. CCL-1638). NMuLi cells were cultured in Dulbeccos modified Eagle's medium (DMEM, Biochrom #F0435) supplemented with 10% fetal calf serum (FCS, Biochrom AG, Berlin, Germany, cat. No. 50115) and Penicillin 100 U/ml, Streptomycin 100 mg/ml (Biochrom AG, Berlin, Germany, Cat. No. A2213).

Figure 39:
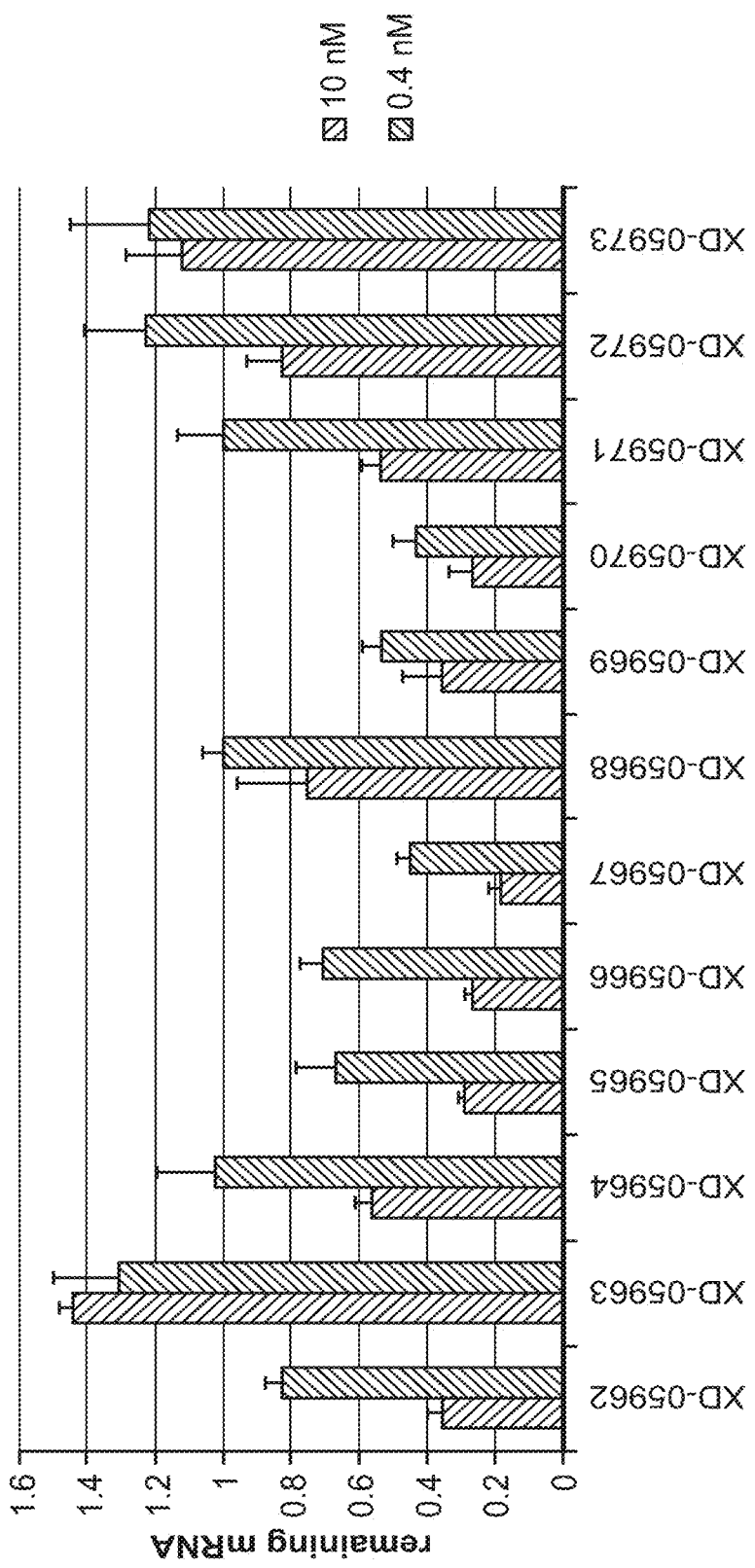
FIG. 39 presents dose-response data for ApoB screening NMuLi cells, which is discussed in connection with Example 26.

Transfection of siRNAs was performed directly after seeding 15,000 NMuLi cells/well on a 96-well plate, and was carried out with the transfection reagent RNAiMax (Invitrogen GmbH, Karlsruhe, Germany, Cat. No. 13778-150) as described by the manufacturer. In a dose response experiment performed in quadruplicates, siRNA concentrations started at 50 nM and decreased in 5-fold dilution steps down to 16 pM. After transfection cells were incubated for 24 h at 37° C. and 5% $CO_2$ in a humidified incubator (Heraeus GmbH, Hanau, Germany). Transfection reagent only ("mock")-treated cells served as negative control. ApoB mRNA levels were quantified using a Quantigene Explore Kit QG1.0 (Panomics, Fremont, Calif., USA, cat. No. QG0004). Cells were harvested and lysed at 53° C. following procedures recommended by the manufacturer. After incubation and lysis, cell lysates were incubated with probe-sets specific to mouse ApoB and mouse GAPDH (as housekeeper for normalization). Assays were processed according to the manufacturer's protocol. Chemoluminescence was measured in a Victor2-Light (Perkin Elmer, Wiesbaden, Germany) as RLUs (relative light units) and values obtained with the ApoB probe-set were normalized to the respective GAPDH values for each well. For graphical representation, ApoB mRNA levels at 10 nM and 0.4 nM are shown relative to the levels of mock-treated cells set as 1 (FIG. 39). $IC_{50}$ (target mRNA reduced by 50%) and $IC_{80}$ (target mRNA reduced by 80%) values were determined using the XLfit software (IDBS, Guildford, UK) and are shown in Table 27. The siRNA XD-05967 was chosen as best candidate for the multimer experiments as it had the lowest $IC_{80}$ value, and XD-05970 as backup candidate due to the best $IC_{50}$ value.

TABLE 27

IC50 and IC80 values of ApoB targeted siRNAs

| siRNA | IC50 (nM) | IC80 (nM) |
|---|---|---|
| XD-05962 | 1.77 | n.a. |
| XD-05963 | n.a. | n.a. |
| XD-05964 | n.a. | n.a. |
| XD-05965 | 1.34 | n.a. |
| XD-05966 | 1.84 | n.a. |
| XD-05967 | 0.29 | 9.12 |
| XD-05968 | n.a. | n.a. |
| XD-05969 | 0.54 | n.a. |
| XD-05970 | 0.17 | 44.63 |
| XD-05971 | n.a. | n.a. |
| XD-05972 | n.a. | n.a. |
| XD-05973 | n.a. | n.a. |

What is claimed is:

1. An isolated compound according to one of the following structures:

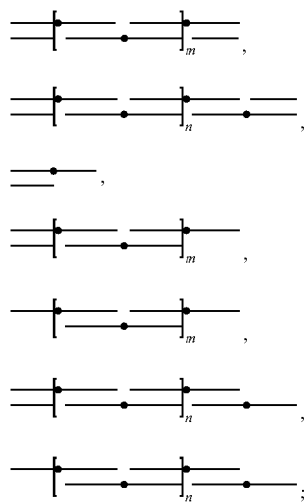

wherein:
- each ═══ is a double stranded oligonucleotide having 15-30 nucleotides in length;
- each ──── is a single stranded oligonucleotide having 15-30 nucleotides in length;
- each • is a covalent linker joining single strands of adjacent oligonucleotides; and
- m is 1, 2, or 3 and n is 0, 1, 2, or 3.

2. The isolated compound of claim 1, wherein each covalent linker • is the same.

3. The isolated compound of claim 1, wherein the compound comprises two or more different covalent linkers •.

4. The isolated compound of claim 1, comprising a homo-multimer of substantially identical double stranded oligonucleotides.

5. The isolated compound of claim 4, wherein the substantially identical double stranded oligonucleotides each comprise an siRNA targeting the same molecular target in vivo.

6. The isolated compound of claim 1, comprising heteromultimer of two or more substantially different double stranded oligonucleotides ═══.

7. The isolated compound of claim 1, wherein at least one of the double stranded oligonucleotides ═══ comprise an siRNA.

8. The isolated compound of claim 1, wherein the compound further comprises a targeting ligand.

9. The isolated compound of claim 1, wherein the covalent linker • comprises a cleavable covalent linker.

10. The isolated compound of claim 9, wherein the cleavable covalent linker comprises: an acid cleavable ester bond, hydrazine bond, acetal bond, a reductant cleavable bond, a biocleavable bond, or an enzyme cleavable bond.

11. The isolated compound of claim 10, wherein the reductant cleavable bond is a disulfide bond.

12. The isolated compound of claim 1, wherein the covalent linkers • comprise a reaction product of a nucleophile and electrophile.

13. The isolated compound of claim 1, wherein the covalent linkers • individually comprise a reaction product of (i) a thiol and a maleimide, and optionally wherein the reaction product of the thiol and maleimide is a derivative of succinamic acid, (ii) a thiol and a vinylsulfone, (iii) a thiol and a pyridyldisulfide, (iv) a thiol and an iodoacetamide, (v) a thiol and an acrylate, (vi) an azide and an alkyne, or (vii) an amine and a carboxyl group.

14. The isolated compound of claim 1, wherein the covalent linkers • individually comprise DTME (dithiobismaleimidoethane), BM(PEG)2 (1,8-bis(maleimido)diethylene glycol), BM(PEG)3 (1,11-bismaleimidotriethyleneglycol), BMOE (bismaleimidoethane), BMH (bismaleimidohexane), BMB (1,4-bismaleimidobutane), or a succinamic acid derivative of any of the foregoing.

15. The isolated compound of claim 1, wherein the compound is greater than or equal to 75% pure.

16. The isolated compound of claim 1, wherein the compound is greater than or equal to 85% pure.

17. The isolated compound of claim 1, wherein the compound is greater than or equal to 95% pure.

18. A method for reducing gene expression comprising administering an effective amount of the isolated compound according claim 1 to a subject in need thereof.

* * * * *

SEQUENCE LISTING

<160> NUMBER OF SEQ ID NOS: 164

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1
gcaaaggcgu gccaacucat                                                    20

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 2
gcaaaggcgu gccaacucat                                                    20

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 3
gcaaaggcgu gccaacucat                                                    20

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 4
gcaaaggcgu gccaacucat                                                    20

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 5
gcaaaggcgu gccaacucat                                                    20

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

```
<220> FEATURE:
<223> OTHER INFORMATION: Description of Combined DNA/RNA Molecule:
      Synthetic oligonucleotide

<400> SEQUENCE: 6
gcaaaggcgu gccaacucat                                                    20

<210> SEQ ID NO 7
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 7
ugaguuggca cgccuuugcu ut                                                 22

<210> SEQ ID NO 8
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 8
ugaguuggca cgccuuugcu u                                                  21

<210> SEQ ID NO 9
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 9
ugaguuggca cgccuuugcu u                                                  21

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 10
cuauuuggag agaaaucgat                                                    20

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
```

```
<400> SEQUENCE: 11
cuauuuggag agaaaucgat                                          20

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 12
cuauuuggag agaaaucgat                                          20

<210> SEQ ID NO 13
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 13
ggaucaucuc aagucuuact t                                        21

<210> SEQ ID NO 14
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 14
guaagacuug agaugaucct t                                        21

<210> SEQ ID NO 15

<400> SEQUENCE: 15

000

<210> SEQ ID NO 16
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 16
gcaaaggcgu gccaacucat t                                        21

<210> SEQ ID NO 17
<211> LENGTH: 21
```

```
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 17
ugaguuggca cgccuuugct t                                              21

<210> SEQ ID NO 18

<400> SEQUENCE: 18

000

<210> SEQ ID NO 19
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 19
ggaaucuuau auuugaucca a                                              21

<210> SEQ ID NO 20
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 20
uuggaucaaa uauaagauuc ccu                                            23

<210> SEQ ID NO 21

<400> SEQUENCE: 21

000

<210> SEQ ID NO 22
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 22
cuuacgcuga guacuucgat t                                              21

<210> SEQ ID NO 23
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
```

```
<220> FEATURE:
<223> OTHER INFORMATION: Description of Combined DNA/RNA Molecule:
      Synthetic oligonucleotide

<400> SEQUENCE: 23
ucgaaguacu cagcguaagt t                                              21

<210> SEQ ID NO 24

<400> SEQUENCE: 24

000

<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 25
gcaaaggcgu gccaacucat                                                20

<210> SEQ ID NO 26
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 26
ugaguuggca cgccuuugcu u                                              21

<210> SEQ ID NO 27

<400> SEQUENCE: 27

000

<210> SEQ ID NO 28
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 28
cuauuuggag agaaaucgat                                                20

<210> SEQ ID NO 29
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 29
ucgauuucuc uccaaauagu u                                              21
```

<210> SEQ ID NO 30

<400> SEQUENCE: 30

000

<210> SEQ ID NO 31
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 31
aacaguguuc uugcucuaua at                                              22

<210> SEQ ID NO 32
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 32
uuauagagca agaacacugu uuu                                             23

<210> SEQ ID NO 33

<400> SEQUENCE: 33

000

<210> SEQ ID NO 34
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 34
gcaaaggcgu gccaacucat                                                 20

<210> SEQ ID NO 35
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 35
gcaaaggcgu gccaacucat                                                 20

<210> SEQ ID NO 36

```
<400> SEQUENCE: 36

000

<210> SEQ ID NO 37
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 37
ggaaucuuau auuugaucca a                                            21

<210> SEQ ID NO 38
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 38
ggaucaucuc aagucuuact t                                            21

<210> SEQ ID NO 39
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 39
gcaaaggcgu gccaacucat                                              20

<210> SEQ ID NO 40
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 40
ugaguuggca cgccuuugcu u                                            21

<210> SEQ ID NO 41
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 41
gcaaaggcgu gccaacucat                                              20
```

-continued

<210> SEQ ID NO 42

<400> SEQUENCE: 42

000

<210> SEQ ID NO 43

<400> SEQUENCE: 43

000

<210> SEQ ID NO 44
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 44
uuauagagca agaacacugu uuu                                              23

<210> SEQ ID NO 45
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 45
aacaguguuc uugcucuaua at                                               22

<210> SEQ ID NO 46
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 46
gcaaaggcgu gccaacucat                                                  20

<210> SEQ ID NO 47
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 47
uuauagagca agaacacugu uuu                                              23

<210> SEQ ID NO 48
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

```
<220> FEATURE:
<223> OTHER INFORMATION: Description of Combined DNA/RNA Molecule:
      Synthetic oligonucleotide

<400> SEQUENCE: 48
aacaguguuc uugcucuaua at                                                  22

<210> SEQ ID NO 49

<400> SEQUENCE: 49

000

<210> SEQ ID NO 50

<400> SEQUENCE: 50

000

<210> SEQ ID NO 51

<400> SEQUENCE: 51

000

<210> SEQ ID NO 52
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 52
gcaaaggcgu gccaacucat                                                     20

<210> SEQ ID NO 53

<400> SEQUENCE: 53

000

<210> SEQ ID NO 54

<400> SEQUENCE: 54

000

<210> SEQ ID NO 55

<400> SEQUENCE: 55

000

<210> SEQ ID NO 56
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
```

-continued

```
<400> SEQUENCE: 56
ggaucaucuc aagucuuact t                                              21

<210> SEQ ID NO 57
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 57
guaagacuug agaugaucct t                                              21

<210> SEQ ID NO 58
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 58
ggaucaucuc aagucuuact t                                              21

<210> SEQ ID NO 59
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 59
guaagacuug agaugauccct t                                             21

<210> SEQ ID NO 60
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 60
ggaucaucuc aagucuuact t                                              21

<210> SEQ ID NO 61
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
```

```
<220> FEATURE:
<223> OTHER INFORMATION: Description of Combined DNA/RNA Molecule:
      Synthetic oligonucleotide

<400> SEQUENCE: 61
guaagacuug agaugaucct t                                             21

<210> SEQ ID NO 62

<400> SEQUENCE: 62

000

<210> SEQ ID NO 63

<400> SEQUENCE: 63

000

<210> SEQ ID NO 64

<400> SEQUENCE: 64

000

<210> SEQ ID NO 65
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 65
caaccagugu acccuuaaa                                                19

<210> SEQ ID NO 66
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 66
cuguguacga aguacaaaa                                                19

<210> SEQ ID NO 67
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 67
caaccuauga acuccuaaa                                                19

<210> SEQ ID NO 68
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
```

<400> SEQUENCE: 68
gcuuacggcu caacaauuu                                              19

<210> SEQ ID NO 69
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 69
gcacgugaug gacuaucaa                                              19

<210> SEQ ID NO 70
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 70
cuauuuggag agaaaucga                                              19

<210> SEQ ID NO 71
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 71
gagauuauug aucgaauca                                              19

<210> SEQ ID NO 72
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 72
ccguguaaau cuagcaaaa                                              19

<210> SEQ ID NO 73
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 73
gcauuuagau caauugaga                                              19

<210> SEQ ID NO 74
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 74
gguuuuaaug gauaaauca                                                19

<210> SEQ ID NO 75
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 75
gacuuugcag agcaauauu                                                19

<210> SEQ ID NO 76
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 76 cuuacgdgguc auccaaaaa                                               19

<210> SEQ ID NO 77
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 77
uuuaagggua cacugguug                                                19

<210> SEQ ID NO 78
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 78
uuuuguacuu cguacacag                                                19

<210> SEQ ID NO 79
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 79
uuuaggaguu cauagguug                                                19

<210> SEQ ID NO 80
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
```

<400> SEQUENCE: 80
aaauuguuga gccguaagc                                              19

<210> SEQ ID NO 81
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 81
uugauagucc aucacgugc                                              19

<210> SEQ ID NO 82
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 82
ucgauuucuc uccaaauag                                              19

<210> SEQ ID NO 83
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 83
ugauucgauc aauaaucuc                                              19

<210> SEQ ID NO 84
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 84
uuuugcuaga uuuacacgg                                              19

<210> SEQ ID NO 85
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 85
ucucaauuga ucuaaaugc                                              19

<210> SEQ ID NO 86
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 86
ugauuuaucc auuaaaacc                                                19

<210> SEQ ID NO 87
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 87
aauauugcuc ugcaaaguc                                                19

<210> SEQ ID NO 88
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 88
uuuuuggaug acccguaag                                                19

<210> SEQ ID NO 89
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 89
caaccagugu acccuuaaat t                                             21

<210> SEQ ID NO 90
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 90
uuuaagggua cacugguugt t                                             21

<210> SEQ ID NO 91

<400> SEQUENCE: 91

000

<210> SEQ ID NO 92
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
```

```
<220> FEATURE:
<223> OTHER INFORMATION: Description of Combined DNA/RNA Molecule:
      Synthetic oligonucleotide

<400> SEQUENCE: 92
cuguguacga aguacaaaat t                                              21

<210> SEQ ID NO 93
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 93
uuuuguacuu cguacacagt t                                              21

<210> SEQ ID NO 94

<400> SEQUENCE: 94

000

<210> SEQ ID NO 95
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 95
caaccuauga acuccuaaat t                                              21

<210> SEQ ID NO 96
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 96
uuuaggaguu cauagguugt t                                              21

<210> SEQ ID NO 97

<400> SEQUENCE: 97

000

<210> SEQ ID NO 98
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
```

```
<223> OTHER INFORMATION: Description of Combined DNA/RNA Molecule:
      Synthetic oligonucleotide

<400> SEQUENCE: 98
gcuuacggcu caacaauuut t                                              21

<210> SEQ ID NO 99
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 99
aaauuguuga gccguaagct t                                              21

<210> SEQ ID NO 100

<400> SEQUENCE: 100

000

<210> SEQ ID NO 101
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 101
gcacgugaug gacuaucaat t                                              21

<210> SEQ ID NO 102
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 102
uugauagucc aucacgugct t                                              21

<210> SEQ ID NO 103

<400> SEQUENCE: 103

000

<210> SEQ ID NO 104
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
```

```
<220> FEATURE:
<223> OTHER INFORMATION: Description of Combined DNA/RNA Molecule:
      Synthetic oligonucleotide

<400> SEQUENCE: 104
cuauuuggag agaaaucgat t                                             21

<210> SEQ ID NO 105
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 105
ucgauuucuc uccaaauagt t                                             21

<210> SEQ ID NO 106

<400> SEQUENCE: 106

000

<210> SEQ ID NO 107
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 107
gagauuauug aucgaaucat t                                             21

<210> SEQ ID NO 108
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 108
ugauucgauc aauaaucuct t                                             21

<210> SEQ ID NO 109

<400> SEQUENCE: 109

000

<210> SEQ ID NO 110
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
```

```
<223> OTHER INFORMATION: Description of Combined DNA/RNA Molecule:
      Synthetic oligonucleotide

<400> SEQUENCE: 110
ccguguaaau cuagcaaaat t                                              21

<210> SEQ ID NO 111
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 111
uuuugcuaga uuuacacggt t                                              21

<210> SEQ ID NO 112

<400> SEQUENCE: 112

000

<210> SEQ ID NO 113
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 113
gcauuuagau caauugagat t                                              21

<210> SEQ ID NO 114
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 114
ucucaauuga ucuaaaugct t                                              21

<210> SEQ ID NO 115

<400> SEQUENCE: 115

000

<210> SEQ ID NO 116
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
```

```
<220> FEATURE:
<223> OTHER INFORMATION: Description of Combined DNA/RNA Molecule:
      Synthetic oligonucleotide

<400> SEQUENCE: 116
gguuuuaaug gauaaaucat t                                              21

<210> SEQ ID NO 117
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 117
ugauuuaucc auuaaaacct t                                              21

<210> SEQ ID NO 118

<400> SEQUENCE: 118

000

<210> SEQ ID NO 119
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 119
gacuuugcag agcaauauut t                                              21

<210> SEQ ID NO 120
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 120
aauauugcuc ugcaaaguct t                                              21

<210> SEQ ID NO 121

<400> SEQUENCE: 121

000

<210> SEQ ID NO 122
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
```

```
<223> OTHER INFORMATION: Description of Combined DNA/RNA Molecule:
      Synthetic oligonucleotide

<400> SEQUENCE: 122
cuuacggguc auccaaaaat t                                              21

<210> SEQ ID NO 123
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 123
uuuuuggaug acccguaagt t                                              21

<210> SEQ ID NO 124

<400> SEQUENCE: 124

000

<210> SEQ ID NO 125
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 125
ggaucaucuc aagucuuact t                                              21

<210> SEQ ID NO 126
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 126
guaagacuug agaugaucct t                                              21

<210> SEQ ID NO 127
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 127
gcaaaggcgu gccaacucat                                                20
```

```
<210> SEQ ID NO 128
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 128
ugaguuggca cgccuuugcu u                                                   21

<210> SEQ ID NO 129
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 129
cuauuuggag agaaaucgat                                                     20

<210> SEQ ID NO 130
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 130
ggaucaucuc aagucuuact t                                                   21

<210> SEQ ID NO 131
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 131
guaagacuug agaugaucct t                                                   21

<210> SEQ ID NO 132
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 132
ucgauuucuc uccaaauagu u                                                   21

<210> SEQ ID NO 133
<211> LENGTH: 20
<212> TYPE: DNA
<213> ORGANISM: Artificial Sequence
<220> FEATURE:
```

```
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 133
gcaaaggcgu gccaacucat                                                     20

<210> SEQ ID NO 134
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 134
cuauuuggag agaaaucgat                                                     20

<210> SEQ ID NO 135
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 135
aacaguguuc uugcucuaua at                                                  22

<210> SEQ ID NO 136
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 136
ucgauuucuc uccaaauagu u                                                   21

<210> SEQ ID NO 137
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 137
gcaaaggcgu gccaacucat                                                     20

<210> SEQ ID NO 138
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
```

```
<220> FEATURE:
<223> OTHER INFORMATION: Description of Combined DNA/RNA Molecule:
      Synthetic oligonucleotide

<400> SEQUENCE: 138
gcaaaggcgu gccaacucat                                                 20

<210> SEQ ID NO 139
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 139
ugaguuggca cgccuuugcu u                                               21

<210> SEQ ID NO 140
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 140
cuauuuggag agaaaucgat                                                 20

<210> SEQ ID NO 141
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 141
ucgauuucuc uccaaauagu u                                               21

<210> SEQ ID NO 142
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 142
aacaguguuc uugcucuaua at                                              22

<210> SEQ ID NO 143
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 143
uuauagagca agaacacugu uuu                                             23
```

<210> SEQ ID NO 144
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 144
cuauuuggag agaaaucgat                                              20

<210> SEQ ID NO 145
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 145
aacaguguuc uugcucuaua at                                           22

<210> SEQ ID NO 146
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 146
ggaucaucuc aagucuuact t                                            21

<210> SEQ ID NO 147
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 147
guaagacuug agaugaucct t                                            21

<210> SEQ ID NO 148
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 148
ggaucaucuc aagucuuact t                                            21

<210> SEQ ID NO 149
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 149
guaagacuug agaugaucct t                                              21

<210> SEQ ID NO 150
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 150
ggaucaucuc aagucuuact t                                              21

<210> SEQ ID NO 151
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 151
ggaucaucuc aagucuuact t                                              21

<210> SEQ ID NO 152
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 152
guaagacuug agaugaucct t                                              21

<210> SEQ ID NO 153
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

```
<400> SEQUENCE: 153
guaagacuug agaugaucct t                                              21

<210> SEQ ID NO 154
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 154
ggaucaucuc aagucuuact t                                              21

<210> SEQ ID NO 155
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 155
ggaucaucuc aagucuuact t                                              21

<210> SEQ ID NO 156
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 156
guaagacuug agaugaucct t                                              21

<210> SEQ ID NO 157
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 157
guaagacuug agaugaucct t                                              21

<210> SEQ ID NO 158
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
```

```
<220> FEATURE:
<223> OTHER INFORMATION: Description of Combined DNA/RNA Molecule:
      Synthetic oligonucleotide

<400> SEQUENCE: 158
guaagacuug agaugaucct t                                                  21

<210> SEQ ID NO 159
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 159
ggaucaucuc aagucuuact t                                                  21

<210> SEQ ID NO 160
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 160
ggaucaucuc aagucuuact t                                                  21

<210> SEQ ID NO 161
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 161
guaagacuug agaugaucct t                                                  21

<210> SEQ ID NO 162
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 162
ggaucaucuc aagucuuact t                                                  21

<210> SEQ ID NO 163
<211> LENGTH: 21
<212> TYPE: DNA
<213> ORGANISM: Artificial Sequence
```

```
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 163
ggaucaucuc aagucuuact t                                              21

<210> SEQ ID NO 164
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 164
guaagacuug agaugaucct t                                              21
```